(12) United States Patent
Joung et al.

(10) Patent No.: US 10,894,950 B2
(45) Date of Patent: Jan. 19, 2021

(54) TAL-TET1 FUSION PROTEINS AND METHODS OF USE THEREOF

(71) Applicant: The General Hospital Corporation, Boston, MA (US)

(72) Inventors: J. Keith Joung, Winchester, MA (US); Morgan Maeder, Brookline, MA (US); James Angstman, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 319 days.

(21) Appl. No.: 15/894,004

(22) Filed: Feb. 12, 2018

(65) Prior Publication Data
US 2018/0187168 A1    Jul. 5, 2018

Related U.S. Application Data

(62) Division of application No. 13/838,520, filed on Mar. 15, 2013, now Pat. No. 9,890,364.

(60) Provisional application No. 61/652,711, filed on May 29, 2012.

(51) Int. Cl.
    *C12N 9/02* (2006.01)

(52) U.S. Cl.
    CPC ........ *C12N 9/0071* (2013.01); *C07K 2319/80* (2013.01); *C07K 2319/81* (2013.01)

(58) Field of Classification Search
    CPC ............ C07K 2319/80; C07K 2319/81; C12N 9/0071
    See application file for complete search history.

(56) References Cited

U.S. PATENT DOCUMENTS

| | | | |
|---|---|---|---|
| 4,603,044 A | 7/1986 | Geho et al. | |
| 4,797,368 A | 1/1989 | Carter et al. | |
| 4,957,773 A | 9/1990 | Spencer et al. | |
| 6,007,988 A | 12/1999 | Choo et al. | |
| 6,013,453 A | 1/2000 | Choo et al. | |
| 6,453,242 B1 | 9/2002 | Eisenberg et al. | |
| 6,492,117 B1 | 12/2002 | Choo et al. | |
| 6,503,717 B2 | 1/2003 | Case et al. | |
| 6,511,808 B2 | 1/2003 | Wolffe et al. | |
| 6,534,261 B1 | 3/2003 | Cox, III et al. | |
| 7,001,768 B2 | 2/2006 | Wolfe et al. | |
| 7,220,719 B2 | 5/2007 | Case | |
| 7,741,086 B2 | 6/2010 | Shi | |
| 7,914,796 B2 | 3/2011 | Miller | |
| 8,034,598 B2 | 10/2011 | Miller | |
| 8,071,370 B2 | 12/2011 | Wolffe | |
| 8,771,986 B2 | 7/2014 | Miller | |
| 8,962,281 B2 | 2/2015 | Doyon | |
| 10,273,271 B2 | 4/2019 | Joung et al. | |
| 2002/0160940 A1 | 1/2002 | Case et al. | |
| 2002/0106680 A1 | 8/2002 | Shinmyo | |
| 2002/0119498 A1 | 8/2002 | Joung et al. |
| 2002/0164575 A1 | 11/2002 | Case et al. |
| 2003/0083283 A1 | 5/2003 | Bennett et al. |
| 2006/0115850 A1 | 6/2006 | Schatz |
| 2008/0131962 A1 | 6/2008 | Miller |
| 2009/0133158 A1 | 5/2009 | Lahaye et al. |
| 2010/0132069 A1 | 5/2010 | Lahaye et al. |
| 2011/0059502 A1 | 3/2011 | Chalasani |
| 2011/0112040 A1 | 5/2011 | Liu et al. |
| 2011/0301073 A1 | 12/2011 | Gregory et al. |
| 2012/0064620 A1 | 3/2012 | Bonas |
| 2012/0100569 A1 | 4/2012 | Liu et al. |
| 2013/0323220 A1 | 12/2013 | Joung et al. |
| 2014/0274812 A1 | 9/2014 | Joung et al. |
| 2015/0267176 A1 | 9/2015 | Joung et al. |
| 2015/0376626 A1 | 12/2015 | Joung et al. |
| 2016/0010076 A1 | 1/2016 | Joung et al. |
| 2016/0024523 A1 | 1/2016 | Joung et al. |

FOREIGN PATENT DOCUMENTS

| | | |
|---|---|---|
| EP | 1941060 | 7/2008 |
| EP | 2206723 | 7/2010 |
| JP | 2003-501069 | 1/2003 |
| JP | 2003-531616 | 10/2003 |
| JP | 2013-529083 | 7/2013 |
| JP | 2015-527889 | 9/2015 |
| WO | WO 1991/016024 | 10/1991 |
| WO | WO 1991/017424 | 11/1991 |
| WO | WO 9319202 | 9/1993 |
| WO | WO 1993/024641 | 12/1993 |
| WO | WO 9517413 | 6/1995 |
| WO | WO 9810095 | 3/1998 |
| WO | WO 9947536 | 9/1999 |
| WO | WO 00/75368 | 12/2000 |
| WO | WO 2001/019981 | 3/2001 |
| WO | WO 2001/053480 | 7/2001 |
| WO | WO 0183732 | 11/2001 |
| WO | WO 2002/057308 | 7/2002 |
| WO | WO 2002/099084 | 12/2002 |
| WO | WO 2004/099366 | 11/2004 |
| WO | WO 2006/071608 | 7/2006 |
| WO | WO 2007/128982 | 11/2007 |
| WO | WO 2009/134409 | 11/2009 |
| WO | WO 2010/037001 | 4/2010 |
| WO | WO 2010/079430 | 7/2010 |
| WO | WO 2011/017293 | 2/2011 |
| WO | WO 2011/019385 | 2/2011 |

(Continued)

OTHER PUBLICATIONS

Beerli et al., "Toward controlling gene expression at will: Specific regulation of the erbB-2/HER-2 promoter using polydactyl zinc finger proteins constructed from modular building blocks," Proc. Natl. Acad. Sci., U.S.A., 1998, 95(25):14628-14633.

(Continued)

*Primary Examiner* — Jennifer Dunston
(74) *Attorney, Agent, or Firm* — Fish & Richardson P.C.

(57) ABSTRACT

Fusion proteins comprising a DNA binding domain, e.g., a TAL effector repeat array or zinc finger, and a catalytic domain comprising a sequence that catalyzes hydroxylation of methylated cytosines in DNA, and methods of use thereof.

14 Claims, 15 Drawing Sheets

Specification includes a Sequence Listing.

(56) References Cited

FOREIGN PATENT DOCUMENTS

| WO | WO 2011/072246 | 6/2011 |
|---|---|---|
| WO | WO 2011/146121 | 11/2011 |
| WO | WO 2012/138939 | 10/2012 |
| WO | WO 2013/012674 | 1/2013 |
| WO | WO 2013/017950 | 2/2013 |

OTHER PUBLICATIONS

GenBank Accession No. FJ176909.1, "Xanthomonas oryzae pv. oryzae clone D41 avirulence/virulence factor repeat domain protein-like gene, complete sequence," dated Sep. 30, 2008 [retrieved on Aug. 30, 2018]. Retrieved from the Internet: URL <https://www.ncbi.nlm.nih.gov/nuccore/FJ176909.1/> 2 pages.
GEO Sample G5M1008573, Duke DnaseSeq HEK293T, Sep. 25, 2012, printed as pp. 1/2-282 from <https://www.ncbi.nlrn.nih.gov/geo/query/acc.cgi?acc=GSM1008573> 2 pages.
Office Action in Australian Application No. 2017204819, dated Sep. 7, 2018, 7 pages.
Office Action in Canadian Application No. 2,841,710, dated May 11, 2018, 4 pages.
Office Action in Japanese Application No. 2017-136828, dated Sep. 11, 2018, 7 pages (with English translation).
U.S. Appl. No. 61/610,212, filed Mar. 13, 2012, Joung et al.
Akopian et al., "Chimeric recombinases with designed DNA sequence recognition," Proc Natl Acad Sci USA, Jul. 22, 2003;100(15):8688-91.
Alvarez and Curiel, "A phase I study of recombinant adenovirus vector-mediated intraperitoneal delivery of herpes simplex virus thymidine kinase (HSV-TK) gene and intravenous ganciclovir for previously treated ovarian and extraovarian cancer patients," Hum. Gene Ther., Mar. 1997, 5:597-613.
Anders and Huber, "Differential expression analysis for sequence count data," Genome Biol., 11(10):R106, Epub Oct. 27, 2010.
Arimondo et al., "Exploring the Cellular Activity of Camptothecin—Triple-Helix-Forming Oligonucleotide Conjugates," Mol. Cell. Biol., 26(1):324-33 (2006).
Arnould et al., "Engineering of large numbers of highly specific homing endonucleases that induce recombination on novel DNA targets," J Mol Biol., 355(3):443-458, Epub Nov. 15, 2005.
Arnould et al., "The I-CreI meganuclease and its engineered derivatives: applications from cell modification to gene therapy," Protein Eng Des Sel., 24(1-2):27-31, Epub Nov. 3, 2010.
Bae et al., "Human zinc fingers as building blocks in the construction of artificial transcription factors," Nat Biotechnol., 21(3):275-280, Epub Feb. 18, 2003.
Bannister et al., "Histone methylation: Dynamic or static?," Cell, Jun. 28, 2002, 109(7): 801-806.
Batt, C.A., Chapter 14. Genetic Engineering of Food Proteins in Food Proteins and Their Applications, Damodaran, S., Ed. CRC Press, Mar. 12, 1997, p. 425.
Beerli and Barbas, "Engineering polydactyl zinc-finger transcription factors," Nat Biotechnol., 20(2):135-141, Feb. 2002.
Bello et al., "Hypermethylation of the DNA repair gene MGMT: association with TP53 G:C to A:T transitions in a series of 469 nervous system tumors," Mutat. Res., Oct. 2004, 554:23-32.
Berg, "Proposed structure for the zinc-binding domains from transcription factor IIIA and related proteins," Proc Natl Acad Sci U S A., 85(1):99-102, Jan. 1988.
Bergmann et al. Epigenetic engineering shows H3K4me2 is required for HJURP targeting and CENP-A assembly on a synthetic human kinetochore. The EMBO Journal, vol. 30, pp. 328-340, Jan. 2011, published online Dec. 14, 2010, including pp. 1/14-14/14 of Supplementary Data.
Biancotto et al., "Histone modification therapy of cancer," Adv Genet., 70:341-386, 2010.
Bibikova et al., "Enhancing gene targeting with designed zinc finger nucleases," Science, May 2, 2003;300(5620):764.

Bibikova et al., "Stimulation of homologous recombination through targeted cleavage by chimeric nucleases," Mol Cell Biol., Jan. 2001;21(1):289-97.
Blaese et al., "T lymphocyte-directed gene therapy for ADA-SCID: initial trial results after 4 years," Science, Oct. 1995, 270(5235):475-480.
Blancafort et al., "Designing transcription factor architectures for drug discovery," Mol Pharmacol., 66(6):1361-1371, Epub Aug. 31, 2004.
Boch et al., "Breaking the code of DNA binding specificity of TAL-type III effectors," Science, 326(5959):1509-1512, Dec. 11, 2009.
Boch et al., "Xanthomonas AvrBs3 family-type III effectors: discovery and function," Annu Rev Phytopathol., 48:419-436, 2010.
Boch, "TALEs of genome targeting," Nat Biotechnol., 29(2):135-136, Feb. 2011.
Bogdanove & Voytas, "TAL Effectors: Customizable Proteins for DNA Targeting," Science, 333:1843-1846 (2011).
Bogdanove et al., "TAL effectors: finding plant genes for disease and defense," Curr. Opin. Plant Biol., 13:394-401 (2010).
Bonas et al., "Genetic and Structural Characterization of the Avirulence Gene AVR-BS3 From Xanthomonas-Campestris Pathovar Vesicatoria," Molecular and General Genetics, Jul. 1989, 218(1): 127-136.
Boyle et al., "High-resolution mapping and characterization of open chromatin across the genome," Cell., 132(2):311-322, Jan. 25, 2008.
Briggs et al., "Iterative capped assembly: rapid and scalable synthesis of repeat-module DNA such as TAL effectors from individual monomers," Nucleic Acids Res., Aug. 2012;40(15):e117.
Bulger and Groudine, "Functional and mechanistic diversity of distal transcription enhancers," Cell., 144(3):327-339, Feb. 4, 2011.
Bultmann et al., "Targeted transcriptional activation of silent oct4 pluripotency gene by combining designer TALEs and inhibition of epigenetic modifiers," Nucleic Acids Res., 40(12):5368-77. Epub Mar. 2, 2012.
Burnett et al., "Conditional macrophage ablation in transgenic mice expressing a Fas-based suicide gene," J. Leukoc. Biol., Apr. 2004, 75(4):612-623.
Cade et al., "Highly efficient generation of heritable zebrafish gene mutations using homo- and heterodimeric TALENs," Nucleic Acids Res., Sep. 2012, 40(16):8001-10.
Cabo and Wysocka, "Modification of enhancer chromatin: what, how, and why?" Mol Cell., Mar. 2013, 49(5):825-837.
Carbonetti et al., "Use of pertussis toxin vaccine molecule PT19K/129G to deliver peptide epitopes for stimulation of a cytotoxic T lymphocyte response," Abstr. Annu. Meet. Am. Soc. Microbiol., 1995, 95:295.
Carey et al., "A mechanism for synergistic activation of a mammalian gene by GAL4 derivatives," Nature, 345(6273):361-364, May 24, 1990.
Caron et al., "Intracellular Delivery of a Tat-eGFP Fusion Protein into Muscle Cells," Mol Ther., Mar. 2001, 3:310-318.
Carroll et al., "Design, construction and in vitro testing of zinc finger nucleases," Nat Protoc., 1(3):1329-1341, 2006.
Carroll, "Progress and prospects: zinc-finger nucleases as gene therapy agents," Gene Ther., 15(22):1463-1468, Epub Sep. 11, 2008.
Castellano et al., "Inducible recruitment of Cdc42 or WASP to a cell-surface receptor triggers actin polymerization and filopodium formation," Curr. Biol., 1999, 9(7): 351-360.
Cathomen and Joung, "Zinc-finger nucleases: the next generation emerges," Mol Ther., 16(7):1200-1207, Epub Jun. 10, 2008.
Cermak et al., "Efficient design and assembly of custom TALEN and other TAL effector-based constructs for DNA targeting," Nucleic Acids Res., 39:e82, p. 1-11 (2011).
Chaikind et al., "Targeted DNA Methylation Using an Artificially Bisected M.HhaI Fused to Zinc Fingers," PLoS ONE, 7(9):E44852 pp. 1-11 (2012).
Chase et al., "Histone methylation at H3K9: evidence for a restrictive epigenome in schizophrenia," Schizophr Res., 149(1-3):15-20, Epub Jun. 28, 2013.
Chen et al., "Crystal structure of human histone lysine-specific demethylase 1 (LSD1)," Proc Natl Acad Sci U S A., 103(38):13956-13961, Epub Sep. 6, 2006.

(56) References Cited

OTHER PUBLICATIONS

Chen et al., "Fusion protein linkers: property, design and functionality," Adv Drug Deliv Rev., 65(10):1357-1369, [author manuscript] Epub Sep. 29, 2012.
Chen et al., "Induced DNA demethylation by targeting Ten-Eleven Translocation 2 to the human ICAM-1 promoter," Nucleic Acids Res., 42(3):1563-1574, Epub Nov. 4, 2013.
Chim et al., "Methylation profiling in multiple myeloma," Leuk. Res., Apr. 2004, 28:379-85.
Choo and Klug, "Toward a code for the interactions of zinc fingers with DNA: selection of randomized fingers displayed on phage," Proc Natl Acad Sci U S A., 91(23):11163-11167, Nov. 8, 1994.
Christian et al., "Targeting DNA Double-Strand Breaks with TAL Effector Nucleases," Genetics, 2010, 186:757-761 (2010).
Chylinski et al., "The tracrRNA and Cas9 families of type II CRISPR-Cas immunity systems," RNA Biol., 10(5):726-737, Epub Apr. 5, 2013.
Coffman et al., "Improved renal function in mouse kidney allografts lacking MHC class I antigens," J. Immunol., Jul. 1993, 151:425-35.
Cong et al., "Comprehensive interrogation of natural TALE DNA-binding modules and transcriptional repressor domains," Nat Commun., 3:968, [author manuscript] Jul. 24, 2012.
Cong et al., "Multiplex genome engineering using CRISPR/Cas systems," Science, 339(6121):819-823, Epub Jan. 3, 2013.
Consortium, The ENCODE Project, "An integrated encyclopedia of DNA elements in the human genome," Nature, Sep. 2012, 488:57-74.
Copeland et al., "Targeting genetic alterations in protein methyltransferases for personalized cancer therapeutics," Oncogene., 32(8):939-946, Epub Nov. 19, 2012.
Costa et al., "REELIN and schizophrenia: a disease at the interface of the genome and the epigenome," Mol. Interv., Feb. 2002, 2:47-57.
Crabtree and Schreiber, "Three-part inventions: intracellular signaling and induced proximity," Trends Biochem. Sci., Nov. 1996, 21(11):418-422.
Creyghton et al., "Histone H3K27ac separates active from poised enhancers and predicts developmental state," Proc Natl Acad Sci U S A., 107(50):21931-21936, Epub Nov. 24, 2010.
Cronican et al., "A Class of Human Proteins that Deliver Functional Proteins into Mammalian Cells In Vitro and In Vivo," Chem Biol., Jul. 2011, 18:833-838.
Cronican et al., "Potent Delivery of Functional Proteins into Mammalian Cells in Vitro and in Vivo Using a Supercharged Protein," ACS Chem. Biol., 2010, 5:747.
D'Avignon et al., "Site-specific experiments on folding/unfolding of Jun coiled coils: thermodynamic and kinetic parameters from spin inversion transfer nuclear magnetic resonance at leucine-18," Biopolymers, 83(3):255-267, Oct. 15, 2006.
Davis, "Transcriptional regulation by MAP kinases," Mol Reprod Dev., Dec. 1995;42(4):459-67.
De Zhu, "The altered DNA methylation pattern and its implications in liver cancer," Cell. Res., 2005, 15:272-80.
Derossi et al., "The Third Helix of the Antennapedia Homeodornain Translocates through Biological Membranes," J. Biol. Chem., Apr. 1994, 269:10444.
Deshayes et al., "Cell-penetrating peptides: tools for intracellular delivery of therapeutics," Cell. Mol. Life Sci., Aug. 2005, 62:1839-49.
Dhami et al., "Genomic approaches uncover increasing complexities in the regulatory landscape at the human SCL (TAL1) locus," PLoS One, 5(2):e9059, Feb. 5, 2010.
Donnelly et al., "Targeted delivery of peptide epitopes to class I major histocompatibility molecules by a modified Pseudomonas exotoxin," PNAS, Apr. 1993, 90:3530-34.
Doyle et al., "TAL Effector-Nucleotide Targeter (TALE-NT) 2.0: tools for TAL effector design and target prediction," Nucleic Acids Res., 40(Web Server issue):W117-W122, Epub Jun. 12, 2012.

Doyle, Computational and experimental analysis of TAL effector-DNA binding [dissertation], Jan. 2013, Iowa State University, Ames, Iowa, 162 pages.
Doyon et al., "Heritable targeted gene disruption in zebrafish using designed zinc-finger nucleases," Nat Biotechnol., Jun. 2008, 26:702-708.
Dranoff et al., "A phase I study of vaccination with autologous, irradiated melanoma cells engineered to secrete human granulocyte-macrophage colony stimulating factor," Hum. Gene Ther., Jan. 1997, 8(1):111-23.
Dreidax et al., "Low p14ARF expression in neuroblastoma cells is associated with repressed histone mark status, and enforced expression induces growth arrest and apoptosis," Hum Mol Genet., 22(9):1735-1745, May 1, 2013.
Dunbar et al., "Retrovirally Marked CD34-Enriched Peripheral Blood and Bone Marrow Cells Contribute to Long-Term Engraftment After Autologous Transplantation ," Blood, Jun. 1995, 85:3048-3057.
Ernst, J. et al., "Mapping and analysis of chromatin state dynamics in nine human cell types," Nature, 2011, 473:43-49.
Eisenschmidt et al., "Developing a programmed restriction endonuclease for highly specific DNA cleavage," Nucleic Acids Res., 33(22):7039-47 (2005).
Ellem et al., "A case report: immune responses and clinical course of the first human use of granulocyte/macrophage-colony-stimulating-factor-transduced autologous melanoma cells for immunotherapy," Immunol Immunother., Mar. 1997, 44:10-20.
Elliot and O'Hare, "Intercellular trafficking and protein delivery by a herpesvirus structural protein," Cell, 88(2):223-233, Jan. 24, 1997.
El-Andaloussi et al., "Cell-penetrating peptides: mechanisms and applications," Curr. Pharm. Des., 2005, 11:3597-3611.
Elrod-Erickson et al., "High-resolution structures of variant Zif268-DNA complexes: implications for understanding zinc finger-DNA recognition," Structure, 6(4):451-464, Apr. 15, 1998.
Endoh et al., "Cellular siRNA delivery using TatU1A and photo-induced RNA interference," Methods Mol. Biol., 2010, 623:271-281.
Esteller et al., "A Gene Hypermethylation Profile of Human Cancer," Cancer Res., Apr. 2001, 61:3225-9.
Esteller et al., "Promoter Hypermethylation and BRCA1 Inactivation in Sporadic Breast and Ovarian Tumors," J. Natl. Cancer Inst., Apr. 2000, 92:564-9.
Evans et al., Protoplasts Isolation and Culture, Handbook of Plant Cell Culture, pp. 124-176 (1983).
Evans et al., Binding, Regeneration of Plants, Plant Protoplasts, pp. 21-73 (1985).
Extended European Search Report in European Application No. 13797024, dated Mar. 15, 2016, 9 pages.
Extended European Search Report in European Application No. 13845212, dated Apr. 29, 2016, 6 pages.
Extended European Search Report in European Application No. 12814750.1, dated Jun. 30, 2015,13 pages.
Fahraeus et al., "Inhibition of pRb phosphorylation and cell-cycle progression by a 20-residue peptide derived from p16CDKN2/INK4A," Curr Biol., 6(1):84-91, Jan. 1, 1996.
Fonfara et al., "Creating highly specific nucleases by fusion of active restriction endonucleases and catalytically inactive homing endonucleases," Nucleic Acids Res., 40(2):847-860, Epub Sep. 29, 2011.
Freeman et al., "Inducible Prostate Intraepithelial Neoplasia with Reversible Hyperplasia in Conditional FGFR1-Expressing Mice," Cancer Res., Dec. 2003, 63(23):8256-8563.
Foley et al., "Targeted mutagenesis in zebrafish using customized zinc-finger nucleases", Nature Protocols, Nature Publishing Group, Jan. 2009, 4(12):1855-1868.
Futaki, "Oligoarginine vectors for intracellular delivery: design and cellular-uptake mechanisms," Biopolymers, 2006, 84:241-249.
Gao et al., "Hypermethylation of the RASSF1A gene in gliomas," Clin. Chim. Acta., Nov. 2004, 349:173-9.
Garcia-Bustos et al., "Nuclear protein localization," Biochim Biophys Acta., 1071(1):83-101, Mar. 7, 1991.

(56) References Cited

OTHER PUBLICATIONS

Garg et al., "Engineering synthetic TAL effectors with orthogonal target sites," Nucleic Acids Res., 40(15):7584-7595, Epub May 11, 2012.
Gavin et al., "Dimethylated lysine 9 of histone 3 is elevated in schizophrenia and exhibits a divergent response to histone deacetylase inhibitors in lymphocyte cultures," J. Psychiatry Neurosci., May 2009, 34(3):232-7.
Geibler et al., "Transcriptional Activators of Human Genes with Programmable DNA-Specificity ," PLoS ONE, 6:e19509 (2011).
GenBank Accession No. NM_ 001009999.2, "*Homo sapiens* lysine (K)-specific demethylase 1A (KDM1A), transcript variant 1, mRNA," Apr. 6, 2014, 6 pages.
GenBank Accession No. NP_055828.2, "lysine-specific histone demethylase 1A isoform b [*Homo sapiens*]," Apr. 6, 2014, 4 pages.
GenBank Accesssion No. NM_015013.3, "*Homo sapiens* lysine (K)-specific demethylase 1A (KDM1A), transcript variant 2, mRNA," Apr. 6, 2014, 6 pages.
Gong and Zhu, "Active DNA demethylation by oxidation and repair," Cell Research, 2011, 21:1649-1651.
Gillies et al., "A tissue-specific transcription enhancer element is located in the major intron of a rearranged immunoglobulin heavy chain gene," Cell, 33(3):717-728, Jul. 1983.
Gossen and Bujard, "Tight control of gene expression in mammalian cells by tetracycline-responsive promoters," Proc Natl Acad Sci U S A., 89(12):5547-5551, Jun. 15, 1992.
Graef et al., "Proximity and orientation underlie signaling by the non-receptor tyrosine kinase ZAP70," Embo. J., 1997, 16(18):5618-5628.
Gregory et al., "Selective DNA demethylation by fusion of TOG with a sequence-specific DNA-binding domain", EPIGENETICS, Apr. 2012, 7(4):344-349.
Grizot et al., "Generation of redesigned homing endonucleases comprising DNA-binding domains derived from two different scaffolds," Nucleic Acids Res., 38(6):2006-2018, Epub Dec. 21, 2009.
Gross and Garrard, "Nuclease Hypersensitive Sites in Chromatin," Annu. Rev. Biochem., Jul. 1988, 57:159-97.
Gruen et al., "An in vivo selection system for homing endonuclease activity," Nucleic Acids Res., 30(7):e29, Apr. 1, 2002.
Gu et al., "R gene expression induced by a type-III effector triggers disease resistance in rice," Nature, Jun. 23, 2005;435(7045):1122-5.
Guo et el., "Hydroxylation of 5-Methylcytosine by TET1 Promotes Active DNA Demethylation in the Adult Brain ," Cell, 145:423-434 (2011).
Hakimi et al., "A core-BRAF35 complex containing histone deacetylase mediates repression of neuronal-specific genes," Proceedings of the National Academy of Sciences of the United States of America, May 28, 2002, 99(11): 7420-7425.
Han et al., "Ligand-directed retroviml targeting of human breast cancer cells," PNAS, Oct. 1995, 92:9741-51.
Han et al., "CTCF is the Master Organizer of Domain-Wide Allele-Specific Chromatin at the H19/Igf2 Imprinted Region," Mol Cell Biol., Feb. 2008, 28(3):1124-35.
Harikrishna et al., "Construction and function of fusion enzymes of the human cytochrome P450scc system," DNA Cell Biol., 12(5):371-379, Jun. 1993.
Harrison, "A structural taxonomy of DNA-binding domains," Nature, 353(6346): 715-719, Oct. 24, 1991.
He et al., "Tet-Mediated Formation of 5-Carboxylcytosine and its Excision by TDG in Mammalian DNA," Science, 333:1303-1307 (2011).
Heintzman et al., "Histone modifications at human enhancers reflect global cell-type-specific gene expression," Nature, 459(7243):108-112, Epub Mar. 18, 2009.
Heppard et al., "Developmental and Growth Temperature Regulation of Two Different Microsomal [omega]-6 Desaturase Genes in Soybeans," Plant Physiol., 1996, 110:311-319.
Hermonat & Muzyczka, "Use of adeno-associated virus as a mammalian DNA cloning vector: Transduction of neomycin resistance into mammalian tissue culture cells," PNAS, Oct. 1984, 81:6466-70.
Hockemeyer et al., "Genetic engineering of human pluripotent cells using Tale nucleases," Nat.Biotechnol., 29:731-734 (2011).
Hoivik et al., "DNA methylation of intronic enhancers directs tissue-specific expression of steroidogenic factor 1/adrenal 4 binding protein (SF-1/Ad4BP)," Endocrinology, 152(5):2100-2112, Epub Feb. 22, 2011.
Hopp et al., "A Short Polypeptide Marker Sequence Useful for Recombinant Protein Identification and Purification," BioTechnology, Oct. 1988, 6:1204-10.
Hsu and Zhang, "Dissecting neural function using targeted genome engineering technologies," ACS Chem Neurosci., 3(8):603-610, Epub Jul. 19, 2012.
Huang et al., "Heritable gene targeting in zebrafish using customized TALENs," Nat. Biotechnol., 29:699-700 (2011).
Huang Shi, "Histone methyltransferases, diet nutrients and tumour suppressors," Nature Reviews. Cancer, Jun. 2002, 2(6): 469-7.476.
Humphrey et al., "Stable histone deacetylase complexes distinguished by the presence of SANT domain proteins CoREST/kiaa0071 and Mta-L1," Journal of Biological Chemistry, Mar. 2, 2001, 276(9): 6817-6824.
Inaba et al., "Generation of large numbers of dendritic cells from mouse bone marrow cultures supplemented with granulocyte/macrophage colony-stimulating factor," J Exp Med., 176(6):1693-1702, Dec. 1, 1992.
Isalan et al., "A rapid, generally applicable method to engineer zinc fingers illustrated by targeting the HIV-1 promoter," Nat. Biotechnol., 19(7):656-660, Jul. 2001.
Ito et al., "Tet proteins can convert 5-methylcytosine to 5-formylcytosine and 5-carboxylcytosine," Science, 333(6047):1300-1303, Sep. 2, 2011.
Iyer et al., "Prediction of novel families of enzymes involved in oxidative and other complex modifications of bases in nucleic acids," Cell Cycle, Jun. 2009, 8(11):1698-1710.
Jamieson et al., "In vitro selection of zinc fingers with altered DNA-binding specificity," Biochemistry, 33(19):5689-5695, May 17, 1994.
Jinek et al., "A programmable dual-RNA-guided DNA endonuclease in adaptive bacterial immunity," Science, 337(6096):816-821, Epub Jun. 28, 2012.
Joung and Sander, "TALENs: a widely applicable technology for targeted genome editing," Nat Rev Mol Cell Biol., 14(1):49-55, Epub Nov. 21, 2012.
Joung et al., "A bacterial two-hybrid selection system for studying protein-DNA and protein-protein interactions," Proc Natl Acad Sci USA, Jun. 20, 2000;97(13):7382-7.
Joung et al., "Reply to "Successful genome editing with modularly assembled zinc finger nucleases"," Nat. Methods, Jan. 2010, 7:91-92.
Juillerat et al., "Comprehensive analysis of the specificity of transcription activator-like effector nucleases," Nucleic Acids Res., 42(8):5390-5402, Epub Feb. 24, 2014.
Jumlongras et al., "An evolutionarily conserved enhancer regulates Bmp4 expression in developing incisor and limb bud," PLoS One, 7(6):e38568, Epub Jun. 12, 2012.
Karmirantzou and Harnodrakas, "A Web-based classification system of DNA-binding protein families," Protein Eng. 14(7):465-472, Jul. 2001.
Kay et al., "A bacterial effector acts as a plant transcription factor and induces a cell size regulator," Science, Oct. 26, 2007;318(5850):648-51.
Kearns et al., "Recombinant adeno-associated virus (AAV-CFTR) vectors do not integrate in a site-specific fashion in an immortalized epithelial cell line," Gene Ther., Sep. 1996, 9:748-55.
Kim et al., "Targeted genome editing in human cells with zinc finger nucleases constructed via modular assembly," Genome Res., 19(7):1279-1288, Epub May 21, 2009.
Kim et al., "Hybrid restriction enzymes: zinc finger fusions to Fok I cleavage domain," Proc Natl Acad Sci USA, Feb. 6, 1996;93(3):1156-60.

(56) References Cited

OTHER PUBLICATIONS

Klee et al., "Agrobacterium-Mediated Plant Transformation and its Further Applications to Plant Biology," Ann. Rev. Plant Phys., Jun. 1987, 38:467-486.
Klimpel et al., "Anthrax toxin protective antigen is activated by a cell surface protease with the sequence specificity and catalytic properties of furin," PNAS, Nov. 1992, 89:10277-81.
Klug, "Co-chairman's remarks: protein designs for the specific recognition of DNA," Gene, 135(1-2):83-92, Dec. 15, 1993.
Ko et al., "Impaired hydroxylation of 5-methylcytosine in myeloid cancers with mutant TET2," Nature, Dec. 2010, 468(7325):839-843.
Kohn et al., "Engraftment of gene-modified umbilical cord blood cells in neonates with adenosine deaminase deficiency," Nat. Med., 1995, 1:1017-1023.
Koller et al., "Normal development of mice deficient in beta 2M, MHC class I proteins, and CD8+ T cells," Science, Jun. 1990, 248:1227-30.
Ku et al., "Genomewide analysis of PRC1 and PRC2 occupancy identifies two classes of bivalent domains," PLoS Genet., 4(10):e1000242, Epub Oct. 31, 2008.
Kumar et al., "DNA-Prot: identification of DNA binding proteins from protein sequence information using random forest," J Biomol Struct Dyn., 26(6):679-686, Jun. 2009.
Kumar et al., "Identification of DNA-binding proteins using support vector machines and evolutionary profiles," BMC Bioinformatics, 8:463, Nov. 27, 2007.
Kummerfeld and Teichmann, "DBD: a transcription factor prediction database," Nucleic Acids Res., 34 (Database issue): D74-D81, Jan. 1, 2006.
Kurmasheva et al., "Upstream CpG island methylation of the PAX3 gene in human rhabdomyosarcomas," Pediatr. Blood Cancer, Apr. 2005, 44:328-37.
Lawrence et al., "Supercharging Proteins Can Impart Unusual Resilience," J. Am. Chem. Soc., 2007, 129:10110-10112.
Lea et al., "Aberrant p16 methylation is a biomarker for tobacco exposure in cervical squamous cell carcinogenesis," Am. J. Obstet. Gynecol., 2004, 190:674-9.
Lee et al., "An essential role for CoREST in nucleosomal histone 3 lysine 4 demethylation," Nature, 437(7057):432-435, Epub Aug. 3, 2005.
Lee et al., "Three-dimensional solution structure of a single zinc finger DNA-binding domain," Science., 245(4918):635-637, Aug. 11, 1989.
Li et al., "Modularly assembled designer TAL effector nucleases for targeted gene knockout and gene replacement in eukaryotes," Nucleic Acids Res., 39(14):6315-6325, Epub Mar. 31, 2011.
Li et al., "Protein trans-splicing as a means for viral vector-mediated in vivo gene therapy," Hum Gene Ther., 19(9):958-964, Sep. 2008.
Li et al., "Transcription activator-like effector hybrids for conditional control and rewiring of chromosomal transgene expression," Sci Rep., 2:897, Epub Nov. 28, 2012.
Li et al., "TAL nucleases (TALNs): hybrid proteins composed of TAL effectors and FokI DNA-cleavage domain," Nucl Acids Res, 39:359-372 (2011).
Li et al., "DNA methylation in prostate cancer," Biochim. Biophys. Acta., Sep. 2004, 1704:87-102.
Lin et al., "Inhibition of Nuclear Translocation of Transcription Factor NF-κB by a Synthetic Peptide Containing a Cell Membrane-permeable Motif and Nuclear Localization Sequence," J. Biol. Chem., 1995, 270:14255-58.
Lin et al., "iDNA-Prot: identification of DNA binding proteins using random forest with grey model," PLoS One., 6(9):e24756, Epub Sep. 15, 2011.
Lippow et al., "Creation of a type IIS restriction endonuclease with a long recognition sequence," Nucleic Acids Res., 37(9):3061-3073, May 2009.

Liu et al., "Regulation of an endogenous locus using a panel of designed zinc finger proteins targeted to accessible chromatin regions. Activation of vascular endothelial growth factor A," J Biol Chem., 276(14):11323-11334, Epub Jan. 5, 2001.
Liu et al., "Validated zinc finger protein designs for all 16 GNN DNA triplet targets," J. Biol. Chem., 277(6):3850-3856, Epub Nov. 28, 2001.
Loenarz and Schofield, Oxygenase Catalyzed 5-Methylcytosine Hydroxylation, Chemistry & Biology, Jun. 2009, 16:580-583.
Lund et al., "DNA Methylation Polymorphisms Precede Any Histological Sign of Atherosclerosis in Mice Lacking Apolipoprotein E," J. Biol. Chem., Jul. 2004, 279:29147-54.
Lutz-Freyerinuth et al., "Quantitative determination that one of two potential RNA-binding domains of the a protein component of the U1 small nuclear ribonucleoprotein complex binds with high affinity to stem-loop II of U1 RNA," PNAS, Aug. 1990, 87:6393-97.
Mabaera et al., "Developmental- and differentiation-specific patterns of human γ- and β-globin promoter DNA methylation," Blood, 110(4):1343-52 (2007).
Madrigal and Krajewski, "Current bioinformatic approaches to identify DNase I hypersensitive sites and genomic footprints from DNase-seq data," Front Genet., 3:230, eCollection 2012, Oct. 31, 2012.
Maeder et al., "Rapid "open-source" engineering of customized zinc-finger nucleases for highly efficient gene modification," Mol Cell., 31(2):294-301, Jul. 25, 2008.
Maeder et al., "Robust, synergistic regulation of human gene expression using TALE activators," Nat Methods., 10(3):243-245, Epub Feb. 10, 2013.
Maeder et al., "Targeted DNA demethylation and activation of endogenous genes using programmable TALE-TET1 fusion proteins," Nat Biotechnol., 31(12):1137-1142, [author manuscript] Epub Oct. 9, 2013.
Maeder et al., "Oligomerized pool engineering (OPEN): an 'open-source' protocol for making customized zinc-finger arrays," Nat Protoc., 2009;4(10):1471-501.
Mahfouz et al., "Targeted transcriptional repression using a chimeric TALE-SRDX repressor protein," Plant Mol Biol., 78(3):311-321, Epub Dec. 14, 2011.
Mahfouz et al., "De novo-engineered transcription activator-like effector (TALE) hybrid nuclease with novel DNA binding specificity creates double-strand breaks," Proc Natl Acad Sci U S A, 108:2623-2628 (2011).
Maiti and Drohat, "Thymine DNA glycosylase can rapidly excise 5-formylcytosine and 5-carboxylcytosine: potential implications for active demethylation of CpG sites," J Biol Chem., 286(41):35334-35338, Epub Aug. 23, 2011.
Majumdar et al., "Targeted Gene Knock in and Sequence Modulation Mediated by a Psoralen-linked Triplex-forming Oligonucleotide," J Biol Chem., 283(17):11244-52 (2008).
Malech et al., "Prolonged production of NADPH oxidase-corrected granulocytes after gene therapy of chronic granulomatous disease," PNAS, Oct. 1997, 94:12133-38.
Mancini et al. "CpG methylation within the 5' regulatory region of the BRCA1 gene is tumor specific and includes a putative CREB binding site," Oncogene, 1998, 16:1161-9.
Mandecki et al., "A totally synthetic plasmid for general cloning, gene expression and mutagenesis in *Escherichia coli*," Gene, Sep. 28 1990, 94(1):103-107.
Mandell and Barbas et al., "Zinc Finger Tools: custom DNA-binding domains for transcription factors and nucleases," Nucleic Acids Res., 34(Web Server issue):W516-W523, Jul. 1, 2006.
Markmann et al., "Indefinite survival of MHC class I-deficient murine pancreatic islet allografts," Transplantation, Dec. 1992, 54:1085-89.
Martin et al., "GAP domains responsible for ras p21-dependent inhibition of muscarinic atrial K+ channel currents," Science, Jan. 1992, 255:192-194.
Maurano et al., "Systematic localization of common disease-associated variation in regulatory DNA," Science, 337(6099):1190-1195, Epub Sep. 5, 2012.

(56) References Cited

OTHER PUBLICATIONS

McDaniell et al., "Heritable individual-specific and allele-specific chromatin signatures in humans," Science, 328(5975):235-239, [author manuscript] Epub Mar. 18, 2010.
McNaughton et al., "Mammalian cell penetration, siRNA transfection, and DNA transfection by supercharged proteins," PNAS, Apr. 2009, 106:6111.
Mendenhall et al., "Locus-specific editing of histone modifications at endogenous enhancers," Nat Biotechnol., 31(12):1133-1136, Epub Sep. 8, 2013.
Metzger et al., "LSD1 demethylates repressive histone marks to promote androgen-receptor-dependent transcription," Nature, 437(7057):436-439, 2005.
Miller et al., "A TALE nuclease architecture for efficient genome editing," Nat. Biotechnol., 29(2):143-148, Epub Dec. 22, 2010.
Miller et al., "Repetitive zinc-binding domains in the protein transcription factor IIIA from Xenopus oocytes," EMBO J., 4(6):1609-1614, Jun. 1985.
Moore et al., "Design of polyzinc finger peptides with structured linkers," Proc Natl Acad Sci USA, Feb. 2001, 98:1432-1436.
Moore et al., "Improved somatic mutagenesis in zebrafish using transcription activator-like effector nucleases (TALENs)," PLoS One, May 2012, 7(5):e37877.
Morbitzer et al., "Regulation of selected genome loci using de novo-engineered transcription activator-like effector (TALE)-type transcription factors," Proc Natl Acad Sci U S A., 107(50):21617-21622, Epub Nov. 24, 2010.
Morbitzer et al., "Assembly of custom Tale-type DNA binding domains by modular cloning," Nucl Acids Res., 39:5790-5799 (2011).
Moscou and Bogdanove, "A simple cipher governs DNA recognition by TAL effectors," Science, 326(5959):1501, Dec. 11, 2009.
Mussolino et al., "A novel TALE nuclease scaffold enables high genome editing activity in combination with low toxicity," Nucleic Acids Res., 2011, 39:9283-93.
Muthuswamy et al., "Controlled Dimerization of ErbB Receptors Provides Evidence for Differential Signaling by Homo- and Heterodimers," Mol. Cell. Biol., Oct. 1999, 19(10):6845-6857.
Neering et al., "Transduction of primitive human hematopoietic cells with recombinant adenovirus vectors," Blood, 88(4):1147-1155, Aug. 15, 1996.
Ng et al., "In vivo epigenomic profiling of germ cells reveals germ cell molecular signatures," Dev Cell., 24(3):324-333, Epub Jan. 24, 2013.
Noonan and McCallion, "Genomics of long-range regulatory elements," Annu Rev Genomics Hum Genet., 11:1-23, 2010.
Novak et al., "Functional Characterization of Protease-treated Bacillus anthracis Protective Antigen," J. Biol. Chem., Aug. 1992, 267:17186-93.
Oligino et al., "Drug inducible transgene expression in brain using a herpes simplex virus vector," Gene Ther., 5(4):491-496, Apr. 1998.
Ong and Corees, "Enhancer function: new insights into the regulation of tissue-specific gene expression," Nat Rev Genet., 12(4):283-293, Epub Mar. 1, 2011.
Orlando et al., "Zinc-finger nuclease-driven targeted integration into mammalian genomes using donors with limited chromosomal homology," Nucleic Acids Res., Aug. 2010;38(15):e152, 15 pages.
Ovchinnikov et al., "PspXI, a novel restriction endonuclease that recognizes the unusual DNA sequence 5-VCTCGAGB-3," Bulletin of Biotechnology and Physico-chemical Biology, 2005, 1(1):18-24.
Palva et al., "Secretion of interferon by Bacillus subtilis," Gene, 22(2-3):229-235, May-Jun. 1983.
Paques et al., "Meganucleases and DNA double-strand break-induced recombination: persetives for gene thereapy," Current Gene Therapy, Bentham Science Publishers LTD, Feb. 1, 2007, 7(1): 49-66.
Pavletich and Pabo, "Zinc finger-DNA recognition: crystal structure of a Zif268-DNA complex at 2.1 A," Science, 252(5007):809-817, May 10, 1991.

Paik W K et al., "Enzymatic Demethylation of Calf Thymus Histones," Biochemical and Biophysical Research Communications, 1973, 51(3): 781-788.
Perelle et al., "Characterization of Clostridium perfringens Iota-Toxin Genes and Expression in *Eschenichia coli*," Infect. Immun., Dec. 1993, 61:5147-56.
Perez-Pinera et al., "Synergistic and tunable human gene activation by combinations of synthetic transcription factors," Nat Methods., 10(3):239-342, Epub Feb. 3, 2013.
Pingoud and Silva, "Precision genome surgery," Nat Biotechnol., 25(7):743-744, Jul. 2007.
Porteus & Baltimore, "Chimeric nucleases stimulate gene targeting in human cells," Science. May 2, 2003;300(5620):763.
Prochiantz, "Getting hydrophilic compounds into cells: lessons from homeopeptides," Curr. Opin. Neurobiol., Oct. 1996, 6:629-634.
Qi et al., "Repurposing CRISPR as an RNA-guided platform for sequence-specific control of gene expression," Cell, 152(5):1173-1183, Feb. 28, 2013.
Rada-Iglesias et al., "A unique chromatin signature uncovers early developmental enhancers in humans," Nature, 470(7333):279-283, Epub Dec. 15, 2010.
Ram et al., "Combinatorial patterning of chromatin regulators uncovered by genome-wide location analysis in human cells," Cell, 147(7):1628-1639, Dec. 23, 2011.
Ramirez et al., "Unexpected failure rates for modular assembly of engineered zinc fingers," Nat Methods., 5(5):374-375, May 2008.
Rebar and Pabo, "Zinc finger phage: affinity selection of fingers with new DNA-binding specificities," Science, 263(5147):671-673, Feb. 4, 1994.
Rendahl et al., "Regulation of gene expression in vivo following transduction by two separate rAAV vectors," Nat. Biotechnol., 16(8):757-761, Aug. 1998.
Reyon et al., "Engineering designer transcription activator-like effector nucleases (TALENs) by REAL or REAL-Fast assembly" Curr Protoc Mol Biol., Chapter 12:Unit 12.15, [author manuscript] Oct. 2012.
Reyon et al., "FLASH assembly of TALENs for high-throughput genome editing," Nat Biotechnol., 30(5):460-465, May 2012.
Rivenbank et al., "Epigenetic reprogramming of cancer cells via targeted DNA methylation," Epigenetics, Apr. 2012, 7(4): 350-360.
Rodenhiser and Mann, "Epigenetics and human disease: translating basic biology into clinical applications," CMAJ, 174(3):341-348 (2006).
Rohde et al., "BISMA—Fast and accurate bisulfite sequencing data analysis of individual clones from unique and repetitive sequences," BMC Bioinformatics, 11:230 12 pages (2010).
Romer et al., "Plant pathogen recognition mediated by promoter activation of the pepper Bs3 resistance gene," Science, Oct. 26, 2007;318(5850):645-8.
Rosenbloom et al., "ENCODE whole-genome data in the UCSC Genome Browser: update 2012," Nucleic Acids Res., 40(Database issue):D912-D917, Epub Nov. 9, 2011.
Rosenecker et al., "Adenovirus infection in cystic fibrosis patients: implications for the use of adenoviral vectors for gene transfer," Infection, 1996, 24(1)5-8.
Rothman, "Mechanisms of intracellular protein transport," Nature, 372(6501):55-63, Nov. 3, 1994.
Ruben et al., "Isolation of a rel-related human cDNA that potentially encodes the 65-kD subunit of NF-kappa B," Science, Mar. 1991, 251:1490-93.
Sabo et al, "Genome-scale mapping of DNase I sensitivity in vivo using tiling DNA microarrays," Nat Methods., 3(7):511-518, Jul. 2006.
Sabo et al., "Discovery of functional noncoding elements by digital analysis of chromatin structure," Proc Natl Acad Sci U S A., 101(48):16837-16842, Epub Nov. 18, 2004.
Sadowski et al., "GAL4-VP16 is an unusually potent transcriptional activator," Nature, Oct. 1988, 335:563-564.
Samulski et al., "Helper-Free Stocks of Recombinant Adeno-Associated Viruses: Normal Integration Does Not Require Viral Gene Expression," J. Virol., Sep. 1989, 63:3822-28.

(56) References Cited

OTHER PUBLICATIONS

Sander et al., "Targeted gene disruption in somatic zebrafish cells using engineered TALENs," Nat. Biotechnol., 29:697-698 (2011).
Sanjana et al., "A transcription activator-like effector toolbox for genome engineering," Nat Protoc., 7(1):171-192, Jan. 5, 2012.
Schleifman et al., "Triplex-mediated gene modification," Methods Mol. Biol., 435:175-190, 2008.
Schmidt et al., "Arginine-rich cell-penetrating peptides," FEBS Lett., May 2010, 584:1806-13.
Scholze & Boch, "TAL effectors are remote controls for gene activation," J. Curr. Opin. Microbiol, 14:47-53 (2011).
Schonthal, "Regulation of gene expression by serine/threonine protein phosphatases," Semin Cancer Biol., Aug. 1995;6(4):239-48.
Schornack et al., "Gene-for-gene-mediated recognition of nuclear-targeted AvrBs3-like bacterial effector proteins," J Plant Physiol., Feb. 2006;163(3):256-72.
Sebo et al., "Cell-invasive activity of epitope-tagged adenylate cyclase of Bordetella pertussis allows in vitro presentation of a foreign epitope to CD8+ cytotoxic T cells," Infect. Immun., Oct. 1995, 63:3851-57.
Segal et al., "Evaluation of a modular strategy for the construction of novel polydactyl zinc finger DNA-binding proteins," Biochemistry, 42(7):2137-2148, Feb. 25, 2003.
Sharma, "Schizophrenia, epigenetics and ligand-activated nuclear receptors: a framework for chromatin therapeutics," Schizophr. Res., Jan. 2005, 72:79-90.
Shi et al., "Histone demethylation mediated by the nuclear amine oxidase homolog LSD1," Cell, 119(7):941-953, Dec. 29, 2004.
Shi et al., "Metabolic enzymes and coenzymes in transcription—a direct link between metabolism and transcription?," Trends in Genetics: TIG, Sep. 2004, 20(9): 445-452.
Silva et al., "Meganucleases and other tools for targeted genome engineering: perspectives and challenges for gene therapy," Curr Gene Ther., 11(1):11-27, Feb. 2011.
Silver, "How Proteins Enter the Nucleus," Cell, 64(3):489-497, Feb. 8, 1991.
Simon et al., "Sequence-specific DNA cleavage mediated by bipyridine polyamide conjugates," Nucl. Acids Res., 36(11):3531-8 (2008).
Sipione et al., "Insulin expressing cells from differentiated embryonic stem cells are not beta cells," Diabetologia, 47(3):499-508. Epub Feb. 14, 2004.
Skinner et al., "Use of the Glu-Glu-Phe C-terminal epitope for rapid purification of the catalytic domain of normal and mutant ras GTPase-activating proteins," J. Biol. Chem., 1991, 266:14163-14166.
Stadler et al., "DNA-binding factors shape the mouse methylome at distal regulatory regions," Nature, 480(7378):490-495, Dec. 14, 2011.
Stenmark et al., "Peptides fused to the amino-terminal end of diphtheria toxin are translocated to the cytosol," J. Cell Biol., Jun. 1991, 113:1025-32.
Sterman et al., "Adenovirus-mediated herpes simplex virus thymidine kinase/ganciclovir gene therapy in patients with localized malignancy: results of a phase I clinical trial in malignant mesothelioma," Hum. Gene Ther., May 1998, 7:1083-89.
Stoddard, "Homing endonuclease structure and function," Q. Rev. Biophys., 38(1): 49-95, Epub Dec. 9, 2005.
Stott et al., "The alternative product from the human CDKN2A locus, p14(ARF), participates in a regulatory feedback loop with p53 and MDM2," EMBO J., 17(17):5001-5014, Sep. 1, 1998.
Streubel et al., "TAL effector RVD specificities and efficiencies," Nat Biotechnol., 30(7):593-595, Jul. 10, 2012.
Sugio et al., "Two type III effector genes of Xanthomonas oryzae pv. oryzae control the induction of the host genes OsTFIIAgammal and OsTFX1 during bacterial blight of rice," Proc Natl Acad Sci USA, Jun. 19, 2007;104(25):10720-5.
Szyf et al., "DNA methylation and breast cancer," Biochem. Pharmacol., Sep. 2004, 68:1187-97.

Tahiliani et al., "Conversion of 5-Methylcytosine to 5-Hydroxymethylcytosine in Mammalian DNA by MLL Partner TET1," Science, 324:930-935 (2009).
Tan et al., "Zinc-finger protein-targeted gene regulation: genomewide single-gene specificity," Proc Natl Acad Sci U S A., 100(21):11997-2002, Epub Sep. 26, 2003.
Tesson et al., "Knockout rats generated by embryo microinjection of TALENs," Nat. Biotechnol., 29:695-696 (2011).
Thiesen et al., "Conserved KRAB protein domain identified upstream from the zinc finger region of Kox 8," Nucleic Acids Res., 1991, 19:3996.
Thompson et al., "Engineering and Identifying Supercharged Proteins for Macromolecule Delivery into Mammalian Cells," Methods in Enzymology, 2012, 503:293-319.
Thurman et al., "The accessible chromatin landscape of the human genome," Nature, 489(7414):75-82, Sep. 6, 2012.
Tjong and Zhou, "DISPLAR: an accurate method for predicting DNA-binding sites on protein surfaces," Nucleic Acids Res., 35(5):1465-1477, Epub Feb. 6, 2007.
Topf et al., "Regional 'pro-drug' gene therapy: intravenous administration of an adenoviral vector expressing the E. coli cytosine deaminase gene and systemic administration of 5-fluorocytosine suppresses growth of hepatic metastasis of colon carcinoma," Gene Ther., Apr. 1998, 5:507-513.
Townsend et al., "High-frequency modification of plant genes using engineered zinc-finger nucleases," Nature: International Weekly Journal of Science, Nature Publishing Group, May 21, 2009, pp. 442-445.
Tratschin et al., "Adeno-Associated Virus Vector for High-Frequency Integration, Expression, and Rescue of Genes in Mammalian Cells," Mol. Cell. Biol., Nov. 1985, 5:3251-60.
Tratschin et al., "A human parvovirus, adeno-associated virus, as a eucaryotic vector: transient expression and encapsidation of the procaryotic gene for chloramphenicol acetyltransferase," Mol. Cell. Biol., Oct. 1984, 4:2072-81.
Tremblay et al., "Transcription activator-like effector proteins induce the expression of the frataxin gene," Hum Gene Ther., 23(8):883-890, Epub Jul. 20, 2012.
Uhlman, "An alternative approach in gene synthesis: use of long selfpriming oligodeoxynucleotides for the construction of double-stranded DNA," Gene, Nov. 15, 1988, 71(15): 29-40.
Uhlmann et al., "Distinct methylation profiles of glioma subtypes," Int. J. Cancer, Aug. 2003, 106:52-9.
Urnov et al., "Highly efficient endogenous human gene correction using designed zinc-finger nucleases," Nature, Jun. 2, 2005;435(7042):646-51.
Valton et al., "Overcoming transcription activator-like effector (TALE) DNA binding domain sensitivity to cytosine methylation," J Biol Chem., 287(46):38427-38432, Epub Sep. 26, 2012.
Van den Brulle et al., "A novel solid phase technology for high-throughput gene synthesis," BioTechniques, 45(3):340-343 (2008).
Visel et al., "Genomic views of distant-acting enhancers," Nature, 461(7261):199-205, Sep. 10, 2009.
Vogelstein and Kinzler, "Cancer genes and the pathways they control," Nat. Med., Aug. 2004, 10:789-799.
Voytas and Joung, "Plant Science. DNA binding made easy," Science, Dec. 11, 2009, 326: 1491-1492.
Wagner et al., "Efficient and persistent gene transfer of AAV-CFTR in maxillary sinus," Lancet, Jun. 1998, 351:1702-1703.
Wang et al., "An integrated chip for the high-throughput synthesis of transcription activator-like effectors," Angew Chem Int Ed Engl., 51(34):8505-8508, Epub Jul. 23, 2012.
Wang et al., "Human PADA4 regulates histone arginine methylation levels via demethylimination," Science, Oct. 8, 2004, 306(5694): 279-283.
Wang et al., "pH-sensitive immunoliposomes mediate target-cell-specific delivery and controlled expression of a foreign gene in mouse," PNAS, Nov. 1987, 84:7851-7855.
Wang et al., "Positive and negative regulation of gene expression in eukaryotic cells with an inducible transcriptional regulator," Gene Ther., 4(5):432-441, May 1997.
Weber et al., "Assembly of Designer TAL Effectors by Golden Gate Cloning," PLoS ONE, 6:e19722 (2011).

(56) References Cited

OTHER PUBLICATIONS

Weising et al., "Foreign Genes in Plants: Transfer, Structure, Expression, and Applications," Ann. Rev. Genet., 1988, 22:421-477.
Welsh et al., "Adenovirus-mediated gene transfer for cystic fibrosis: Part A. Safety of dose and repeat administration in the nasal epithelium. Part B. Clinical efficacy in the maxillary sinus," Hum. Gene Ther., Feb. 1995, 6(2):205-218.
Whyte et al., "Enhancer decommissioning by LSD1 during embryonic stem cell differentiation," Nature, 482(7384):221-225, Feb. 1, 2012.
Widschwendter and Jones, "DNA methylation and breast carcinogenesis," Oncogene, Aug. 2002, 21:5462-82.
Wong et al., "Detection of aberrant p16 methylation in the plasma and serum of liver cancer patients," Cancer Res., 59(1):71-73 Jan. 1, 1999.
Wood et al., "Targeted Genome Editing Across Species Using ZFNs and TALENs," Science, 333:307 (2011).
Wright et al., "Standardized reagents and protocols for engineering zinc finger nucleases by modular assembly," Nat Protoc., 2006, 1(3):1637-1652.
Wu et al., "Building zinc fingers by selection: toward a therapeutic application," Proc Natl Acad Sci U S A., 92(2):344-348, Jan. 17, 1995.
Wu et al., "Custom-designed zinc finger nucleases: what is next?" Cell Mol Life Sci., 64(22):2933-2944, Nov. 2007.
Wu, "The 5' ends of *Drosophila* heat shock genes in chromatin are hypersensitive to DNase I," Nature, 286(5776):854-860, Aug. 28, 1980.
Xie et al., "DNA hypomethylation within specific transposable element families associates with tissue-specific enhancer landscape," Nat Genet., 45(7):836-841, Epub May 26, 2013.
Xu et al., "Pioneer factor interactions and unmethylated CpG dinucleotides mark silent tissue-specific enhancers in embryonic stem cells," Proc Natl Acad Sci U S A., 104(30):12377-12382, Epub Jul. 18, 2007.
Xu et al., "Cytosine methylation targetted to pre-determined sequences," Nat Genet., Dec. 1997;17(4):376-8.
Xu et al., "Genome-wide regulation of 5hmC, 5mC, and gene expression by Tet1 hydroxylase in mouse embryonic stem cells," Mol Cell., 42(4):451-464, Epub Apr. 21, 2011.
Yang et al., "Os8N3 is a host disease-susceptibility gene for bacterial blight of rice," Proc Natl Acad Sci USA, Jul. 5, 2006;103(27):10503-8.
Yeager, "Genome Editing in a FLASH ," BioTechniques, Apr. 4, 2012, 2 pages, http://www.biotechniques.com/news/Genome-Editing-in-a-FLASH/biotechniques-329367.html.
Yoon and Brem, "Noncanonical transcript forms in yeast and their regulation during environmental stress," RNA, 16(6):1256-1267, Epub Apr. 26, 2010.
Yost et al., "Targets in epigenetics: inhibiting the methyl writers of the histone code," Curr Chem Genomics, 5(Suppl 1):72-84, Epub Aug. 22, 2011.
Zheng S et al., "Correlations of partial and extensive methylation at the P14ARF locus with reduced MRNA expression in colorectal cancer cell lines and clinicopathological features in primary tumors," Carcinogenesis, Nov. 1, 2000, 21(11): 2057-2064.
Zhang et al., "Efficient construction of sequence-specific TAL effectors for modulating mammalian transcription," Nat Biotechnol., 29(2):149-153, Epub Jan. 19, 2011.
Zhang et al., "Genome-wide identification of regulatory DNA elements and protein-binding footprints using signatures of open chromatin in *Arabidopsis*," Plant Cell., 24(7):2719-2731. Epub.Jul. 5, 2012.
Zhang et al., "Supplementary Information, Data S1, TET1 is a 5mC hydroxylase in vitro" from, "TET1 is a DNA-binding protein that modulates DNA methylation and gene transcription via hydroxylation of 5-methylcytosine," Cell Res., 6 pages, 2010.
Zhang et al., "Transcription activator-like effector nucleases enable efficient plant genome engineering," Plant Physiol., 161(1):20-27, Epub Nov. 2, 2012.
Zhang et al., "TET1 is a DNA-binding protein that modulates DNA methylation and gene transcription via hydroxylation of 5-methylcytosine," Cell Res., 20(12):1390-1393, Epub Nov. 16, 2010.
Zhang et al., "Programmable Sequence-Specific Transcriptional Regulation of mammilian Genome Using Designer TAL Effectors," Nature Biotechnology, Feb. 2011, 29(2): 149-153.
Zitzewitz et al., "Probing the folding mechanism of a leucine zipper peptide by stopped-flA4:A48ism spectroscopy," Biochemistry, 34(39):12812-12819, Oct. 3, 1995.
U.S. Non-Final Office Action in U.S. Appl. No. 14/232,067, dated Nov. 17, 2015, 10 pages.
U.S. Non-Final Office Action in U.S. Appl. No. 13/838,520, dated Oct. 6, 2014, 38 pages.
U.S. Final Office Action in U.S. Appl. No. 13/838,520, dated Jul. 15, 2015, 35 pages.
Japanese Office Action in Japanese Application No. 2014-520317, dated Apr. 5, 2016, 8 pages (with English translation).
Australian Office Action in Australian Application No. 2012284365, dated Jul. 29, 2016, 5 pages.
Entry for CDKN2A, cyclin-dependent kinase inhibitor 2A [*Homo sapiens* (human)], Gene ID: 1029, updated on Oct. 31, 2016, and printed from http:www.ncbi.nlm.nih.gov/gene/1029 as pp. 1/9 on Nov. 1, 2016.
Perez-Quintero et al., "An Improved Method for TAL Effectors DNA-Binding Sites Prediction Reveals Functional Convergence in TAL Repertoires of Xanthomonas oryzae Strains," Jul. 2013, PLOS ONE, 8.
Office Action in U.S. Appl. No. 14/435,065, dated Jan. 26, 2017, 22 pages.
Office Action in U.S. Appl. No. 14/766,713, dated Jan. 26, 2017, 39 pages.
Office Action in Japanese Appliaction No. 2014-520317, dated Jan. 17, 2017, 6 pages (with English translation).
Office Action in U.S. Appl. No. 13/838,520, dated Feb. 24, 2017, 49 pages.
Office Action in European Application No. 12814750.1, dated Mar. 8, 2017, 7 pages.
Office Action in U.S. Appl. No. 14/766,713, dated Jul. 25, 2017, 23 pages.
Sera et al. Zinc-finger-based artificial transcription factors and their applications. Advanced Drug Delivery Reviews, vol. 61, pp. 513-526, Apr. 2009.
Pekowska et al. H3K4 tri-methylation provides an epigenetic signature of active enhancers. The EMBO Journal, vol. 30, pp. 4198-4210, Aug. 16, 2011, including supplementary figures S1-S11, printed as pp. 1/13-13/13.
Li et al. Regulatory mechanisms of tumor suppressor p16AINK4A and their relevance to cancer. Biochemistry, vol. 50, pp. 5566-5582, May 27, 2011.
European Office Action in European Application No. 13797024.0, dated Jul. 18, 2017, 9 pages.
Frauer et al., "Different Binding Properties and Function of CXXC Zinc Finger Domains in Dnmt1 and Tet1," PLOS One, Feb. 2011, 6: e16627.
Office Action in U.S. Appl. No. 14/435,065, dated Jul. 27, 2017, 25 pages.
Office Action in Japanese Application No. 2015-557129, dated Dec. 19, 2017, 8 pages (with English translation).
Maeder et al, "Upregulation of the Pluripotency-Associated miRNA 302-367 Cluster 1 Using Engineered Transcription Activator-Like Effector(TALE) Activators," Molecular Therapy, 2012, 20: S193 499.
Office Action in European Application No. 13845212.3, dated Feb. 15, 2018, 4 pages.
Extended European Search Report in Application No. 17205413.2, dated Mar. 23, 2018, 7 pages.
European Office Action in Application No. 13797024.0, dated Mar. 16, 2018, 8 pages.
Jia et al., "Cancer gene therapy targeting cellular apoptosis machinery," Cancer Treatment Reviews, 2012, 38: 868-879.
Verma and Weitzman, "Gene Therapy: Twenty-first century medicine," Annual Review of Biochemistry, 2005, 74: 711-738.

(56) References Cited

OTHER PUBLICATIONS

Yan et al., "Drugging the undruggable: Transcription therapy for cancer," Biochinnica et Biophysica Acta, 2013, 1835: 76-85.
Tani et al., "Updates on current advances in gene therapy," The West Indian Medical Journal, Mar. 2011, 60: 188-194.
Arora et al., "Residues 1-254 of anthrax toxin lethal factor are sufficient to cause cellular uptake of fused polypeptides," J. Biol. Chem., Feb. 1993, 268:3334-41.
Aslanidis et al., "Ligation-independent cloning of PCR products (LIC-PCR)," Nucleic Acids Res., Oct. 1990, 18(20):6069-6074.
AU Office Action in Australian Application No. 2014214719, dated Feb. 14, 2019, 3 pages.
CA Office Action in Canadian Application No. 2,841,710, dated Apr. 15, 2019, 4 pages.
CA Office Action in Canadian Appln. No. 2,900,338, dated Dec. 16, 2019, 5 pages.
EP Extended European Search Report in EP Appln. No. 19191923.2, dated Feb. 14, 2020, 7 pages.
EP Extended European Search Report in European Application No. 18191841.8, dated May 24, 2019, 16 pages.
EP Extended European Search Report in European Application No. 18214166.3, dated Feb. 4, 2019, 9 pages.
EP Office Action in European Appln. No. 18191841.8, dated Apr. 17, 2020, 5 pages.
EP Partial European Search Report in European Application No. 18191841.8, dated Jan. 30, 2019, 17 pages.
European Office Action in European Application No. 13845212, dated May 18, 2016, 1 page.
Extended European Search Report in European Application No. 14749683, dated Sep. 9, 2016, 7 pages.
GenBank Accession No. FJ176909.1, "Xanthomonas oryzae pv. oryzae clone D41 avirulence/virulence factor repeat domain protein-like gene, complete sequence," Sep. 30, 2008, 2 pages.
Greer et al. Histone methylation: a dynamic mark in health, disease and inheritance. Nature Reviews Genetics, vol. 13, pp. 343-357, published, online Apr. 3, 2012. (Year: 2012).
International Preliminary Report on Patentability in International Application No. PCT/US2012/046451, dated Jan. 21, 2014, 6 pages.
International Preliminary Report on Patentability in International Application No. PCT/US2013/043075, dated Dec. 2, 2014, 7 pages.
International Preliminary Report on Patentability in International Application No. PCT/US2013/064511, 12 pages, dated Apr. 14, 2015.
International Preliminary Report on Patentability in International Application No. PCT/US2014/015343, 7 pages, dated Aug. 11, 2015.
International Search Report and Written Opinion in International Application No. PCT/US2012/046451, dated Nov. 15, 2012, 8 pages.
International Search Report and Written Opinion in International Application No. PCT/US2013/043075, dated Sep. 26, 2013, 10 pages.
International Search Report and Written Opinion in International Application No. PCT/US2013/064511, dated Jan. 30, 2014, 8 pages.
International Search Report and Written Opinion in International Application No. PCT/US2014/015343, dated Jun. 3, 2014, 17 pages.
JP Office Action in Japanese Application No. 2017-136828, dated Aug. 27, 2019, 7 pages (with English Translation).
JP Office Action in Japanese Application No. 2018-223519, dated Jan. 7, 2020, 7 pages (with English Translation).
JP Office Action in Japanese Appln. No. 2019-043522, dated Mar. 3, 2020, 8 pages (with English translation).
Kamijo et al. Tumor spectrum in ARF-deficient mice. Cancer Research, vol. 59, pp. 2217-2222, May 1999. (Year: 1999).
Kim et al., "Genome editing with modularly assembled zinc-finger nucleases " Nat. Methods, 7(2):91-92, Feb. 2010.
Kondo et al., "Epigenetic changes in colorectal cancer," Cancer Metastasis Reviews, Jan. 2004, 23(1-2):29-39.
Mendenhall et al., "Identification of promoter targets of enhancers by epigenetic knockdown using TAL DNA binding proteins," Epigenetics & Chromatin, 2013, 6(Suppl): 1-2.
Mussolino and Cathomen, "TALE nucleases: tailored genome engineering made easy," Curr Opin Biotechnol., 23(5):644-650, Epub Feb. 17, 2012.
UCSC Genome Browser (Human Feb. 2009 (GRCh37/hg19) Assembly, chr12:2,162,284-2,162,418 with HEK293T DNase 1 HS track from ENCODE/DUKE, printed from https://genome.ucwsc.edu as p. 1/1 on Jun. 28, 2019. (Year: 2019).
UCSC Genome Browser (Human Feb. 2009 (GRCh37/hg19) Assembly, chr9:21,440,329-21,440,478 with HEK293T DNase 1 HS track from ENCODE/DUKE, printed from https://genome.ucwsc.edu as p. 1/1 on Jun. 25, 2019. (Year: 2019).
Branco et al., "Uncovering the role of 5-hydroxymethylcytosine in the epigenome," Nature Reviews Genetics, Nov. 15, 2011, 13:7-13.
EP Extended European Search Report in European Application No. 20183740.8, dated Nov. 4, 2020, 15 pages.

```
5'-GGGGGCGGGCGGAGCCTTGgggtcaccaagagccactgaa
3'-CCCCCGCCCGCCTCGGAACcccagtggttctcggtgactt cgagggtaaggagcggccaccgcgcggactccgcaacctt
   gctcccattcctcgccggtggcgcgctgaggcgttggaa
                                            1
   cccgggatagcttccgtgtccttggctcagctgtgtatgc
   gggccctatcgaaggcacaggaaccgagtcgacatacg ccgtggtgcgagcactgcggagccgctggggcgcaagcc
   ggcaccacgctcgtgacgcctcggcggacccgcgttcgg 2
   gggtcttccagtccccgggcgcgctgtcggtagggcgg
   cccagaagtggtcaggggcccgcgcagccatcccgcc gcgctctcgggccaccgggcgggaggtggccgcgtcccca
   cgcgagagcccggtggccgcctccaccggcgcagggt gacactggctgggccagagtgagtttagcGCGTAGGCGGC- 3'
   ctgtgaccgacccggtctcactcaaatcgCGCATCCGCG- 5'
                 3
              4
```

FIG. 2

Tet1-FL
MSRSRHARPSRLVRKEDVNKKKKNSQLRKTTKGANKNVASVKTLSPGKLKQLIQERDVKKKTEP
KPPVPVRSLLTRAGAARMNLDRTEVLFQNPESLTCNGFTMALRSTSLSRRLSQPPLVVAKSKKV
PLSKGLEKQHDCDYKILPALGVKHSENDSVPMQDTQVLPDIETLIGVQNPSLLKGKSQETTQFW
SQRVEDSKINIPTHSGPAAEILPGPLEGTRCGEGLFSEETLNDTSGSPKMFAQDTVCAPFPQRA
TPKVTSQGNPSIQLEELGSRVESLKLSDSYLDPIKSEHDCYPTSSLNKVIPDLNLRNCLALGGS
TSPTSVIKFLLAGSKQATLGAKPDHQEAFEATANQQEVSDTTSFLGQAFGAIPHQWELPGADPV
HGEALGETPDLPEIPGAIPVQGEVFGTILDQQETLGMSGSVVPDLPVFLPVPPNPIATFNAPSK
WPEPQSTVSYGLAVQGAIQILPLGSGHTPQSSSNSEKNSLPPVMAISNVENEKQVHISFLPANT
QGFPLAPERGLFHASLGIAQLSQAGPSKSDRGSSQVSVTSTVHVVNTTVVTMPVPMVSTSSSSY
TTLLPTLEKKKRKRCGVCEPCQQKTNCGECTYCKNRKNSHQICKKRKCEELKKKPSVVVPLEVI
KENKRPQREKKPKVLKADFDNKPVNGPKSESMDYSRCGHGEEQKLELNPHTVENVTKNEDSMTG
IEVEKWTQNKKSQLTDHVKGDFSANVPEAEKSKNSEVDKKRTKSPKLFVQTVRNGIKHVHCLPA
ETNVSFKKFNIEEFGKTLENNSYKFLKDTANHKNAMSSVATDMSCDHLKGRSNVLVFQQPGFNC
SSIPHSSHSIINHHASIHNEGDQPKTPENIPSKEPKDGSPVQPSLLSLMKDRRLTLEQVVAIEA
LTQLSEAPSENSSPSKSEKDEESEQRTASLLNSCKAILYTVRKDLQDPNLQGEPPKLNHCPSLE
KQSSCNTVVFNGQTTTLSNSHINSATNQASTKSHEYSKVTNSLSLFIPKSNSSKIDTNKSIAQG
IITLDNCSNDLHQLPPRNNEVEYCNQLLDSSKKLDSDDLSCQDATHTQIEEDVATQLTQLASII
KINYIKPEDKKVESTPTSLVTCNVQQKYNQEKGTMQQKPPSSVHNNHGSSLTKQKNPTQKKTKS
TPSRDRRKKKPTVVSYQENDRQKWEKLSYMYGTICDIWIASKFQNFGQFCPHDFPTVFGKISSS
TKIWKPLAQTRSIMQPKTVFPPLTQIKLQRYPESAEEKVKVEPLDSLSLFHLKTESNGKAFTDK
AYNSQVQLTVNANQKAHPLTQPSSPPNQCANVMAGDDQIRFQQVKEQLMHQRLPTLPGISHET
PLPESALTLRNVNVVCSGGITVVSTKSEEEVCSSSFGTSEFSTVDSAQKNFNDYAMNFFTNPTK
NLVSITKDSELPTCSCLDRVIQKDKGPYYTHLGAGPSVAAVREIMENRYGQKGNAIRIEIVVYT
GKEGKSSHGCPIAKWVLRRSSDEEKVLCLVRQRTGHHCPTAVMVVLIMVWDGIPLPMADRLYTE
LTENLKSYNGHPTDRRCTLNENRTCTCQGIDPETCGASFSFGCSWSMYFNGCKFGRSPSPRRFR
IDPSSPLHEKNLEDNLQSLATRLAPIYKQYAPVAYQNQVEYENVARECRLGSKEGRPFSGVTAC
LDFCAHPHRDIHNMNNGSTVVCTLTREDNRSLGVIPQDEQLHVLPLYKLSDTDEFGSKEGMEAK
IKSGAIEVLAPRRKKRTCFTQPVPRSGKKRAAMMTEVLAHKIRAVEKKPIPRIKRKNNSTTTNN
SKPSSLPTGSNTETVQPEVKSETEPHFILKSSDNTKTYSLMPSAPHPVKEASPGFSWSPKTAS
ATPAPLKNDATASCGFSERSSTPHCTMPSGRLSGANAAAADGPGISQLGEVAPLPTLSAPVMEP
LINSEPSTGVTEPLTPHQPNHQPSFLTSPQDLASSPMEEDEQHSEADEPPSDEPLSDDPLSPAE
EKLPHIDEYWSDSEHIFLDANIGGVAIAPAHGSVLIECARRELHATTPVEHPNRNHPTRLSLVF
YQHKNLNKPQHGFELNKIKFEAKEAKNKKMKASEQKDQAANEGPEQSSEVNELNQIPSHKALTL
THDNVVTVSPYALTHVAGPYNHWV

FIG. 5A

Tet1-NZ
EELKKKPSVVVPLEVIKENKRPQREKKPKVLKADFDNKPVNGPKSESMDYSRCGHGEEQKLELN
PHTVENVTKNEDSMTGIEVEKWTQNKKSQLTDHVKGDFSANVPEAEKSKNSEVDKKRTKSPKLF
VQTVRNGIKHVHCLPAETNVSFKKFNIEEFGKTLENNSYKFLKDTANHKNAMSSVATDMSCDHL
KGRSNVLVFQQPGFNCSSIPHSSHSIINHHASIHNEGDQPKTPENIPSKEPKDGSPVQPSLLSL
MKDRRLTLEQVVAIEALTQLSEAPSENSSPSKSEKDEESEQRTASLLNSCKAILYTVRKDLQDP
NLQGEPPKLNHCPSLEKQSSCNTVVFNGQTTTLSNSHINSATNQASTKSHEYSKVTNSLSLFIP
KSNSSKIDTNKSIAQGIITLDNCSNDLHQLPPRNNEVEYCNQLLDSSKKLDSDDLSCQDATHTQ
IEEDVATQLTQLASIIKINYIKPEDKKVESTPTSLVTCNVQQKYNQEKGTMQQKPPSSVHNNHG
SSLTKQKNPTQKKTKSTPSRDRRKKKPTVVSYQENDRQKWEKLSYMYGTICDIWIASKFQNFGQ
FCPHDFPTVFGKISSSTKIWKPLAQTRSIMQPKTVFPPLTQIKLQRYPESAEEKVKVEPLDSLS
LFHLKTESNGKAFTDKAYNSQVQLTVNANQKAHPLTQPSSPPNQCANVMAGDDQIRFQQVVKEQ
LMHQRLPTLPGISHETPLPESALTLRNVNVVCSGGITVVSTKSEEEVCSSSFGTSEFSTVDSAQ
KNFNDYAMNFFTNPTKNLVSITKDSELPTCSCLDRVIQKDKGPYYTHLGAGPSVAAVREIMENR
YGQKGNAIRIEIVVYTGKEGKSSHGCPIAKWVLRRSSDEEKVLCLVRQRTGHHCPTAVMVVLIM
VWDGIPLPMADRLYTELTENLKSYNGHPTDRRCTLNENRTCTCQGIDPETCGASFSFGCSWSMY
FNGCKFGRSPSPRRFRIDPSSPLHEKNLEDNLQSLATRLAPIYKQYAPVAYQNQVEYENVAREC
RLGSKEGRPFSGVTACLDFCAHPHRDIHNMNNGSTVVCTLTREDNRSLGVIPDEQLHVLPLYK
LSDTDEFGSKEGMEAKIKSGAIEVLAPRRKKRTCFTQPVPRSGKKRAAMMTEVLAHKIRAVEKK
PIPRIKRKNNSTTTNNSKPSSLPTLGSNTETVQPEVKSETEPHFILKSSDNTKTYSLMPSAPHP
VKEASPGFSWSPKTASATPAPLKNDATASCGFSERSSTPHCTMPSGRLSGANAAAADGPGISQL
GEVAPLPTLSAPVMEPLINSEPSTGVTEPLTPHQPNHQPSFLTSPQDLASSPMEEDEQHSEADE
PPSDEPLSDDPLSPAEEKLPHIDEYWSDSEHIFLDANIGGVAIAPAHGSVLIECARRELHATTP
VEHPNRNHPTRLSLVFYQHKNLNKPQHGFELNKIKFEAKEAKNKKMKASEQKDQAANEGPEQSS
EVNELNQIPSHKALTLTHDNVVTVSPYALTHVAGPYNHWV

FIG. 5B

Tet1-CD
LPTCSCLDRVIQKDKGPYYTHLGAGPSVAAVREIMENRYGQKGNAIRIEIVVYTGKEGKSSHGC
PIAKWVLRRSSDEEKVLCLVRQRTGHHCPTAVMVVLIMVWDGIPLPMADRLYTELTENLKSYNG
HPTDRRCTLNENRTCTCQGIDPETCGASFSFGCSWSMYFNGCKFGRSPSPRRFRIDPSSPLHEK
NLEDNLQSLATRLAPIYKQYAPVAYQNQVEYENVARECRLGSKEGRPFSGVTACLDFCAHPHRD
IHNMNNGSTVVCTLTREDNRSLGVIPDEQLHVLPLYKLSDTDEFGSKEGMEAKIKSGAIEVLA
PRRKKRTCFTQPVPRSGKKRAAMMTEVLAHKIRAVEKKPIPRIKRKNNSTTTNNSKPSSLPTLG
SNTETVQPEVKSETEPHFILKSSDNTKTYSLMPSAPHPVKEASPGFSWSPKTASATPAPLKNDA
TASCGFSERSSTPHCTMPSGRLSGANAAAADGPGISQLGEVAPLPTLSAPVMEPLINSEPSTGV
TEPLTPHQPNHQPSFLTSPQDLASSPMEEDEQHSEADEPPSDEPLSDDPLSPAEEKLPHIDEYW
SDSEHIFLDANIGGVAIAPAHGSVLIECARRELHATTPVEHPNRNHPTRLSLVFYQHKNLNKPQ
HGFELNKIKFEAKEAKNKKMKASEQKDQAANEGPEQSSEVNELNQIPSHKALTLTHDNVVTVSP
YALTHVAGPYNHWV

| Disease /condition | Gene | Reference |
|---|---|---|
| Cancer | | |
| Bladder | Multiple genes | 1 |
| Brain (glioma) | RASSFIA | 2, 3 |
| Brain (glioblastoma) | MGMT | 4 |
| Breast | BRCA1 | 5 |
| Breast | Multiple genes | 6, 7 |
| Cervix | P16 | 8 |
| Colon | Multiple genes | 1 |
| Esophagus | CDH1 | 1 |
| Head & neck | pf6, MGMT | 1 |
| Kidney | TIMP-3 | 1 |
| Leukemia | p15 | 1 |
| Liver | Multiple genes | 9 |
| Lung | pl6, p73 | 1 |
| Lymphoma | DAPK | 1 |
| Myeloma | DAPK | 10 |
| Ovary | BRCA1 | 11 |
| Pancreas | APC | 1 |
| Prostate | BRCA2 | 1, 12 |
| Rhabdomyosarcoma | PAX3 | 13 |
| Uterus | hMLHI | 1 |
| Neurologic | | |
| Schizophrenia | RELN | 14, 15 |
| Cardiovascular | | |
| Atherosclerosis | Multiple genes | 16 |

TAL-TET1 FUSION PROTEINS AND METHODS OF USE THEREOF

CLAIM OF PRIORITY

This application is a divisional of U.S. patent application Ser. No. 13/838,520, filed Mar. 15, 2013, which claims priority under 35 USC § 119(e) to U.S. Patent Application Ser. No. 61/652,711, filed on May 29, 2012, the entire contents of which are hereby incorporated by reference.

FEDERALLY SPONSORED RESEARCH OR DEVELOPMENT

This invention was made with Government support under Grant No. DP1 OD006862 awarded by the National Institutes of Health. The Government has certain rights in the invention.

The Sequence Listing associated with this application is filed in electronic format via EFS-Web and is hereby incorporated by reference into the specification in its entirety. The name of the text file containing the Sequence Listing is SL.txt. The size of the text file is 37.4 KB, and the text file was created on Feb. 12, 2018.

TECHNICAL FIELD

This invention relates to fusion proteins comprising a DNA binding domain, e.g., a TAL effector repeat array-Tet1 (TAL-Tet1) or zinc finger, and a catalytic domain comprising a sequence that catalyzes hydroxylation of methylated cytosines in DNA, and methods of use thereof.

BACKGROUND

Tet1 is an enzyme that catalyzes the conversion of 5-methylcytosine (5mC) to 5-hydroxymethylcytosine (5hmC) (Tahiliani, M. et al. Science 324, 930-935 (2009)). While the role of 5hmC is not entirely clear, it has been proposed that it may be an intermediate in the process of demethylation of 5-methylcytosine to cytosine. This is supported by evidence that overexpression of Tet1 in cultured cells leads to an overall decrease in levels of 5mC (Tahiliani, M. et al. Science 324, 930-935 (2009)). Several mechanisms of demethylation have been proposed. There is evidence that 5hmC can be deaminated and that the resulting mismatched base is recognized by DNA glycosylases and subsequently repaired to cytosine via the base excision repair pathway (Guo et al., Cell 145, 423-434 (2011)). Alternatively, there is also evidence that iterative oxidation of 5hmC by Tet1 yields 5-formylcytosine (fC) and 5-carboxylcytosine (caC), which can then be recognized by thymine DNA glycosylase and reverted to cytosine through base excision repair (He et al., Science 333, 1303-1307 (2011)). In either case, all evidence highlights Tet1 as a primary catalyst for DNA demethylation.

SUMMARY

At least in part, the present invention is based on the discovery of fusion proteins comprised of an engineered custom DNA-binding domain fused to a protein capable of catalyzing hydroxylation of methylated cytosines in DNA in vitro, in cells, or in whole organisms. Such a hybrid protein would lead to formation of hydroxymethylated cytosines from methylated cytosines in DNA and subsequent demethylation of the cytosines in living cells or organisms.

Thus provided herein are fusion proteins comprising an engineered DNA-binding domain that binds specifically to a preselected target sequence, and a catalytic domain comprising a sequence that catalyzes demethylation of cytosines in DNA. In some embodiments, the fusion proteins further comprise a linker between the DNA binding domain and the catalytic domain.

In some embodiments, the DNA-binding domain is or comprises an engineered transcription activator-like (TAL) effector repeat array or a zinc finger.

In some embodiments, the catalytic domain comprises a catalytic domain of Tet1, Tet2, or Tet3. In some embodiments, the catalytic domain comprises amino acids 1580-2052 of Tet1, amino acids 1290-1905 of Tet2, amino acids 966-1678 of Tet3, amino acids 1418-2136 of Tet1, amino acids 1-2136 of Tet1, or amino acids 1-584 and 625-2136 of Tet1.

In some embodiments, the fusion proteins comprise a plurality of catalytic domains.

In a further aspect, the invention provides methods for reducing methylation of a selected DNA sequence in a mammalian cell, the method comprising contacting the cell with a fusion protein comprising an engineered DNA-binding domain that binds specifically to a target sequence, wherein the target sequence is within about 10 kb, 5 kb, 2 kb, or 1 kb, 500 bp, 250 bp, 100 bp, 50 bp, 40 bp, 30 bp, or 20 bp, of the selected DNA sequence, and a catalytic domain comprising a sequence that catalyzes hydroxylation of methylated cytosines in DNA.

In another aspect, the invention provides methods for reducing methylation of a selected DNA sequence in a mammalian cell, the method comprising contacting the cell with a nucleic acid encoding a fusion protein comprising an engineered DNA-binding domain that binds specifically to a target sequence, wherein the target sequence is within about 10 kb, 5 kb, 2 kb, 1 kb, 500 bp, 250 bp, 100 bp, 50 bp, 40 bp, 30 bp, or 20 bp, of the selected DNA sequence, and a catalytic domain comprising a sequence that catalyzes hydroxylation of methylated cytosines in DNA.

In some embodiments, the fusion protein further comprises a linker between the DNA binding domain and the catalytic domain.

In some embodiments, the DNA-binding domain is or comprises an engineered transcription activator-like (TAL) effector repeat array or a zinc finger.

In some embodiments, the catalytic domain comprises a catalytic domain of Tet1, e.g., amino acids 1418-2136 of Tet1.

In some embodiments, the cell is a human cell.

In some embodiments, the cell is in a living mammal.

In some embodiments, the selected DNA sequence is a sequence of a gene listed in FIG. 7.

In some embodiments, the gene is selected from the group consisting of RASSF1A, MGMT, BRCA1, p16, CDH1, TIMP-3, p15, p'73, DAPK, APC, and RELN.

In some embodiments, the cell is present in an individual diagnosed with a disease listed in FIG. 7, and the selected DNA sequence is a gene associated with that disease as listed in FIG. 7.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

A) Schematic shows the predicted domain architecture of the Tet1 protein (Tet1-FL), the catalytic domain of the Tet1 protein (Tet1-CD) and the truncated version of Tet1 in which the CXXC domain has been removed (Tet1-NZ). Features shown include the CXXC-type zinc-binding domain (CXXC), three nuclear localization signals (NLS), the cysteine-rich region (cys-rich) and the double-stranded β helix domain (DSBH) (Tahiliani et al., *Science* 2009). B) Schematic shows an exemplary TAL-Tet1 fusion protein, in which Tet1 is fused to the C-terminal end of the TALE protein via a Gly$_3$Ser linker. In some embodiments, the Tet1 is fused to the N-terminal end. The engineered TALE protein binds DNA target sequence and thus localizes Tet1 protein to this region.

FIG. 2. TAL Arrays Targeted to Human Klf4. Sequence of human Klf4 intron 1-2 (SEQ ID NO:1). Intron sequences are shown in lowercase letters with neighboring exon sequences shown in uppercase letters. The four sites for which engineered customized TAL effector repeat array domains were generated are underlined and numbered.

Figure 3:
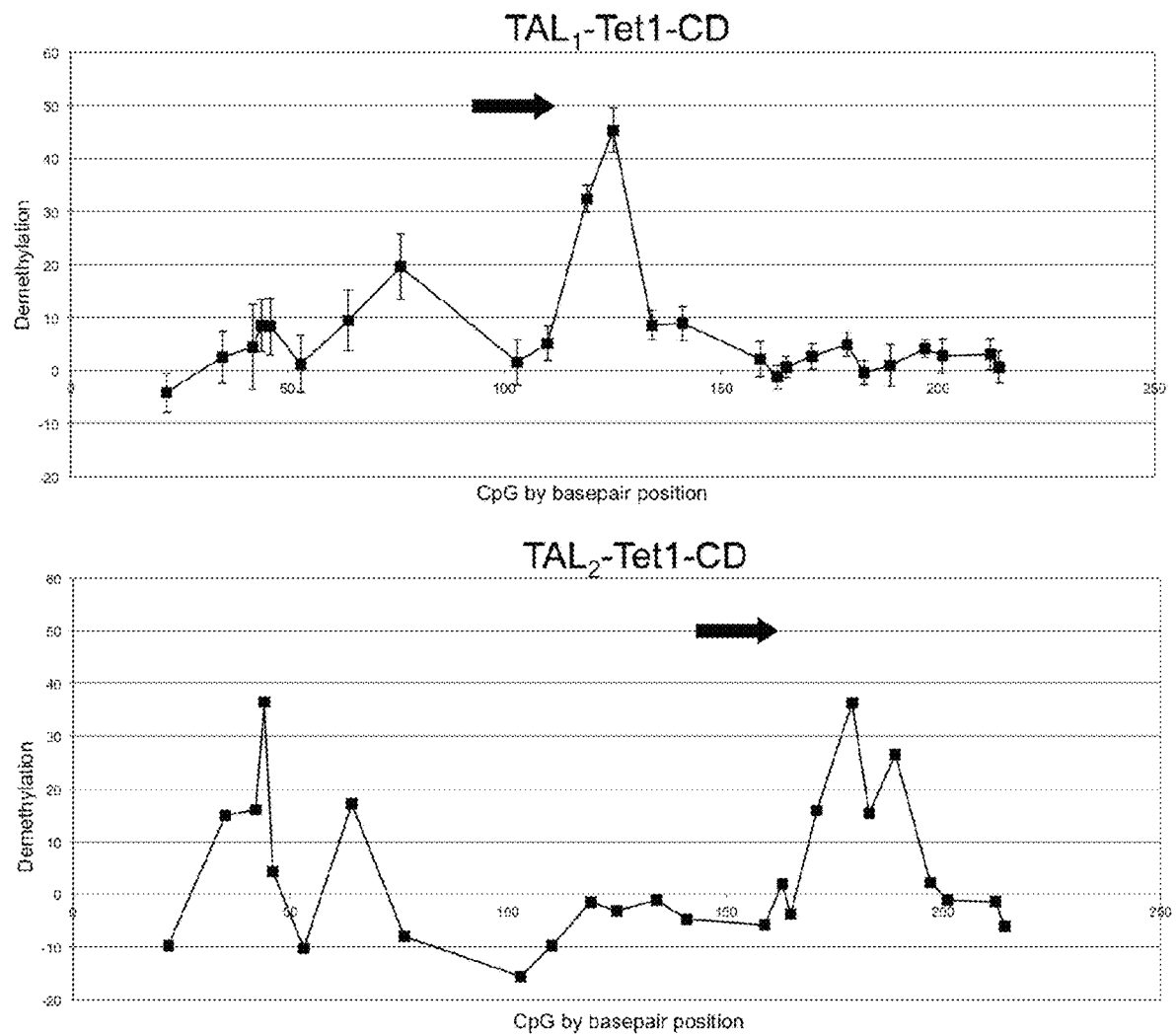
Figure 3:
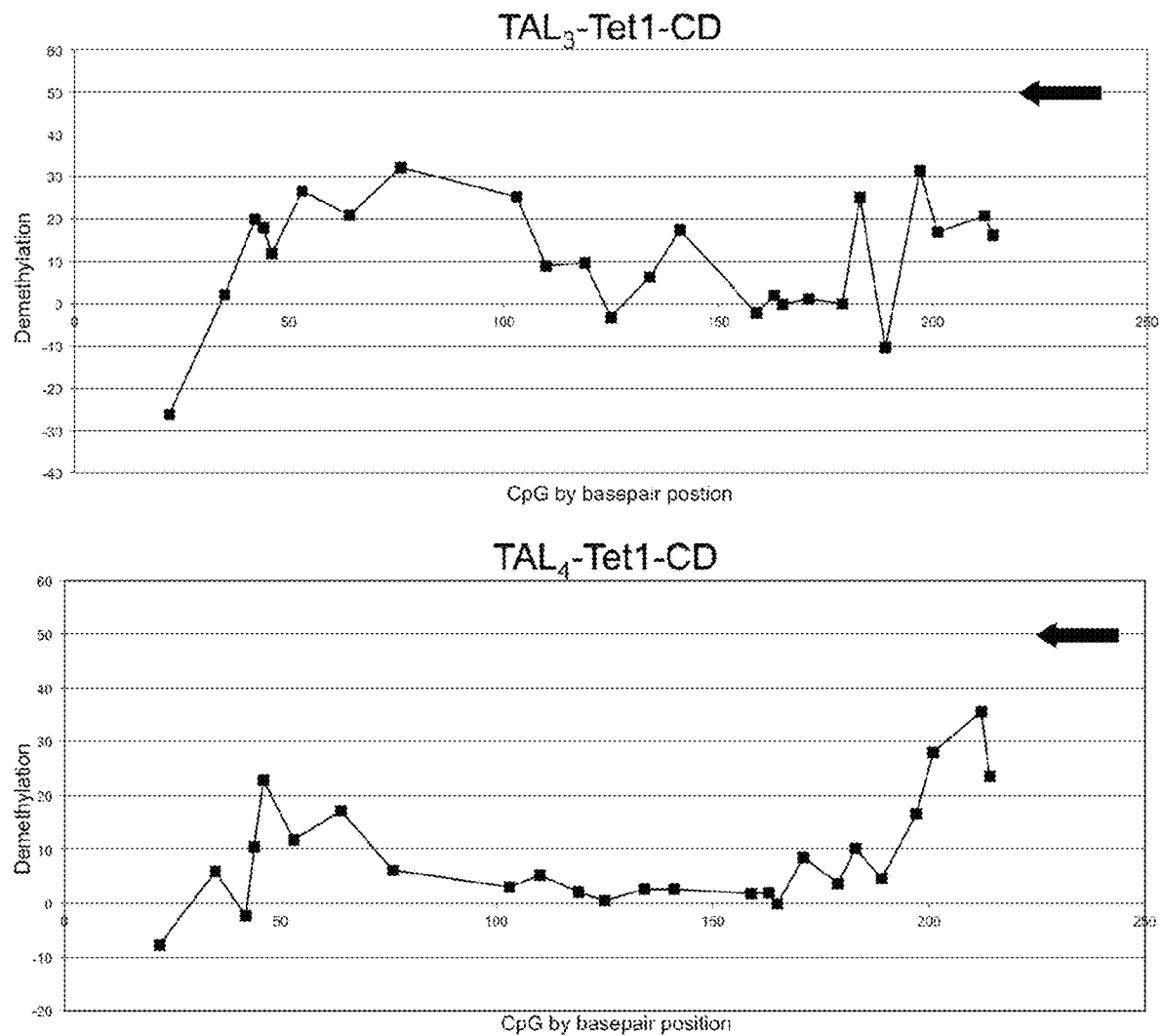

FIG. 3. Targeted demethylation at the human KLF4 gene by TAL-Tet1-CD fusion proteins harboring a Gly$_3$Ser (SEQ ID NO:5) linker. Graphs show demethylation observed upon transfection of 4 different TAL-Tet1-CD fusion proteins into human K562 cells. Demethylation is calculated for each CpG by subtracting the % unmethylated CpGs in mock-transfected or GFP-transfected cells from the % unmethylated CpGs in cells in which TAL-Tet1-CD protein was expressed. Position of the TAL binding site is depicted with an arrow and direction of the arrow indicates N-terminal to C-terminal orientation of the protein. The specific TAL effector binding site targeted is indicated by a subscript, with TAL referring to binding site #1, etc and corresponding to the numbering of sites shown in FIG. 2. Where possible, error bars were calculated by pooling the standard error from the mean of both experimental and control replicates.

Figure 4:
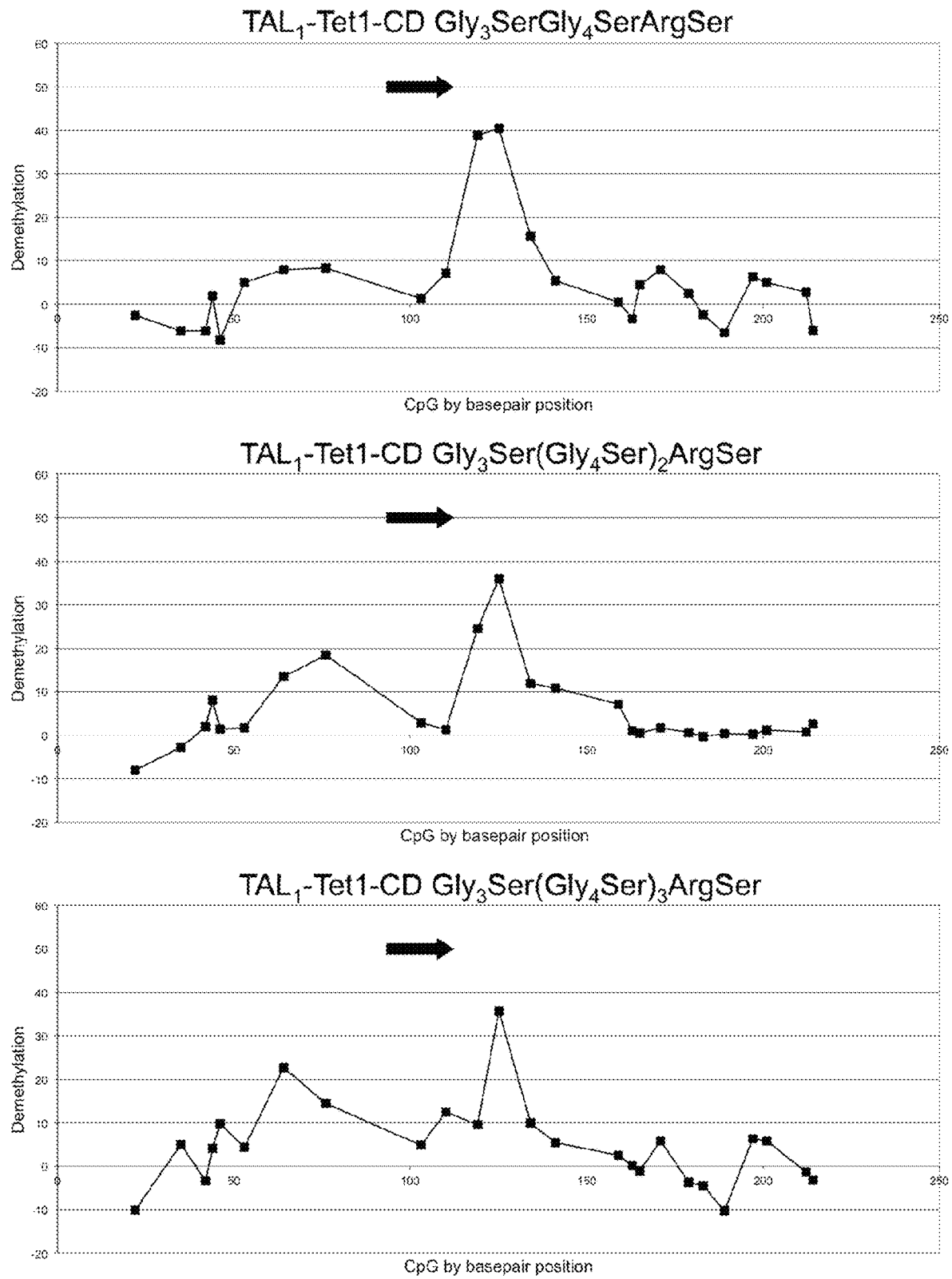
Figure 4:
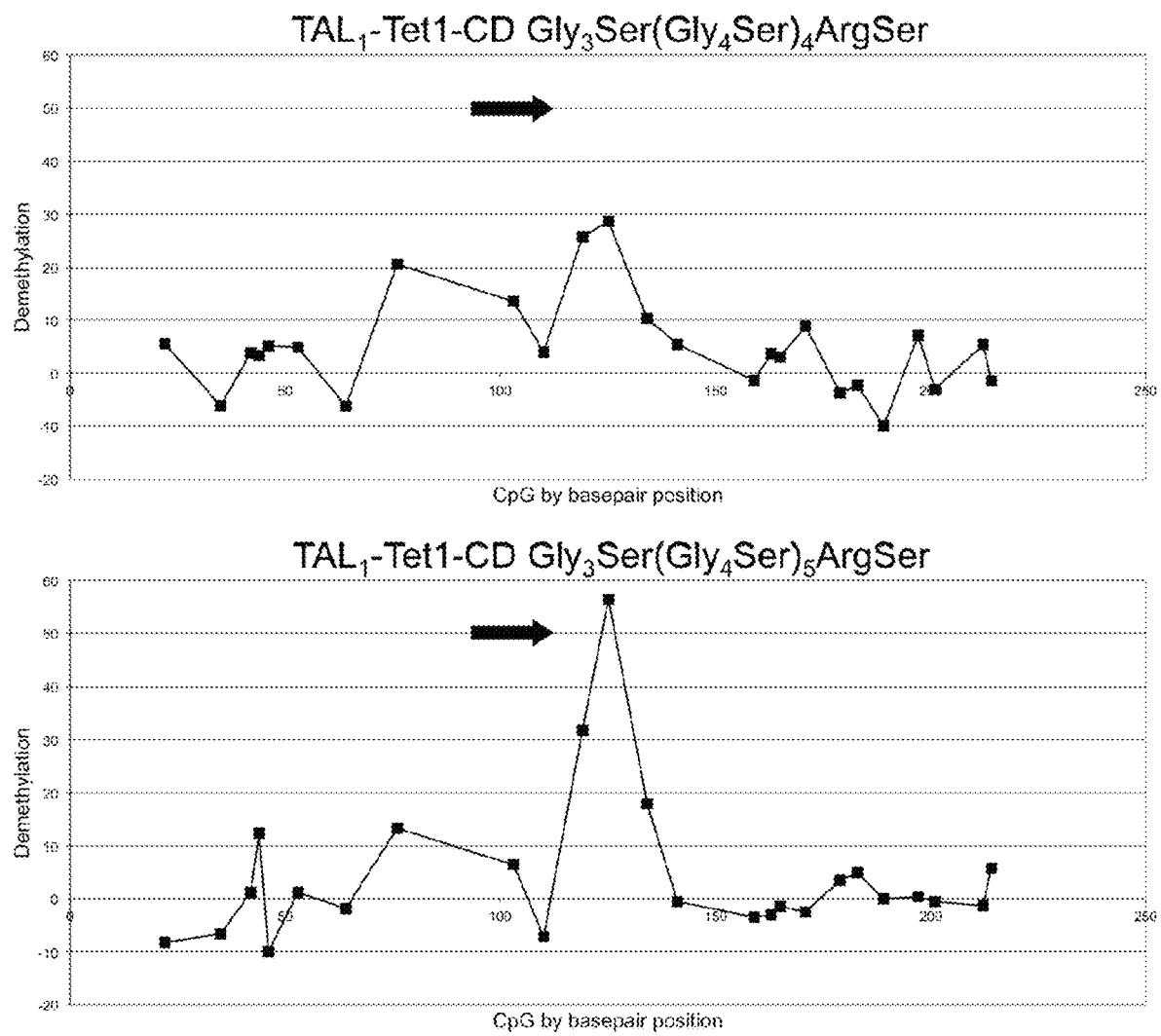
Figure 6A:
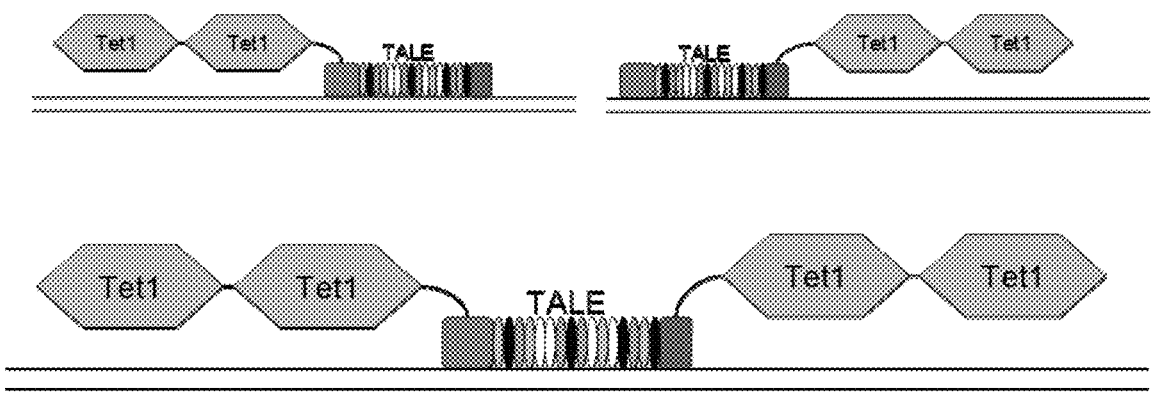
Figure 6B:
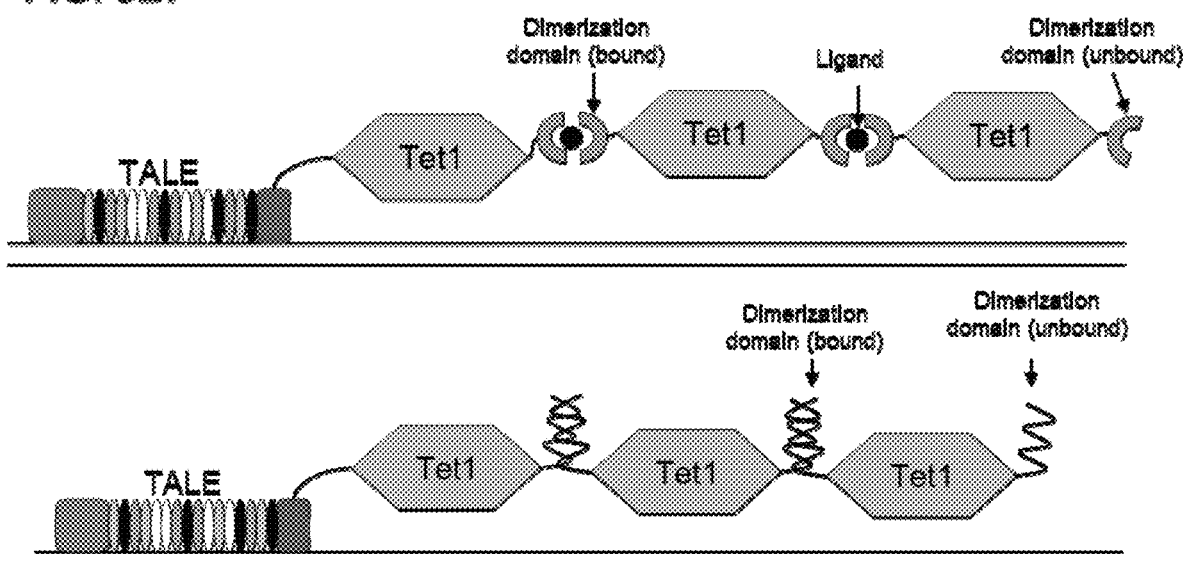
Figure 6C:
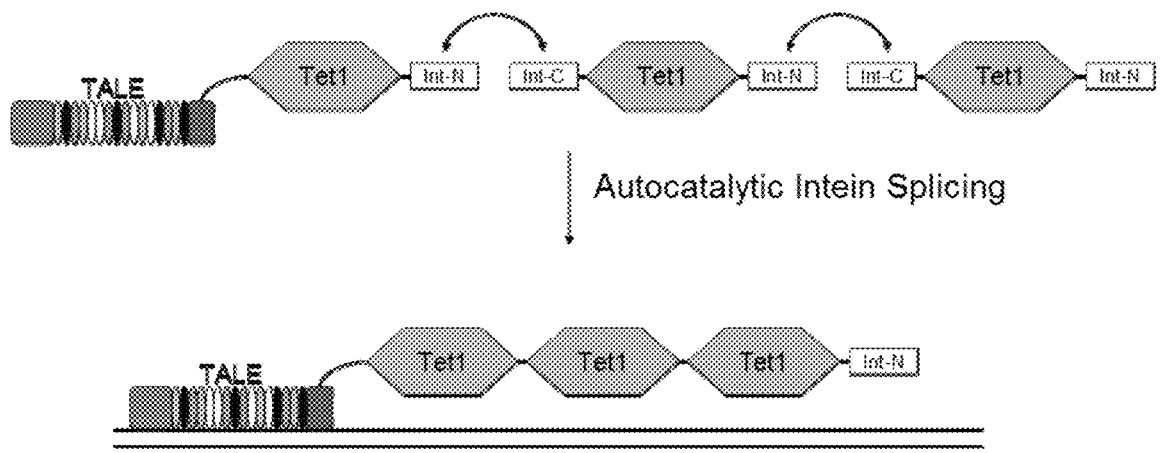
Figure 6D:
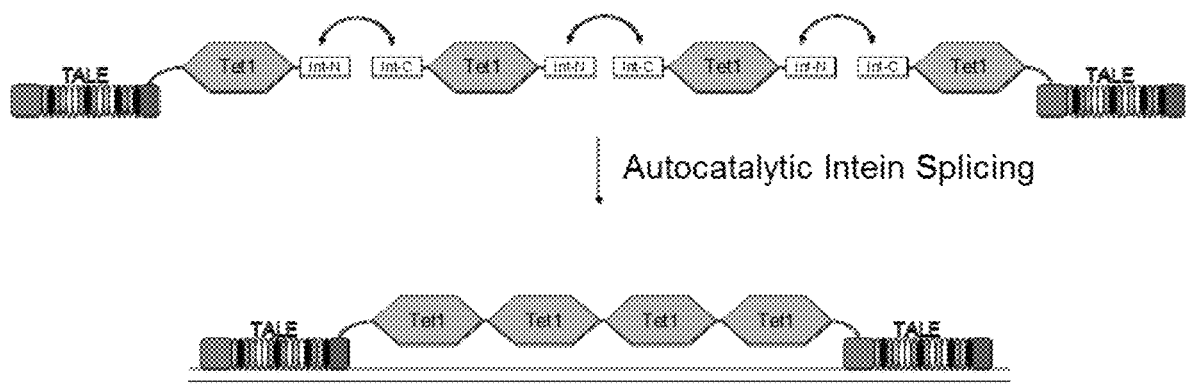

FIG. 4. Targeted demethylation at the human KLF4 gene using TAL-Tet1-CD fusion proteins harboring more extended linker variants. Graphs show demethylation observed upon transfection of 5 different TAL-Tet1-CD fusion proteins into human KS62 cells (graphs show SEQ ID NO:6, SEQ ID NO:7, SEQ ID NO:8, SEQ ID NO:9, SEQ ID NO:10). Each fusion uses the same TAL DNA binding domain and Tet1-CD, but differs in the length and amino acid sequence used as a linker between the two domains. Demethylation is calculated for each CpG by subtracting the % unmethylated CpGs in mock-transfected or GFP-transfected cells from the % unmethylated CpGs in cells in which TAL-Tet1-CD protein was expressed. Position of the TAL binding site is depicted with an arrow and direction of the arrow indicates N-terminal to C-terminal orientation of the protein.

FIGS. 5A-C. Amino acid sequences of full length Tet1 (Tet1-FL; 5A: SEQ ID NO: 2), Tet1 catalytic domain (Tet1-CD; 5C: SEQ ID NO: 4) and Tet1 protein with CXXC domain removed (Tet1-NZ; 5B: SEQ ID NO: 3).

FIGS. 6A-D. A set of schematic illustrations showing Strategies for Tet1 Multimerization. A) Simple fusion of multiple Tet1 domains to one TALE DNA binding domain in either amino-terminal orientation, carboxy-terminal orientation, or both. B) Non-covalent DNA interaction schemes, showing either ligand-dependent binding (inducible multimerization) or direct binding through protein-protein interacting domains. C) Covalent DNA interaction scheme showing split-inteins, here designated as Int-N on the amino-terminal protein and Int-C on the carboxy-terminal protein, before and after splicing. D) An example of the use of several multimerization approaches at once showing the use of both split-inteins as well as multimerization of Tet1 domains in either amino- or cabroxy-terminal orientation with respect to the TALE DNA binding protein.

FIG. 7. List of human diseases and conditions associated with hypermethylation. Adapted from Table 1 of Rodenhiser and Mann, CMAJ 174(3):341-348 (2006). The references noted in the table are as follows:

1. Esteller M, Corn P G, Baylin S B, et al. Cancer Res 2001; 61:3225-9.
2. Uhlmann K, Rohde K, Zeller C, et al. Int J Cancer 2003; 106:52-9.
3. Gao Y, Guan M, Su B, et al. Clin Chim Acta 2004; 349:173-9.
4. Bello M J, Alonso M E, Aminoso C, et al. Mutat Res 2004; 554:23-32.
5. Mancini D N, Rodenhiser D I, Ainsworth P J, et al. Oncogene 1998; 16:1161-9.
6. Szyf M, Pakneshan P, Rabbani S A. Biochem Pharmacol 2004; 68:1187-97.
7. Widschwendter M, Jones P A. Oncogene 2002; 21:5462-82.
8. Lea J S, Coleman R, Kurien A, et al. Am J Obstet Gynecol 2004; 190:674-9.
9. De Zhu J. Cell Res 2005; 15:272-80.
10. Chim C S, Kwong Y L, Fung T K, et al. Leuk Res 2004; 28:379-85.
11. Esteller M, Silva J M, Dominguez G, et al. J Natl Cancer Inst 2000; 92:564-9.
12. Li L C, Okino S T, Dahiya R. Biochim Biophys Acta 2004; 1704:87-102.
13. Kurmasheva et al. Pediatr Blood Cancer 2005; 44:328-37.
14. Sharma R P. Schizophr Res 2005; 72:79-90.
15. Costa E, Chen Y, Davis J, et al. Mol Intery 2002; 2:47-57.
16. Lund G, Anderson L, Lauria M, et al. J Biol Chem 2004; 279:29147-54.

Figure 8A:
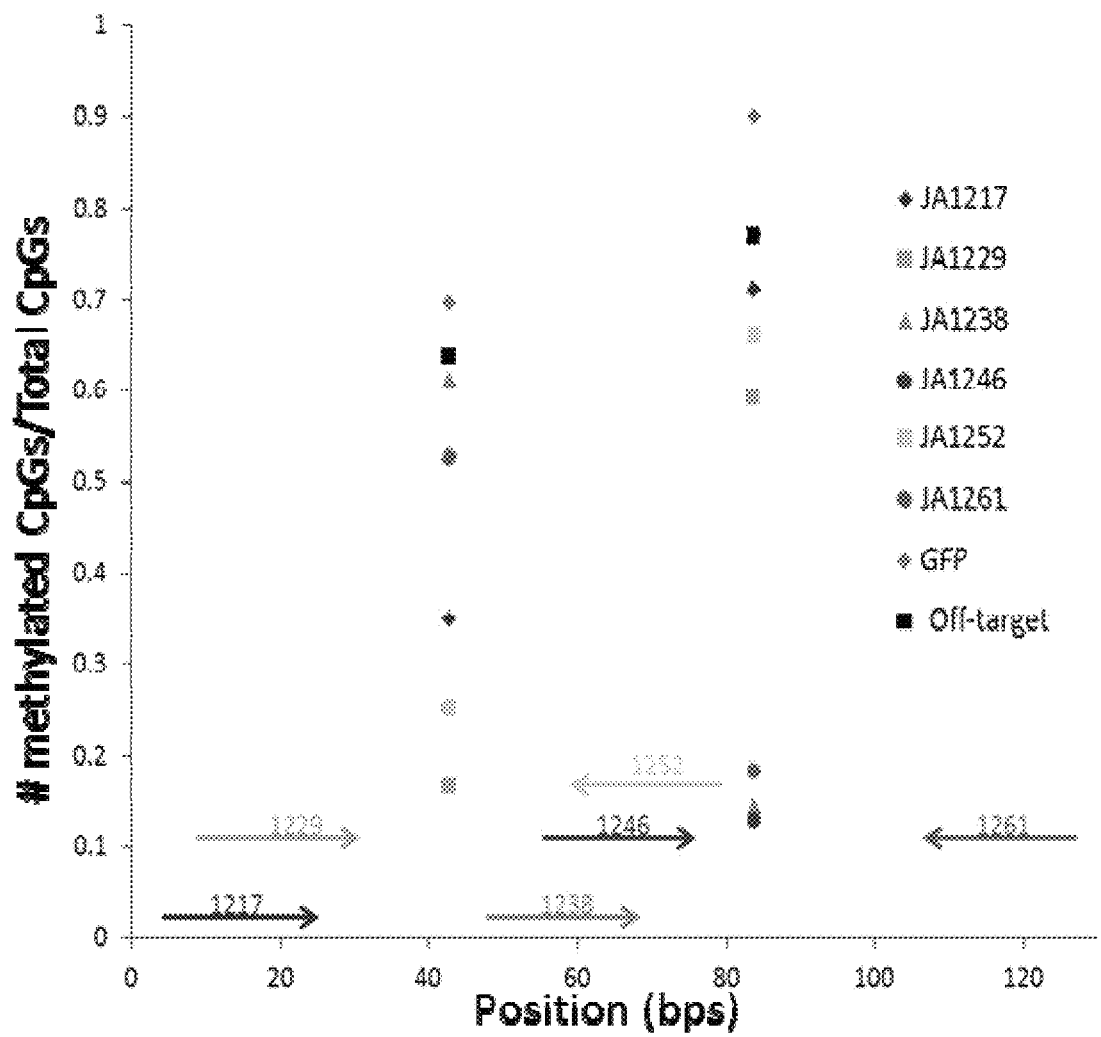
Figure 8B:
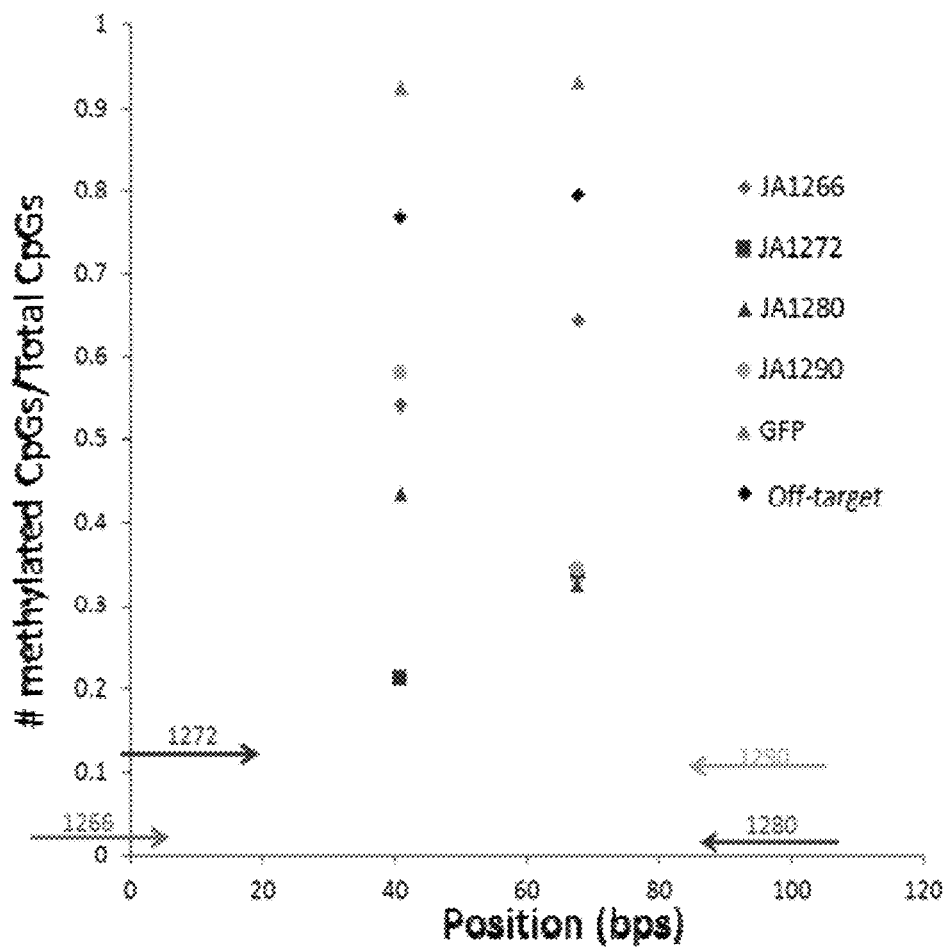
Figure 8C:
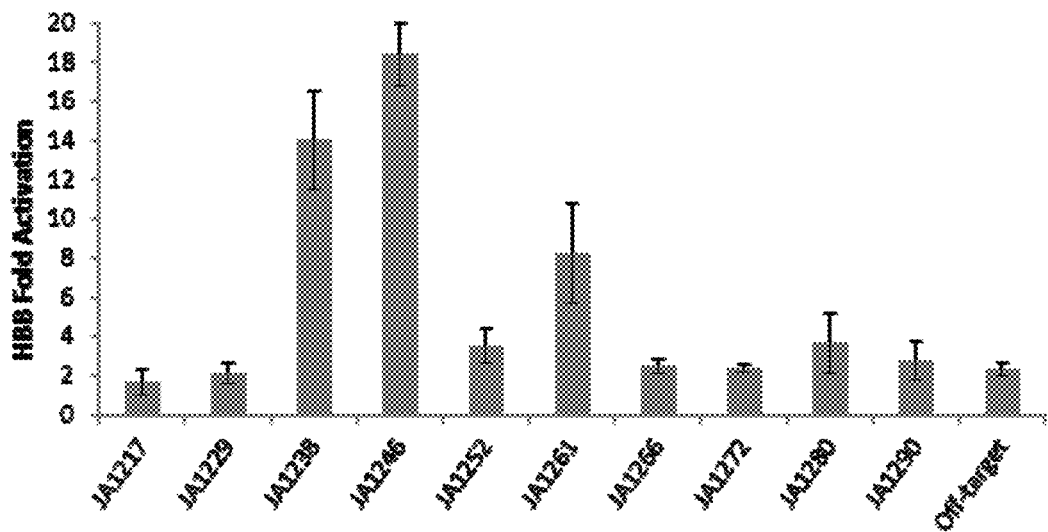

FIGS. 8A-C. Demethylation of human β-globin locus. A) Ratio of methylated to total CpGs at two CpGs located ~300 bp upstream of the transcription start site in cells transfected with TALE-Tet1 proteins, GFP control (diamonds) or off-target control (squares). Arrows indicate location of TALE binding sites. B) Ratio of methylated to total CpGs at two CpGs located ~100 bp downstream of the transcription start site in cells transfected with TALE-Tet1 proteins, GFP control (diamonds) or off-target control (squares). Arrows indicate location of TALE binding sites. C) Expression levels of β-globin mRNA in cells transfected with TALE-Tet1 proteins as determined by qRT-PCR. Fold activation is calculated relative to a GFP control. Error bars represent sem of three independent samples.

Figure 9A:
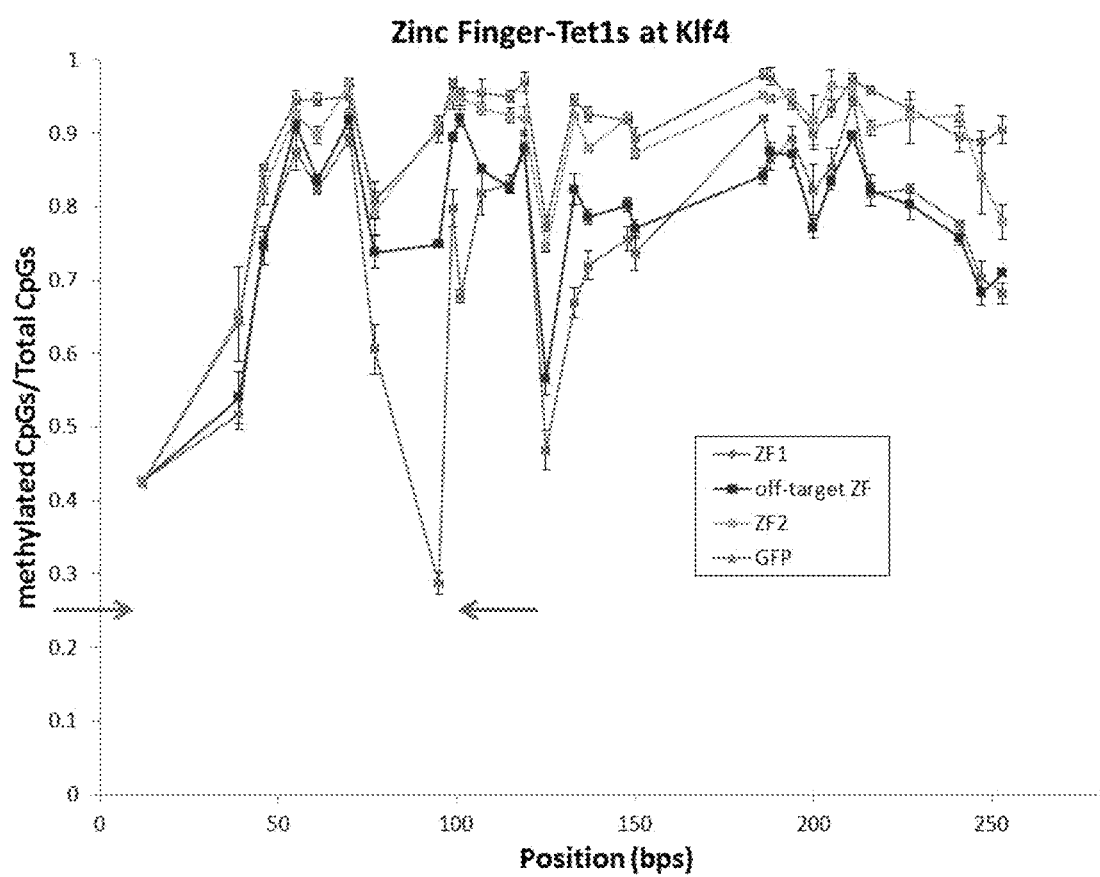
Figure 9B:
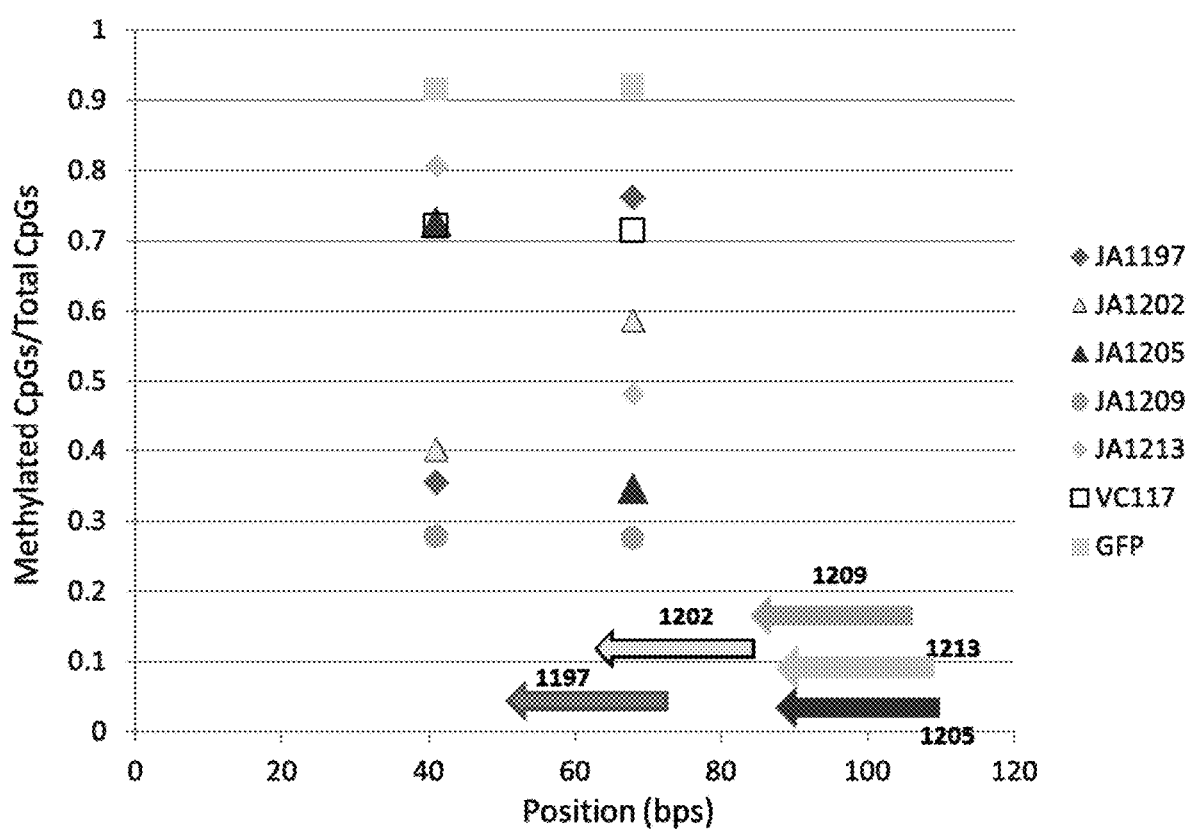

FIGS. 9A-B. Engineered Zinc Finger-Tet Fusion Proteins. A) Ratio of methylated to total CpGs at each position in the Klf4 locus in cells transfected with ZFTet1 proteins (diamonds and circles), GFP (diamonds) or an off-target control (squares). Arrows indicate the location of zinc finger binding sites. B) Ratio of methylated to total CpGs at each position in the β-globin locus in cells transfected with ZF-Tet1 proteins, GFP (squares) or an off-target control (VC117, squares). Arrows represent the location of ZF binding sites and are colored to correspond to their respective data points.

DETAILED DESCRIPTION

Described herein are fusion proteins comprising a DNA-binding domain (i.e., an engineered custom DNA-binding domain), and a catalytic domain (from a different protein) comprising a sequence that catalyzes hydroxylation of methylated cytosines in DNA, with an optional linker between the two domains. As described herein, expression of a TAL effector repeat array-Tet1 (TAL-Tet1) fusion protein in human K562 cells results in demethylation of CpGs in close proximity to the target site bound by the TAL effector repeat array part of the protein.

Exemplified is a hybrid protein consisting of an engineered transcription activator-like (TAL) effector repeat array fused to either the full length Tet1 protein (Tet1-FL), the catalytic domain of Tet1 (Tet1-CD), or a truncated version of the Tet1-FL protein in which the putative native DNA-binding domain has been removed (Tet1-NZ). DNA-binding specificity is defined by the engineered TAL effector repeat array. These DNA-binding proteins can be engineered to bind to essentially any DNA sequence and published work from various labs, as well as published and unpublished work from our lab, has demonstrated that these customizable domains can efficiently target a variety of fused domains to specific genomic locations (Reyon et al., FLASH assembly of TALENs for high-throughput genome editing. Nat Biotechnol (2012).doi:10.1038/nbt.2170; Moscou and Bogdanove, Science 326, 1501-1501 (2009); Boch et al., Science 326, 1509-1512 (2009); Miller et al., Nat Biotechnol 29, 143-148 (2010)). For example, engineered TAL effector repeat arrays have been fused to the cleavage domain of the FokI endonuclease as well as activators and repressors and act to target these domains to a user-defined sequence within the context of the genome.

DNA-Binding Domains

The fusion proteins described herein can include any DNA Binding Domain (DBD) known in the art or engineered for a specific binding site. Exemplary DBDs include engineered or native TAL effector repeat arrays, engineered or native zinc fingers, homing meganucleases, chemical nucleases, and native DBDs.

TAL Effector Repeat Arrays

TAL effectors of plant pathogenic bacteria in the genus Xanthomonas play important roles in disease, or trigger defense, by binding host DNA and activating effector-specific host genes. Specificity depends on an effector-variable number of imperfect, typically ~33-35 amino acid repeats. Polymorphisms are present primarily at repeat positions 12 and 13, which are referred to herein as the repeat variable-diresidue (RVD). The RVDs of TAL effectors correspond to the nucleotides in their target sites in a direct, linear fashion, one RVD to one nucleotide, with some degeneracy and no apparent context dependence. In some embodiments, the polymorphic region that grants nucleotide specificity may be expressed as a triresidue or triplet.

Each DNA binding repeat can include a RVD that determines recognition of a base pair in the target DNA sequence, wherein each DNA binding repeat is responsible for recognizing one base pair in the target DNA sequence. In some embodiments, the RVD can comprise one or more of: HA for recognizing C; ND for recognizing C; HI for recognizing C; HN for recognizing G; NA for recognizing G; SN for recognizing G or A; YG for recognizing T; and NK for recognizing and one or more of: HD for recognizing C; NG for recognizing T; NI for recognizing A; NN for recognizing G or A; NS for recognizing A or C or G or T; N* for recognizing C or T, wherein * represents a gap in the second position of the RVD; HG for recognizing T; H* for recognizing T, wherein * represents a gap in the second position of the RVD; and IG for recognizing T.

TALE proteins may be useful in research and biotechnology as targeted chimeric nucleases that can facilitate homologous recombination in genome engineering (e.g., to add or enhance traits useful for biofuels or biorenewables in plants). These proteins also may be useful as, for example, transcription factors, and especially for therapeutic applications requiring a very high level of specificity such as therapeutics against pathogens (e.g., viruses) as non-limiting examples.

Methods for generating engineered TALE arrays are known in the art, see, e.g., the fast ligation-based automatable solid-phase high-throughput (FLASH) system described in U.S. Ser. No. 61/610,212, and Reyon et al., Nature Biotechnology 30,460-465 (2012); as well as the methods described in Bogdanove & Voytas, Science 333, 1843-1846 (2011); Bogdanove et al., Curr Opin Plant Biol 13, 394-401 (2010); Scholze & Boch, J. Curr Opin Microbiol (2011); Boch et al., Science 326, 1509-1512 (2009); Moscou & Bogdanove, Science 326, 1501 (2009); Miller et al., Nat Biotechnol 29, 143-148 (2011); Morbitzer et al., T. Proc Natl Acad Sci USA 107, 21617-21622 (2010); Morbitzer et al., Nucleic Acids Res 39, 5790-5799 (2011); Zhang et al., Nat Biotechnol 29, 149-153 (2011); Geissler et al., PLoS ONE 6, e19509 (2011); Weber et al., PLoS ONE 6, e19722 (2011); Christian et al., Genetics 186, 757-761 (2010); Li et al., Nucleic Acids Res 39, 359-372 (2011); Mahfouz et al., Proc Natl Acad Sci USA 108, 2623-2628 (2011); Mussolino et al., Nucleic Acids Res (2011); Li et al., Nucleic Acids Res 39, 6315-6325 (2011); Cermak et al., Nucleic Acids Res 39, e82 (2011); Wood et al., Science 333, 307 (2011); Hockemeye et al. Nat Biotechnol 29, 731-734 (2011); Tesson et al., Nat Biotechnol 29, 695-696 (2011); Sander et al., Nat Biotechnol 29, 697-698 (2011); Huang et al., Nat Biotechnol 29, 699-700 (2011); and Zhang et al., Nat Biotechnol 29, 149-153 (2011); all of which are incorporated herein by reference in their entirety.

Zinc Fingers

Zinc finger proteins are DNA-binding proteins that contain one or more zinc fingers, independently folded zinc-containing mini-domains, the structure of which is well known in the art and defined in, for example, Miller et al., 1985, EMBO J., 4:1609; Berg, 1988, Proc. Natl. Acad. Sci. USA, 85:99; Lee et al., 1989, Science. 245:635; and Klug, 1993, Gene, 135:83. Crystal structures of the zinc finger protein Zif268 and its variants bound to DNA show a semi-conserved pattern of interactions, in which typically three amino acids from the alpha-helix of the zinc finger contact three adjacent base pairs or a "subsite" in the DNA (Pavletich et al., 1991, Science, 252:809; Elrod-Erickson et al., 1998, Structure, 6:451). Thus, the crystal structure of Zif268 suggested that zinc finger DNA-binding domains might function in a modular manner with a one-to-one interaction between a zinc finger and a three-base-pair "subsite" in the DNA sequence. In naturally occurring zinc finger transcription factors, multiple zinc fingers are typically linked together in a tandem array to achieve sequence-specific recognition of a contiguous DNA sequence (Klug, 1993, Gene 135:83).

Multiple studies have shown that it is possible to artificially engineer the DNA binding characteristics of individual zinc fingers by randomizing the amino acids at the alpha-helical positions involved in DNA binding and using selection methodologies such as phage display to identify desired variants capable of binding to DNA target sites of interest (Rebar et al., 1994, Science, 263:671; Choo et al., 1994 Proc. Natl. Acad. Sci. USA, 91:11163; Jamieson et al., 1994, Biochemistry 33:5689; Wu et al., 1995 Proc. Natl. Acad. Sci. USA, 92: 344). Such recombinant zinc finger proteins can be fused to functional domains, such as transcriptional activators, transcriptional repressors, methylation domains, and nucleases to regulate gene expression, alter DNA methylation, and introduce targeted alterations into genomes of model organisms, plants, and human cells (Carroll, 2008, Gene Ther., 15:1463-68; Cathomen, 2008, Mol. Ther., 16:1200-07; Wu et al., 2007, Cell. Mol. Life Sci., 64:2933-44).

Widespread adoption and large-scale use of zinc finger protein technology have been hindered by the continued lack of a robust, easy-to-use, and publicly available method for engineering zinc finger arrays. One existing approach, known as "modular assembly," advocates the simple joining together of pre-selected zinc finger modules into arrays (Segal et al., 2003, Biochemistry, 42:2137-48; Beerli et al., 2002, Nat. Biotechnol., 20:135-141; Mandell et al., 2006, Nucleic Acids Res., 34:W516-523; Carroll et al., 2006, Nat. Protoc. 1:1329-41; Liu et al., 2002, J. Biol. Chem., 277: 3850-56; Bae et al., 2003, Nat. Biotechnol., 21:275-280; Wright et al., 2006, Nat. Protoc., 1:1637-52). Although straightforward enough to be practiced by any researcher, recent reports have demonstrated a high failure rate for this method, particularly in the context of zinc finger nucleases (Ramirez et al., 2008, Nat. Methods, 5:374-375; Kim et al., 2009, Genome Res. 19:1279-88), a limitation that typically necessitates the construction and cell-based testing of very large numbers of zinc finger proteins for any given target gene (Kim et al., 2009, Genome Res. 19:1279-88).

Combinatorial selection-based methods that identify zinc finger arrays from randomized libraries have been shown to have higher success rates than modular assembly (Maeder et al., 2008, Mol. Cell, 31:294-301; Joung et al., 2010, Nat. Methods, 7:91-92; Isalan et al., 2001, Nat. Biotechnol., 19:656-660). In preferred embodiments, the zinc finger arrays are described in, or are generated as described in, WO 2011/017293 and WO 2004/099366. Additional suitable zinc finger DBDs are described in U.S. Pat. Nos. 6,511,808, 6,013,453, 6,007,988, and 6,503,717 and U.S. patent application 2002/0160940.

Native DBDs

In some embodiments, a native DBD (e.g., a portion of a wild-type, non-engineered DNA binding protein that binds to a specific target sequence) can be used. For example, the DBD from a transcription factor, nuclease, histone, telomerase, or other DNA binding protein can be used. Typically DBDs include a structure that facilitates specific interaction with a target nucleic acid sequence; common DBD structures include helix-turn-helix; zinc finger; leucine zipper; winged helix; winged helix turn helix; helix-loop-helix; and hmg-box. The native DBD can be from any organism. See, e.g., Kummerfeld & Teichmann, Nucleic Acids Res. 34 (Database issue): D74-81 (2006). The residues in a DNA binding protein that contact DNA, and thus form part of the DBD, can be determined empirically or predicted computationally, e.g., as described in Tjong and Zhou, Nucl. Acids Res. 35:1465-1477 (2007). A database of DNA binding proteins can be used to identify DNA binding proteins and DBDs for use in the present compositions and methods; see, e.g., Harrison, Nature, 353, 715-719 (1991); Karmirantzou and Hamodrakas, Protein Eng. 14(7): 465-472 (2001); Kumar et al., BMC Bioinformatics. 8:463 (2007); Kumar et al., J Biomol Struct Dyn. 26(6):679-86 (2009); Lin et al., PLoS One. 6(9):e24756 (2011).

Where a native DBD is used in a fusion protein described herein, the catalytic domain is from a different protein.

Homing Meganucleases

Meganucleases are sequence-specific endonucleases originating from a variety of organisms such as bacteria, yeast, algae and plant organelles. Endogenous meganucleases have recognition sites of 12 to 30 base pairs; customized DNA binding sites with 18 bp and 24 bp-long meganuclease recognition sites have been described, and either can be used in the present methods and constructs. See, e.g., Silva, G, et al., Current Gene Therapy, 11:11-27, (2011); Arnould et al., Journal of Molecular Biology, 355:443-58 (2006); Arnould et al., Protein Engineering Design & Selection, 24:27-31 (2011); and Stoddard, Q. Rev. Biophys. 38, 49 (2005); Grizot et al., Nucleic Acids Research, 38:2006-18 (2010).

Chemical Nucleases

DNA binding domains from the so-called "chemical nucleases," (Pingoud and Silva, Nat Biotechnol. 25:743-4 (2007)), e.g., triplex-forming oligonucleotides or peptide nucleic acids can also be utilized in the present compositions and methods; see, e.g., Schleifman et al., Methods Mol Biol. 2008; 435:175-90; Arimondo et al., Mol Cell Biol. 2006 January; 26(1):324-33; Majumdar et al., J Biol Chem. 2008 Apr. 25; 283(17):11244-52; Simon et al., Nucleic Acids Res. 2008 June; 36(11):3531-8; or Eisenschmidt et al., Nucleic Acids Res. 2005; 33(22):7039-47.

Catalytic Domains

The fusion proteins include a catalytic domain comprising a sequence that catalyzes hydroxylation of methylated cytosines in DNA. Exemplary proteins include the Ten-Eleven-Translocation (TET)1-3 family, enzymes that converts 5-methylcytosine (5-mC) to 5-hydroxymethylcytosine (5-hmC) in DNA.

Sequences for human TET1-3 are known in the art and are shown in the following table:

| | GenBank Accession Nos. | |
| --- | --- | --- |
| Gene | Amino Acid | Nucleic Acid |
| TET1 | NP_085128.2 | NM_030625.2 |
| TET2* | NP_001120680.1 (var 1) | NM_001127208.2 |
| | NP_060098.3 (var 2) | NM_017628.4 |
| TET3 | NP_659430.1 | NM_144993.1 |

*Variant (1) represents the longer transcript and encodes the longer isoform (a). Variant (2) differs in the 5' UTR and in the 3' UTR and coding sequence compared to variant 1. The resulting isoform (b) is shorter and has a distinct C-terminus compared to isoform a.

In some embodiments, all or part of the full-length sequence of the catalytic domain can be included, e.g., a catalytic module comprising the cysteine-rich extension and the 2OGFeDO domain encoded by 7 highly conserved exons, e.g., the Tet1 catalytic domain comprising amino acids 1580-2052, Tet2 comprising amino acids 1290-1905 and Tet3 comprising amino acids 966-1678. See, e.g., FIG. 1 of Iyer et al., Cell Cycle. 2009 Jun. 1; 8(11):1698-710. Epub 2009 Jun. 27, for an alignment illustrating the key catalytic residues in all three Tet proteins, and the supplementary materials thereof (available at ftp site ftp.ncbi.nih.gov/pub/aravind/DONS/supplementary material DONS.html) for full length sequences (see, e.g., seq 2c); in some embodiments, the sequence includes amino acids 1418-2136 of Tet1 or the corresponding region in Tet2/3.

Other catalytic modules can be from the proteins identified in Iyer et al., 2009.

Construction of Fusion Proteins

To generate a functional recombinant protein, the DNA binding domain is fused to at least one catalytic domain. Fusing catalytic domains to DBD to form functional fusion proteins involves only routine molecular biology techniques that are commonly practiced by those of skill in the art, see for example, U.S. Pat. Nos. 6,511,808, 6,013,453, 6,007,988, 6,503,717 and U.S. patent application 2002/0160940). Catalytic domains can be associated with the DBD domain at any suitable position, including the C- or N-terminus of the DBD. In some embodiments, the fusion proteins include multiple catalytic domains, e.g., on one or both ends of the DBD, e.g., concatenated together with an optional intervening linker; thus there can be one or more catalytic domains on each end of the DBD.

Alternatively, the catalytic domains, e.g., Tet1 units, could be multimerized through specific constitutive or inducible protein-protein interaction domains (such as leucine zipper domains or ClonTech's iDimerize system, homodimerization and heterodimerization systems and ligands (e.g. AP20187, AP21967) which were previously provided by ARIAD under the brand name ARGENT. The BB Homodimerizer (AP20187) induces dimerization of two proteins that each contain the DmrB homodimerization domain (see table below explaining domain nomenclature). The A/C Heterodimerizer (AP21967) induces dimerization of a protein possessing the DmrA domain and a second protein containing the DmrC domain. The D/D Solubilizer (alternative to AP21998) induces dissociation/disaggregation of proteins possessing DmrD domains. DmrD causes automatic self-association of proteins fused to it; see, e.g., Burnett et al., J. Leukoc. Biol. 75(4):612-623 (2004); Freeman et al., Cancer Res. 63(23):8256-8563 (2003); Castellano et al., Curr. Biol. 9(7): 351-360 (1999); Crabtree and Schreiber, Trends Biochem. Sci. 21(11): 418-422 (1996); Graef et al., Embo. J. 16(18): 5618-5628 (1997); Muthuswamy et al., Mol. Cell. Biol. 19(10): 6845-6857 (1999)), Alternatively, multimerization could be achieved through the use of split-inteins, a class of autocatyltic intein peptides that allow for the seamless covalent splicing of two separate proteins in a predictable and efficient manner (d'Avignon, et al., Biopolymers. 2006 Oct. 15; 83(3):255-67; Zitzewitz, et al., Biochemistry. 1995 Oct. 3; 34(39):12812-9; Li et al., Hum Gene Ther. 2008 September; 19(9):958-64). Both the protein-protein interaction and intein approaches could be optimized to produce very long multimerized strings of catalytic domains. FIGS. 6A-D show exemplary schemes for multimerization.

Methods of Use of the Fusion Proteins

The fusion proteins designed and produced using the methods described herein can be used to perform any function where it is desired to demethylate a specific DNA sequence. The fusion proteins can be useful for the treatment of disease; for example, the fusion proteins can be targeted to a hypermethylated region of a gene listed in Table 1 of Rodenhiser and Mann, CMAJ 174(3):341-348 (2006) as hypermethylated in a disease, which is reproduced as FIG. 7 hereto, or a reference set forth therein, or for otherwise altering the structure or function of a given gene in vivo. The fusion proteins of the present invention are also useful as research tools, for example, in performing either in vivo or in vitro functional genomics studies (see, for example, U.S. Pat. No. 6,503,717 and U.S. patent application 2002/0164575).

Polypeptide Expression Systems

In order to use the fusion proteins described, it may be desirable to express the engineered proteins from a nucleic acid that encodes them. This can be performed in a variety of ways. For example, the nucleic acid encoding the fusion protein can be cloned into an intermediate vector for transformation into prokaryotic or eukaryotic cells for replication and/or expression. Intermediate vectors are typically prokaryote vectors, e.g., plasmids, or shuttle vectors, or insect vectors, for storage or manipulation of the nucleic acid encoding the fusion protein or for production of the fusion protein. The nucleic acid encoding the fusion protein can also be cloned into an expression vector, for administration to a plant cell, animal cell, preferably a mammalian cell or a human cell, fungal cell, bacterial cell, or protozoan cell.

To obtain expression, the fusion protein is typically subcloned into an expression vector that contains a promoter to direct transcription. Suitable bacterial and eukaryotic promoters are well known in the art and described, e.g., in Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 2010). Bacterial expression systems for expressing the engineered TALE repeat protein are available in, e.g., *E. coli, Bacillus* sp., and *Salmonella* (Palva et al., 1983, Gene 22:229-235). Kits for such expression systems are commercially available. Eukaryotic expression systems for mammalian cells, yeast, and insect cells are well known in the art and are also commercially available.

The promoter used to direct expression of the fusion protein nucleic acid depends on the particular application. For example, a strong constitutive promoter is typically used for expression and purification of fusion proteins. In contrast, when the fusion protein is to be administered in vivo for gene regulation, either a constitutive or an inducible promoter can be used, depending on the particular use of the fusion protein. In addition, a preferred promoter for administration of the fusion protein can be a weak promoter, such as HSV TK or a promoter having similar activity. The promoter can also include elements that are responsive to transactivation, e.g., hypoxia response elements, Gal4 response elements, lac repressor response element, and small molecule control systems such as tetracycline-regulated systems and the RU-486 system (see, e.g., Gossen & Bujard, 1992, Proc. Natl. Acad. Sci. USA, 89:5547; Oligino et al., 1998, Gene Ther., 5:491-496; Wang et al., 1997, Gene Ther., 4:432-441; Neering et al., 1996, Blood, 88:1147-55; and Rendahl et al., 1998, Nat. Biotechnol., 16:757-761).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the fusion protein, and any signals required, e.g., for efficient polyadenylation of the transcript, transcriptional termination, ribosome binding sites, or translation termination. Additional elements of the cassette may include, e.g., enhancers, and heterologous spliced intronic signals.

The particular expression vector used to transport the genetic information into the cell is selected with regard to the intended use of the fusion protein, e.g., expression in plants, animals, bacteria, fungus, protozoa, etc. Standard bacterial expression vectors include plasmids such as pBR322 based plasmids, pSKF, pET23D, and commercially available tag-fusion expression systems such as GST and LacZ. A preferred tag-fusion protein is the maltose binding protein, "MBP." Such tag-fusion proteins can be used for purification of the engineered TALE repeat protein. Epitope tags can also be added to recombinant proteins to provide convenient methods of isolation, for monitoring expression, and for monitoring cellular and subcellular localization, e.g., c-myc or FLAG.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with the fusion protein encoding sequence under the direction of the polyhedrin promoter or other strong baculovirus promoters.

The elements that are typically included in expression vectors also include a replicon that functions in $E.$ $coli$, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., 1989, J. Biol. Chem., 264:17619-22; Guide to Protein Purification, in Methods in Enzymology, vol. 182 (Deutscher, ed., 1990)). Transformation of eukaryotic and prokaryotic cells are performed according to standard techniques (see, e.g., Morrison, 1977, J. Bacteriol. 132:349-351; Clark-Curtiss & Curtiss, Methods in Enzymology 101:347-362 (Wu et al., eds, 1983).

Any of the known procedures for introducing foreign nucleotide sequences into host cells may be used. These include the use of calcium phosphate transfection, polybrene, protoplast fusion, electroporation, NUCLEOFECTION, liposomes, microinjection, naked DNA, plasmid vectors, viral vectors both episomal and integrative, and any of the other well-known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

In some embodiments, the fusion protein includes a nuclear localization domain which provides for the protein to be translocated to the nucleus. Several nuclear localization sequences (NLS) are known, and any suitable NLS can be used. For example, many NLSs have a plurality of basic amino acids, referred to as a bipartite basic repeats (reviewed in Garcia-Bustos et al, 1991, Biochim. Biophys. Acta, 1071:83-101). An NLS containing bipartite basic repeats can be placed in any portion of chimeric protein and results in the chimeric protein being localized inside the nucleus. In preferred embodiments a nuclear localization domain is incorporated into the final fusion protein, as the ultimate functions of the fusion proteins described herein will typically require the proteins to be localized in the nucleus. However, it may not be necessary to add a separate nuclear localization domain in cases where the DBD domain itself, or another functional domain within the final chimeric protein, has intrinsic nuclear translocation function.

Use of Fusion Proteins in Gene Therapy

The fusion proteins described herein can be used to regulate gene expression or alter gene sequence in gene therapy applications in the same. See for example U.S. Pat. Nos. 6,511,808, 6,013,453, 6,007,988, 6,503,717, U.S. patent application 2002/0164575, and U.S. patent application 2002/0160940. The methods can include administering one or more of the fusion proteins described herein targeted to one or more genes. Since methylation of many CpGs across hundreds of basepairs of DNA in promoters or imprinted regions can influence gene expression (Han et al., Mol Cell Biol. 2008 February; 28(3):1124-35, Mabaera, et al., Blood. 2007 Aug. 15; 110(4):1343-52), it may be desirable to reduce methulation across longer sequences. If a larger region of a gene is desired to be demethylated, a plurality of fusion proteins that all target positions on the same gene, e.g., positions within about 1000, 500, 300, 250, 100, 50, 40, 30, or 20 bp of the site to be demethylated, can be administered. Alternatively or in addition, one or a plurality of fusion proteins that are multimerized as described herein (see, e.g., FIGS. 6A-D) can be administered.

Conventional viral and non-viral based gene transfer methods can be used to introduce nucleic acids encoding the fusion protein into mammalian cells or target tissues. Such methods can be used to administer nucleic acids encoding fusion proteins to cells in vitro. Preferably, the nucleic acids encoding the fusion proteins are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, 1992, Science, 256:808-813; Nabel & Felgner, 1993, TIBTECH, 11:211-217; Mitani & Caskey, 1993, TIBTECH, 11:162-166; Dillon, 1993, TIBTECH, 11:167-175; Miller, 1992, Nature, 357:455-460; Van Brunt, 1988, Biotechnology, 6:1149-54; Vigne, 1995, Restorat. Neurol. Neurosci., 8:35-36; Kremer & Perricaudet, 1995, Br. Med. Bull., 51:31-44; Haddada et al., in Current Topics in Microbiology and Immunology Doerfler and Bohm (eds) (1995); and Yu et al., 1994, Gene Ther., 1:13-26.

Methods of non-viral delivery of nucleic acids encoding the fusion proteins include lipofection, microinjection, biolistics, virosomes, liposomes, immunoliposomes, polycation or lipid:nucleic acid conjugates, naked DNA or RNA, artificial virions, and agent-enhanced uptake of DNA or RNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, 1995, Science, 270:404-410; Blaese et al., 1995, Cancer Gene Ther., 2:291-297; Behr et al., 1994, Bioconjugate Chem. 5:382-389; Remy et al., 1994, Bioconjugate Chem., 5:647-654; Gao et al., Gene Ther., 2:710-722; Ahmad et al., 1992, Cancer Res., 52:4817-20; U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids encoding the fusion proteins takes advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of fusion proteins could include retroviral, lentivirus, adenoviral, adeno-associated, Sendai, and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., 1992, J. Virol., 66:2731-39; Johann et al., 1992, J. Virol., 66:1635-40; Sommerfelt et al., 1990, Virololgy, 176: 58-59; Wilson et al., 1989, J. Virol., 63:2374-78; Miller et al., 1991, J. Virol., 65:2220-24; WO 94/26877).

In applications where transient expression of the fusion protein is preferred, adenoviral based systems can be used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., 1987, Virology 160:38-47; U.S. Pat. No. 4,797,368; WO 93/24641; Kotin, 1994, Hum. Gene Ther., 5:793-801; Muzyczka, 1994, J. Clin. Invest., 94:1351). Construction of recombinant AAV vectors are described in a number of publications, including U.S. Pat. No. 5,173,414; Tratschin et al., 1985, Mol. Cell. Biol. 5:3251-60; Tratschin et al.,1984, Mol. Cell. Biol., 4:2072-81; Hermonat & Muzyczka, 1984, Proc. Natl. Acad. Sci. USA, 81:6466-70; and Samulski et al., 1989, J. Virol., 63:3822-28.

In particular, at least six viral vector approaches are currently available for gene transfer in clinical trials, with retroviral vectors by far the most frequently used system. All of these viral vectors utilize approaches that involve complementation of defective vectors by genes inserted into helper cell lines to generate the transducing agent.

pLASN and MFG-S are examples are retroviral vectors that have been used in clinical trials (Dunbar et al., 1995, Blood, 85:3048; Kohn et al.,1995, Nat. Med., 1:1017; Malech et al., 1997, Proc. Natl. Acad. Sci. USA, 94:12133-38). PA317/pLASN was the first therapeutic vector used in a gene therapy trial. (Blaese et al., 1995, Science, 270:475-480). Transduction efficiencies of 50% or greater have been observed for MFG-S packaged vectors (Ellem et al., 1997, Immunol Immunother., 44:10-20; Dranoffet al., 1997, Hum. Gene Ther., 1:111-112).

Recombinant adeno-associated virus vectors (rAAV) are a promising alternative gene delivery systems based on the defective and nonpathogenic parvovirus adeno-associated type 2 virus. Typically, the vectors are derived from a plasmid that retains only the AAV 145 bp inverted terminal repeats flanking the transgene expression cassette. Efficient gene transfer and stable transgene delivery due to integration into the genomes of the transduced cell are key features for this vector system (Wagner et al., 1998, Lancet, 351:1702-1703; Kearns et al., 1996, Gene Ther., 9:748-55).

Replication-deficient recombinant adenoviral vectors (Ad) are predominantly used for colon cancer gene therapy, because they can be produced at high titer and they readily infect a number of different cell types. Most adenovirus vectors are engineered such that a transgene replaces the Ad E1a, E1b, and E3 genes; subsequently the replication defector vector is propagated in human 293 cells that supply deleted gene function in trans. Ad vectors can transduce multiple types of tissues in vivo, including nondividing, differentiated cells such as those found in the liver, kidney and muscle system tissues. Conventional Ad vectors have a large carrying capacity. An example of the use of an Ad vector in a clinical trial involved polynucleotide therapy for antitumor immunization with intramuscular injection (Sterman et al., 1998, Hum. Gene Ther. 7:1083-89). Additional examples of the use of adenovirus vectors for gene transfer in clinical trials include Rosenecker et al., 1996, Infection, 24:15-10; Sterman et al., 1998, Hum. Gene Ther., 9:7 1083-89; Welsh et al., 1995, Hum. Gene Ther., 2:205-218; Alvarez et al., 1997, Hum. Gene Ther. 5:597-613; Topf et al., 1998, Gene Ther., 5:507-513; Sterman et al., 1998, Hum. Gene Ther., 7:1083-89.

Packaging cells are used to form virus particles that are capable of infecting a host cell. Such cells include 293 cells, which package adenovirus, and Ψ2 cells or PA317 cells, which package retrovirus. Viral vectors used in gene therapy are usually generated by producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., 1995, Proc. Natl. Acad. Sci. USA, 92:9747-51, reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., Fab or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or stem cells (e.g., universal donor hematopoietic stem cells, embryonic stem cells (ES), partially differentiated stem cells, non-pluripotent stem cells, pluripotent stem cells, induced pluripotent stem cells (iPS cells) (see e.g., Sipione et al., Diabetologia, 47:499-508, 2004)), followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with nucleic acid (gene or cDNA), encoding the fusion protein, and re-infused back into the subject organism (e.g., patient). Various cell types suitable for ex vivo transfection are well known to those of skill in the art (see, e.g., Freshney et al., Culture of Animal Cells, A Manual of Basic Technique (5th ed. 2005)) and the references cited therein for a discussion of how to isolate and culture cells from patients).

In one embodiment, stem cells (e.g., universal donor hematopoietic stem cells, embryonic stem cells (ES), partially differentiated stem cells, non-pluripotent stem cells, pluripotent stem cells, induced pluripotent stem cells (iPS cells) (see e.g., Sipione et al., Diabetologia, 47:499-508, 2004)) are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-gamma and TNF-alpha are known (see Inaba et al., 1992, J. Exp. Med., 176:1693-1702).

Stem cells can be isolated for transduction and differentiation using known methods. For example, stem cells can be isolated from bone marrow cells by panning the bone marrow cells with antibodies which bind unwanted cells, such as CD4+ and CD8+ (T cells), CD45+ (panB cells), GR-1 (granulocytes), and Iad (differentiated antigen presenting cells) (see Inaba et al., 1992, J. Exp. Med., 176:1693-1702).

Vectors (e.g., retroviruses, adenoviruses, liposomes, etc.) containing nucleic acids encoding the fusion protein can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route. Alternatively, stable formulations of the fusion protein can also be administered.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., Remington: The Science and Practice of Pharmacy, 21st ed., 2005).

Delivery Vehicles

An important factor in the administration of polypeptide compounds, such as the fusion proteins of the present invention, is ensuring that the polypeptide has the ability to traverse the plasma membrane of a cell, or the membrane of an intra-cellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins and other compounds such as liposomes have been described, which have the ability to translocate polypeptides such as fusion protein across a cell membrane.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, 1996, Curr. Opin. Neurobiol., 6:629-634). Another subsequence, the h (hydrophobic) domain of signal peptides, was found to have similar cell membrane translocation characteristics (see, e.g., Lin et al., 1995, J. Biol. Chem., 270:14255-58).

Examples of peptide sequences that can be linked to a protein, for facilitating uptake of the protein into cells, include, but are not limited to: peptide fragments of the tat protein of HIV (Endoh et al., 2010, Methods Mol. Biol., 623:271-281; Schmidt et al., 2010, FEBS Lett., 584:1806-13; Futaki, 2006, Biopolymers, 84:241-249); a 20 residue peptide sequence which corresponds to amino acids 84-103 of the p16 protein (see Fahraeus et al., 1996, Curr. Biol., 6:84); the third helix of the 60-amino acid long homeodomain of Antennapedia (Derossi et al., 1994, J. Biol. Chem., 269:10444); the h region of a signal peptide, such as the Kaposi fibroblast growth factor (K-FGF) h region (Lin et al., supra); or the VP22 translocation domain from HSV (Elliot & O'Hare, 1997, Cell, 88:223-233). See also, e.g., Caron et al., 2001, Mol Ther., 3:310-318; Langel, Cell-Penetrating Peptides: Processes and Applications (CRC Press, Boca Raton Fla. 2002); El-Andaloussi et al., 2005, Curr. Pharm. Des., 11:3597-3611; and Deshayes et al., 2005, Cell. Mol. Life Sci., 62:1839-49. Other suitable chemical moieties that provide enhanced cellular uptake may also be chemically linked to Fusion proteins described herein.

Toxin molecules also have the ability to transport polypeptides across cell membranes. Often, such molecules are composed of at least two parts (called "binary toxins"): a translocation or binding domain or polypeptide and a separate toxin domain or polypeptide. Typically, the translocation domain or polypeptide binds to a cellular receptor, and then the toxin is transported into the cell. Several bacterial toxins, including *Clostridium perfringens* iota toxin, diphtheria toxin (DT), *Pseudomonas exotoxin* A (PE), pertussis toxin (PT), *Bacillus anthracis* toxin, and pertussis adenylate cyclase (CYA), have been used in attempts to deliver peptides to the cell cytosol as internal or amino-terminal fusions (Arora et al., 1993, J. Biol. Chem., 268:3334-41; Perelle et al., 1993, Infect. Immun., 61:5147-56; Stenmark et al., 1991, J. Cell Biol., 113:1025-32; Donnelly et al., 1993, Proc. Natl. Acad. Sci. USA, 90:3530-34; Carbonetti et al., 1995, Abstr. Annu. Meet. Am. Soc. Microbiol. 95:295; Sebo et al., 1995, Infect. Immun., 63:3851-57; Klimpel et al., 1992, Proc. Natl. Acad. Sci. USA, 89:10277-81; and Novak et al., 1992, J. Biol. Chem., 267:17186-93).

Such subsequences can be used to translocate fusion proteins across a cell membrane. The fusion proteins can be conveniently fused to or derivatized with such sequences. Typically, the translocation sequence is provided as part of a fusion protein. Optionally, a linker can be used to link the fusion protein and the translocation sequence. Any suitable linker can be used, e.g., a peptide linker.

The fusion protein can also be introduced into an animal cell, preferably a mammalian cell, via liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell, i.e., the fusion protein.

The liposome fuses with the plasma membrane, thereby releasing the compound into the cytosol. Alternatively, the liposome is phagocytosed or taken up by the cell in a transport vesicle. Once in the endosome or phagosome, the liposome either degrades or fuses with the membrane of the transport vesicle and releases its contents.

In current methods of drug delivery via liposomes, the liposome ultimately becomes permeable and releases the encapsulated compound (e.g., the fusion protein or a nucleic acid encoding the same) at the target tissue or cell. For systemic or tissue specific delivery, this can be accomplished, for example, in a passive manner wherein the liposome bilayer degrades over time through the action of various agents in the body. Alternatively, active compound release involves using an agent to induce a permeability change in the liposome vesicle. Liposome membranes can be constructed so that they become destabilized when the environment becomes acidic near the liposome membrane (see, e.g., Proc. Natl. Acad. Sci. USA, 84:7851 (1987); Biochemistry, 28:908 (1989)). When liposomes are endocytosed by a target cell, for example, they become destabilized and release their contents. This destabilization is termed fusogenesis. Dioleoylphosphatidylethanolamine (DOPE) is the basis of many "fusogenic" systems.

Such liposomes typically comprise the fusion protein and a lipid component, e.g., a neutral and/or cationic lipid, optionally including a receptor-recognition molecule such as an antibody that binds to a predetermined cell surface receptor or ligand (e.g., an antigen). A variety of methods are available for preparing liposomes as described in, e.g., Szoka et al., 1980, Annu. Rev. Biophys. Bioeng., 9:467, U.S. Pat. Nos. 4,186,183, 4,217,344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication. No. WO 91/17424, Deamer & Bangham, 1976, Biochim. Biophys. Acta, 443:629-634; Fraley, et al., 1979, Proc. Natl. Acad. Sci. USA, 76:3348-52; Hope et al., 1985, Biochim. Biophys. Acta, 812:55-65; Mayer et al., 1986, Biochim. Biophys. Acta, 858:161-168; Williams et al., 1988, Proc. Natl. Acad. Sci. USA, 85:242-246; Liposomes (Ostro (ed.), 1983, Chapter 1); Hope et al., 1986, Chem. Phys. Lip., 40:89; Gregoriadis, Liposome Technology (1984) and Lasic, Liposomes: from Physics to Applications (1993)). Suitable methods include, for example, sonication, extrusion, high pressure/homogenization, microfluidization, detergent dialysis, calcium-induced fusion of small liposome vesicles and ether-fusion methods, all of which are well known in the art.

In certain embodiments, it is desirable to target liposomes using targeting moieties that are specific to a particular cell type, tissue, and the like. Targeting of liposomes using a variety of targeting moieties (e.g., ligands, receptors, and monoclonal antibodies) has been previously described (see, e.g., U.S. Pat. Nos. 4,957,773 and 4,603,044).

Examples of targeting moieties include monoclonal antibodies specific to antigens associated with neoplasms, such as prostate cancer specific antigen and MAGE. Tumors can also be diagnosed by detecting gene products resulting from the activation or overexpression of oncogenes, such as ras or c-erbB2. In addition, many tumors express antigens normally expressed by fetal tissue, such as the alphafetoprotein (AFP) and carcinoembryonic antigen (CEA). Sites of viral infection can be diagnosed using various viral antigens such as hepatitis B core and surface antigens (HBVc, HBVs) hepatitis C antigens, Epstein-Barr virus antigens, human immunodeficiency type-1 virus (HIV1) and papilloma virus antigens. Inflammation can be detected using molecules specifically recognized by surface molecules which are expressed at sites of inflammation such as integrins (e.g., VCAM-1), selectin receptors (e.g., ELAM-1) and the like.

Standard methods for coupling targeting agents to liposomes can be used. These methods generally involve incorporation into liposomes lipid components, e.g., phosphatidylethanolamine, which can be activated for attachment of targeting agents, or derivatized lipophilic compounds, such as lipid derivatized bleomycin. Antibody targeted liposomes can be constructed using, for instance, liposomes which incorporate protein A (see Renneisen et al., 1990, J. Biol. Chem., 265:16337-42 and Leonetti et al., 1990, Proc. Natl. Acad. Sci. USA, 87:2448-51).

Dosages

For therapeutic applications, the dose of the fusion protein to be administered to a patient can be calculated in a similar way as has been described for zinc finger proteins, see for example U.S. Pat. Nos. 6,511,808, 6,492,117, 6,453,242, U.S. patent application 2002/0164575, and U.S. patent application 2002/0160940. In the context of the present disclosure, the dose should be sufficient to effect a beneficial therapeutic response in the patient over time. In addition, particular dosage regimens can be useful for determining phenotypic changes in an experimental setting, e.g., in functional genomics studies, and in cell or animal models. The dose will be determined by the efficacy, specificity, and K<sub>D</sub> of the particular fusion protein employed, the nuclear volume of the target cell, and the condition of the patient, as well as the body weight or surface area of the patient to be treated. The size of the dose also will be determined by the existence, nature, and extent of any adverse side-effects that accompany the administration of a particular compound or vector in a particular patient.

Pharmaceutical Compositions and Administration

Appropriate pharmaceutical compositions for administration of the fusion proteins of the present invention can be determined as described for zinc finger proteins, see for example U.S. Pat. Nos. 6,511,808, 6,492,117, 6,453,242, U.S. patent application 2002/0164575, and U.S. patent application 2002/0160940. Fusion proteins, and expression vectors encoding fusion proteins, can be administered directly to the patient for modulation of methylation patterns, e.g., and gene expression, and for therapeutic or prophylactic applications, for example, for treatment of diseases listed in FIG. 7 as associated with hypermethylation, including cancer (e.g., bladder, brain (e.g., glioma, or glioblastoma), breast, cervical, colon, colorectal, esophagus, head/neck, kidney, leukemia, liver, lung, lymphoma, myeloma, ovary, pancreas, prostate, rhabdomyosarcoma, and uterus cancer); schizophrenia; memory formation; and atherosclerosis. Thus the methods can include identifying a subject who has a disease associated with hypermethylation (e.g., optionally including obtaining a sample and detecting methylation of DNA, e.g., of the associated gene listed in FIG. 7, and selecting the subject if their DNA is hypermethylated), and administering a therapeutically effective amount of a fusion protein, or a nucleic acid encoding a fusion protein, as described herein, to the subject.

Administration of therapeutically effective amounts is by any of the routes normally used for introducing Fusion proteins into ultimate contact with the tissue to be treated. The fusion proteins are administered in any suitable manner, preferably with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions that are available (see, e.g., Remington: The Science and Practice of Pharmacy, 21st ed., 2005).

The fusion proteins, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The disclosed compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

EXAMPLES

The invention is further described in the following examples, which do not limit the scope of the invention described in the claims.

Figure 1A:
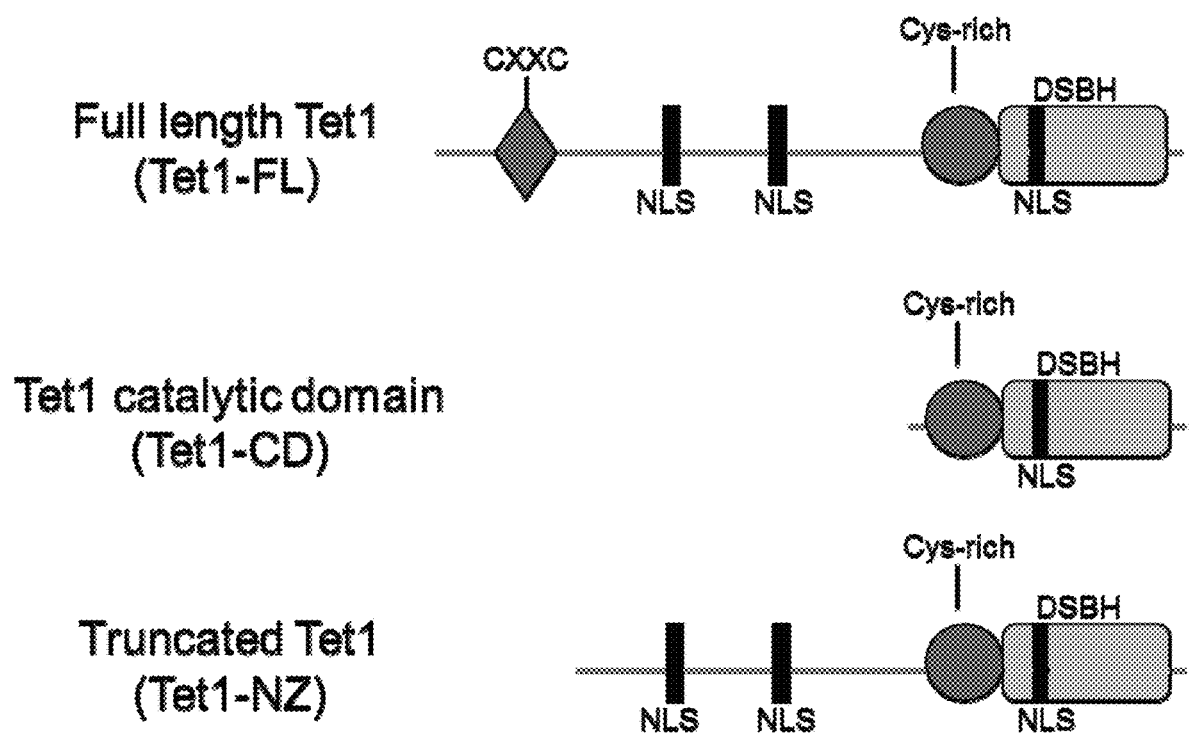
FIGS. 1A-B. Structure of Tet1 and TAL-Tet1 fusion proteins.
Figure 1B:
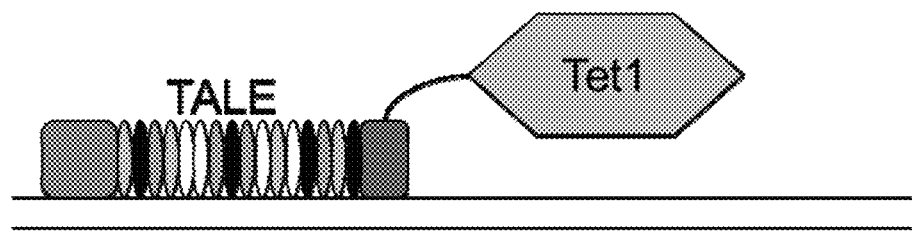

Example 1. Generation of TAL-Tet1 Fusion Proteins to Specific Genomic Loci in the Endogenous Human KLF4 Gene Plasmids expressing three different versions of the human Tet1 protein were constructed based on the predicted domain architecture described by Tahiliani et al. (Science 324, 930-935 (2009)) (FIG. 1A). Tet1-FL is the full length Tet1 protein, while Tet1-CD comprises only the catalytic domain of the protein, including the Cys-rich region and the double-stranded β-helix domain (FIG. 5). Tet1-NZ is an intermediate truncation variant that lacks a CXXC-type zinc-binding domain, which may be responsible for directing DNA-binding of the endogenous protein (Zhang et al., Cell Res 20, 1390-1393 (2010); Xu et al., Mol. Cell 42, 451-464 (2011); FIG. 5). Note that Tet1-NZ maintains more of the native protein than Tet1-CD alone. Briefly, DNA fragments encoding full-length Tet1 (Tet1-FL; amino acids 1-2136) and Tet1 catalytic domain (Tet1-CD; amino acids 1418-2136) were synthesized in 8 pieces (Integrated DNA Technologies) and iteratively cloned together using standard restriction digest/ligation based cloning.

These fragments encoding Tet1-FL and Tet1-CD were then cloned into a plasmid vector that enables their expression as fusions to the carboxy-terminal end of four different engineered TAL repeat array protein domains designed to bind different 18 bp target sites within the second intron of the human Klf4 gene (see FIG. 2). The linker sequences used to join the Tet1 protein or Tet1 protein fragments to the TAL effector repeat arrays were composed of one of the following linkers: Gly$_3$Ser (SEQ ID NO:5), Gly$_3$SerGly$_4$SerArgSer (SEQ ID NO:6), Gly$_3$Ser(Gly$_4$Ser)$_2$ArgSer (SEQ ID NO:7), Gly$_3$Ser(Gly$_4$Ser)$_3$ArgSer (SEQ ID NO:8), Gly$_3$Ser(Gly$_4$Ser)$_4$ArgSer (SEQ ID NO:9), or Gly$_3$Ser(Gly$_4$Ser)$_5$ArgSer (SEQ ID NO:10).

The final expression plasmid placed the fusion proteins under the transcriptional control of a constitutively active EF1α promoter. Tet1-NZ was constructed by removing the CXXC domain located at amino acids 584-624 of the full length protein. This was achieved by using tailed PCR of a small segment of Tet1-FL that placed a BamHI site immediately after the CXXC domain and included a PmlI site upstream of the CXXC domain that is unique in the Tet1-FL expression plasmid. This PCR product was then cloned into the Tet1-FL expression plasmid using a BamHI/PmlI double digest of both the PCR product and the Tet1-FL plasmid followed by ligation and transformation.

The four genomic loci chosen to target for demethylation (and for which TAL effector repeat arrays were designed) were selected based on several criteria. All four loci lie within intron 1-2 of the human KLF4 gene, which exhibits marks of open chromatin based on data from the ENCODE project (as accessed through the UCSC Genome Browser), suggesting its likely accessibility for binding by TAL effector DNA binding domains. This intron was also attractive because it harbors multiple CpG diresidues that are methylated in K562 cells but that are unmethylated in human embyronic stem cells, suggesting that methylation of these cytosines is not necessary for cell survival or viability.

TAL effector repeat arrays were engineered using the previously described FLASH assembly method (Reyon et al. FLASH assembly of TALENs for high-throughput genome editing. Nat Biotechnol (2012).doi:10.1038/nbt.2170). DNA fragments encoding assembled arrays were cloned into expression constructs containing amino acids 153 to 288 from the TALE13 protein and the +95 C-terminal domain, comprised of amino acids 715 to 809 from the C-terminal end of TALE13 (Miller et al., Nat Biotechnol 29, 143-148 (2010)).

Example 2. Site-Specific Demethylation of CpGs in the Human KLF4 Locus Mediated by TAL-Tet1 Fusion Proteins Human K562 cells were cultured in RPMI 1640 medium (Gibco) with 10% HIFBS (Gibco), 1% GLUTAMAX (Gibco) and 1% Pen/Strep (Gibco), and were transfected with plasmids encoding various TAL-Tet1-CD fusion proteins harboring the Gly$_3$Ser (SEQ ID NO:5) linker by nucleofecting 1×10$^6$ dividing cells with 10 µg of DNA in 100 µl of Kit V solution (Lonza) using program T-016 on the Nucleofector 2b Device (Lonza) Nucleofected cells were incubated in 6-well plates at 37° C. for 4 days following NUCLEOFECTION. Genomic DNA was harvested 4 days post-transfection Bisulfite DNA sequencing of KLF4 intron 1-2 from these transfected cell populations was performed as follows. Genomic DNA was isolated from transfected cells using the Qiagen Blood Mini kit. 200-1000ng of genomic DNA was bisulfite treated using either the EZ DNA Methylation Kit (Zymo), EZ DNA METHYLATION-LIGHTNING Kit (Zymo), or Cells-to-CpG Bisulfite Conversion Kit (Applied Biosystems) following recommended protocols. PCR amplification of Bis-DNA was performed using ACCUPRIME HiFi Taq DNA polymerase system (Invitrogen) PCR products were TA-cloned using the Original TA Cloning protocol (Invitrogen) or the pGEM-T Easy Vector System (Promega) and transformed into either Top10 or XL1-BLUE competent cells Individual clones were miniprepped and sequenced and sequences were analyzed using the BISMA software available online at (Rohde et al., BMC Bioinformatics 2010, 11:230), using default parameters.

The results revealed robust demethylation at CpGs positioned adjacent to the site bound by each of these TAL-Tet1-CD fusion proteins. FIG. 3 shows the rates of demethylation for CpGs near the four different TAL binding sites. TAL-Tet1-CD protein targeted to site 1 showed the highest levels of demethylation with 32.5% and 45.4% demethylation of CpGs located 9 and 15 bp downstream of the target binding site, respectively. TAL-Tet1-CD protein targeted to site 2 showed no demethylation of CpGs located 1 and 3 bp downstream of the binding site but did show 36.5% and 28.2% demethylation at CpGs located 17 and 27 bp downstream, respectively. TAL-Tet1 protein targeted to site 3 showed several greater than 25% demethylation at CpGs located 22, 36, 116 and 143 bp downstream, and a TAL-Tet1-CD protein targeted to site 4 showed a 37% demethylation at a CpG located 13 bp downstream but failed to show significant demethylation at any other CpGs.

Overall, this demonstrates the ability of engineered T AL-Tet1-CD fusion proteins harboring a Gly$_3$Ser (SEQ ID NO:5) linker to induce 30-50% demethylation of CpGs located approximately 10-30 bp downstream of the TAL binding site. (Note for all of these cases, "downstream" refers to bases located 3' to the last base of the binding site contacted by the carboxy-terminal TAL effector repeat in the fusion protein.) TAL-Tet1-CD fusion proteins harboring more extended linkers (Gly$_3$SerGly$_4$SerArgSer (SEQ ID NO:6), Gly$_3$Ser(Gly$_4$SerArgSer (SEQ ID NO:7). Gly$_3$Ser (Gly$_4$Ser)$_3$ArgSer(SEQ ID NO:8), Gly$_3$Ser(Gly$_4$Ser)ArgSer (SEQ ID NO:9), or Gly$_3$Ser(Gly$_4$Ser)$_5$ArgSer (SEQ ID NO:10)also showed similar levels of demethylation (FIG. 4).

Example 3. Engineered TALE-Tet1 Proteins Targeted to the Human HBB Locus

Published work has identified a small number of CpGs in the human β-globin and γ-globin promoters which are differentially methylated in fetal liver and adult bone marrow cells and has suggested that methylation of these CpGs may dictate expression of these genes during development (Mabaera et al., Blood. 2007 Aug. 15; 110(4):1343-52). TALE arrays targeted to sequences near these differentially methylated CpGs at the human β-globin locus were engineered: four TALEs targeted to a set of two CpGs ~100 bp downstream of the transcription start site and six TALEs targeted to a set of two CpGs ~300 bp upstream of the start site.

Human K62 cells were cultured in RPMI 1640 medium (Gibco) with 10% HIFBS (Gibco), 1% GLUTAMAX (Gibco) and 1% Pen/Strep (Gibco), and were transfected with plasmids encoding various TAL-Tet1-CD fusion proteins harboring the Gly$_3$Ser (SEQ ID NO:5) linker by nucleofecting 1×10$^6$ dividing cells with 10 µg of DNA in 100 µl of Kit V solution (Lonza) using program T-016 on the Nucleofector 2b Device (Lonza) Nucleofected cells were incubated in 6-well plates at 37° C. for 4 days following NUCLEOFECTION. Genomic DNA was harvested 4 days post-transfection. Bisulfite DNA sequencing of the HBB locus from these transfected cell populations was performed as follows, Genomic DNA was isolated from transfected cells using the Qiagen Blood Mini kit 200-1000 ng of genomic DNA was bisulfite treated using either the EZ DNA Methylation Kit (Zymo), EZ DNA METHYLATION-LIGHTNING Kit (Zymo), or Cells-to-CpG Bisulfite Conversion Kit (Applied Biosystems) following recommended protocols. PCR amplification of Bis-DNA was performed using Pyromark PCR kit (Qiagen) Illumina adapters and barcodes were added by PCR with Phusion High-Fidelity PCR enzyme (NEB) and amplicons were sequenced on an Illumina MISEQ system. Total RNA was isolated from the same cells with the PURELINK RNA mini kit (Ambion) according to manufacture's instructions. Reverse transcription was performed with the SUPERSCRIPTIII RT kit (Invitrogen) and TAQMAN assays were nm on an Applied Biosystems 7500Fast Real Time PCR machine.

All TALE-Tet1 fusions were able to reduce methylation of CpGs located downstream of the TALE binding site, albeit with varying efficiencies (FIGS. 8A-B). Interestingly, qRT-PCR analysis of β-globin levels showed increased expression only in those cells transfected with one of three TALE-Tet1 proteins targeting the CpG 266 bp upstream of the transcription start site (FIG. 8C). Thus, while all of the TALE-Tet1 proteins were able to catalyze demethylation of nearby CpGs, only demethylation of this single CpG causes increased expression of the β-globin gene.

These results demonstrate that the TALE-Tet1 fusion proteins can be used to demethylate specific CpG residues in a gene promoter and thereby upregulate expression of that gene in living cells.

Example 4. Engineered ZF-Tet1 Fusion Proteins

In addition to generating TALE-Tet1 fusions, Zinc Finger (ZF)-Tet1 fusion proteins were also engineered. Six-finger zinc finger proteins were assembled from two-finger ZF units derived from OPEN-selected proteins. Two ZF-Tet1 fusions targeted to the Klf4 locus and five targeted to the β-globin locus were engineered.

Upon transfection into K562 cells, one of the Klf4 ZF-Tet1 proteins was able to demethylate CpGs located 6 and 24 bp downstream of the ZF binding site by 68 and 25%, respectively (FIG. 9A).

Additionally, five ZF-Tet1 proteins targeted to the two CpGs located ~100 bp downstream of the β-globin transcription start site were engineered. All five of these proteins were able to induce demethylation of CpGs located downstream of the ZF binding site, albeit with varying efficiencies (FIG. 9B). This data demonstrates that the catalytic domain of Tet1 can be fused to alternate DNA-binding domains in order to generate site-specific DNA demethylation enzymes, resulting upregulation of expression of targeted genes in living cells.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A nucleic acid encoding a fusion protein comprising
an engineered transcription activator-like (TAL) effector repeat array or a zinc finger protein DNA-binding domain that is capable of specifically binding to a DNA sequence that is within 250 bp of a CpG diresidue in a mammalian cell, fused to
a catalytic domain comprising a catalytic domain of Tet1 comprising amino acids 1580-2052 of SEQ ID NO: 2, and excluding amino acids 584-624 of SEQ ID NO:2, that is capable of catalyzing hydroxylation of methylated cytosines in DNA.

2. The nucleic acid of claim 1, wherein the fusion protein further comprises a linker between the DNA binding domain and the catalytic domain.

3. The nucleic acid of claim 1, wherein the fusion protein comprises a plurality of catalytic domains.

4. The nucleic acid of claim 1, wherein the DNA-binding domain comprises a six-finger zinc finger protein.

5. The nucleic acid of claim 1, wherein the catalytic domain consists of the amino acid sequence of SEQ ID NO:4.

6. A vector comprising the nucleic acid of claim 1.

7. The vector of claim 6, wherein the vector is a DNA plasmid, an adeno-associated virus, or a retrovirus.

8. A composition comprising the nucleic acid of claim 1 and a delivery vehicle.

9. The composition of claim 8, wherein the delivery vehicle is a liposome.

10. A method of reducing methylation of a CpG diresidue in a mammalian cell, the method comprising contacting the cell with a nucleic acid encoding a fusion protein comprising
an engineered transcription activator-like (TAL) effector repeat array or a zinc finger protein DNA-binding domain that is capable of specifically binding to a DNA sequence that is within 250 bp of a CpG diresidue in a mammalian cell, fused to
a catalytic domain comprising a catalytic domain of Tet1 comprising amino acids 1580-2052 of SEQ ID NO: 2, and excluding amino acids 584-624 of SEQ ID NO:2, that is capable of catalyzing hydroxylation of methylated cytosines in DNA, and wherein the fusion protein reduces methylation of the CpG diresidue.

11. The method of claim 10, wherein the cell is a human cell.

12. The method of claim 10, wherein the DNA sequence is a gene selected from the group consisting of RASSF1A, MGMT, BRCA1, p16, CDH1, TIMP-3, p15, p73, DAPK, APC, and RELN.

13. The method of claim 10, wherein the DNA sequence is within 100 bp of the CpG diresidue.

14. The method of claim 10, wherein the DNA sequence is within 30 bp of the CpG diresidue.

* * * * *

SEQUENCE LISTING

```
<160> NUMBER OF SEQ ID NOS: 10

<210> SEQ ID NO 1
<211> LENGTH: 280
<212> TYPE: DNA
<213> ORGANISM: Homo sapiens

<400> SEQUENCE: 1
gggggcgggc ggagccttgg ggtcaccaag agccactgaa cgagggtaag gagcggccac      60
cgcgcggact ccgcaacctt cccgggatag cttccgtgtc cttggctcag ctgtgtatgc     120
ccgtggtgcg agcactgcgg agccgcctgg ggcgcaagcc gggtcttcac cagtccccgg     180
gcgcgctgtc ggtagggcgg gcgctctcgg gccaccgggc gggaggtggc cgcgtcccca     240
gacactggct gggccagagt gagtttagcg cgtaggcggc                           280

<210> SEQ ID NO 2
<211> LENGTH: 2136
<212> TYPE: PRT
<213> ORGANISM: Homo sapiens

<400> SEQUENCE: 2

Met Ser Arg Ser Arg His Ala Arg Pro Ser Arg Leu Val Arg Lys Glu
1               5                   10                  15

Asp Val Asn Lys Lys Lys Lys Asn Ser Gln Leu Arg Lys Thr Thr Lys
                20                  25                  30

Gly Ala Asn Lys Asn Val Ala Ser Val Lys Thr Leu Ser Pro Gly Lys
            35                  40                  45

Leu Lys Gln Leu Ile Gln Glu Arg Asp Val Lys Lys Lys Thr Glu Pro
        50                  55                  60

Lys Pro Pro Val Pro Val Arg Ser Leu Leu Thr Arg Ala Gly Ala Ala
65                  70                  75                  80

Arg Met Asn Leu Asp Arg Thr Glu Val Leu Phe Gln Asn Pro Glu Ser
                85                  90                  95

Leu Thr Cys Asn Gly Phe Thr Met Ala Leu Arg Ser Thr Ser Leu Ser
            100                 105                 110

Arg Arg Leu Ser Gln Pro Pro Leu Val Val Ala Lys Ser Lys Lys Val
        115                 120                 125

Pro Leu Ser Lys Gly Leu Glu Lys Gln His Asp Cys Asp Tyr Lys Ile
    130                 135                 140

Leu Pro Ala Leu Gly Val Lys His Ser Glu Asn Asp Ser Val Pro Met
145                 150                 155                 160
```

-continued

Gln Asp Thr Gln Val Leu Pro Asp Ile Glu Thr Leu Ile Gly Val Gln
            165                 170                 175

Asn Pro Ser Leu Leu Lys Gly Lys Ser Gln Glu Thr Thr Gln Phe Trp
        180                 185                 190

Ser Gln Arg Val Glu Asp Ser Lys Ile Asn Ile Pro Thr His Ser Gly
        195                 200                 205

Pro Ala Ala Glu Ile Leu Pro Gly Pro Leu Glu Gly Thr Arg Cys Gly
210                 215                 220

Glu Gly Leu Phe Ser Glu Thr Leu Asn Asp Thr Ser Gly Ser Pro
225                 230                 235                 240

Lys Met Phe Ala Gln Asp Thr Val Cys Ala Pro Phe Pro Gln Arg Ala
            245                 250                 255

Thr Pro Lys Val Thr Ser Gln Gly Asn Pro Ser Ile Gln Leu Glu Glu
        260                 265                 270

Leu Gly Ser Arg Val Glu Ser Leu Lys Leu Ser Asp Ser Tyr Leu Asp
    275                 280                 285

Pro Ile Lys Ser Glu His Asp Cys Tyr Pro Thr Ser Ser Leu Asn Lys
    290                 295                 300

Val Ile Pro Asp Leu Asn Leu Arg Asn Cys Leu Ala Leu Gly Gly Ser
305                 310                 315                 320

Thr Ser Pro Thr Ser Val Ile Lys Phe Leu Leu Ala Gly Ser Lys Gln
            325                 330                 335

Ala Thr Leu Gly Ala Lys Pro Asp His Gln Glu Ala Phe Glu Ala Thr
        340                 345                 350

Ala Asn Gln Gln Glu Val Ser Asp Thr Thr Ser Phe Leu Gly Gln Ala
    355                 360                 365

Phe Gly Ala Ile Pro His Gln Trp Glu Leu Pro Gly Ala Asp Pro Val
370                 375                 380

His Gly Glu Ala Leu Gly Glu Thr Pro Asp Leu Pro Glu Ile Pro Gly
385                 390                 395                 400

Ala Ile Pro Val Gln Gly Glu Val Phe Gly Thr Ile Leu Asp Gln Gln
            405                 410                 415

Glu Thr Leu Gly Met Ser Gly Ser Val Val Pro Asp Leu Pro Val Phe
        420                 425                 430

Leu Pro Val Pro Pro Asn Pro Ile Ala Thr Phe Asn Ala Pro Ser Lys
    435                 440                 445

Trp Pro Glu Pro Gln Ser Thr Val Ser Tyr Gly Leu Ala Val Gln Gly
    450                 455                 460

Ala Ile Gln Ile Leu Pro Leu Gly Ser Gly His Thr Pro Gln Ser Ser
465                 470                 475                 480

Ser Asn Ser Glu Lys Asn Ser Leu Pro Pro Val Met Ala Ile Ser Asn
            485                 490                 495

Val Glu Asn Glu Lys Gln Val His Ile Ser Phe Leu Pro Ala Asn Thr
        500                 505                 510

Gln Gly Phe Pro Leu Ala Pro Glu Arg Gly Leu Phe His Ala Ser Leu
    515                 520                 525

Gly Ile Ala Gln Leu Ser Gln Ala Gly Pro Ser Lys Ser Asp Arg Gly
    530                 535                 540

Ser Ser Gln Val Ser Val Thr Ser Thr Val His Val Val Asn Thr Thr
545                 550                 555                 560

Val Val Thr Met Pro Val Pro Met Val Ser Thr Ser Ser Ser Ser Tyr
            565                 570                 575

```
Thr Thr Leu Leu Pro Thr Leu Glu Lys Lys Arg Lys Arg Cys Gly
            580             585             590

Val Cys Glu Pro Cys Gln Gln Lys Thr Asn Cys Gly Glu Cys Thr Tyr
        595             600             605

Cys Lys Asn Arg Lys Asn Ser His Gln Ile Cys Lys Lys Arg Lys Cys
        610             615             620

Glu Glu Leu Lys Lys Lys Pro Ser Val Val Pro Leu Glu Val Ile
625             630             635             640

Lys Glu Asn Lys Arg Pro Gln Arg Glu Lys Pro Lys Val Leu Lys
            645             650             655

Ala Asp Phe Asp Asn Lys Pro Val Asn Gly Pro Lys Ser Glu Ser Met
        660             665             670

Asp Tyr Ser Arg Cys Gly His Gly Glu Glu Gln Lys Leu Glu Leu Asn
        675             680             685

Pro His Thr Val Glu Asn Val Thr Lys Asn Glu Asp Ser Met Thr Gly
        690             695             700

Ile Glu Val Glu Lys Trp Thr Gln Asn Lys Lys Ser Gln Leu Thr Asp
705             710             715             720

His Val Lys Gly Asp Phe Ser Ala Asn Val Pro Glu Ala Glu Lys Ser
            725             730             735

Lys Asn Ser Glu Val Asp Lys Lys Arg Thr Lys Ser Pro Lys Leu Phe
        740             745             750

Val Gln Thr Val Arg Asn Gly Ile Lys His Val His Cys Leu Pro Ala
            755             760             765

Glu Thr Asn Val Ser Phe Lys Lys Phe Asn Ile Glu Glu Phe Gly Lys
        770             775             780

Thr Leu Glu Asn Asn Ser Tyr Lys Phe Leu Lys Asp Thr Ala Asn His
785             790             795             800

Lys Asn Ala Met Ser Ser Val Ala Thr Asp Met Ser Cys Asp His Leu
            805             810             815

Lys Gly Arg Ser Asn Val Leu Val Phe Gln Gln Pro Gly Phe Asn Cys
        820             825             830

Ser Ser Ile Pro His Ser His Ser Ile Ile Asn His His Ala Ser
        835             840             845

Ile His Asn Glu Gly Asp Gln Pro Lys Thr Pro Glu Asn Ile Pro Ser
850             855             860

Lys Glu Pro Lys Asp Gly Ser Pro Val Gln Pro Ser Leu Leu Ser Leu
865             870             875             880

Met Lys Asp Arg Arg Leu Thr Leu Glu Gln Val Val Ala Ile Glu Ala
            885             890             895

Leu Thr Gln Leu Ser Glu Ala Pro Ser Glu Asn Ser Ser Pro Ser Lys
        900             905             910

Ser Glu Lys Asp Glu Glu Ser Glu Gln Arg Thr Ala Ser Leu Leu Asn
        915             920             925

Ser Cys Lys Ala Ile Leu Tyr Thr Val Arg Lys Asp Leu Gln Asp Pro
        930             935             940

Asn Leu Gln Gly Glu Pro Pro Lys Leu Asn His Cys Pro Ser Leu Glu
945             950             955             960

Lys Gln Ser Ser Cys Asn Thr Val Val Phe Asn Gly Gln Thr Thr Thr
            965             970             975

Leu Ser Asn Ser His Ile Asn Ser Ala Thr Asn Gln Ala Ser Thr Lys
        980             985             990
```

-continued

Ser His Glu Tyr Ser Lys Val Thr Asn Ser Leu Ser Leu Phe Ile Pro
        995                1000                1005

Lys Ser Asn Ser Ser Lys Ile Asp Thr Asn Lys Ser Ile Ala Gln Gly
    1010                1015                1020

Ile Ile Thr Leu Asp Asn Cys Ser Asn Asp Leu His Gln Leu Pro Pro
1025                1030                1035                1040

Arg Asn Asn Glu Val Glu Tyr Cys Asn Gln Leu Leu Asp Ser Ser Lys
            1045                1050                1055

Lys Leu Asp Ser Asp Asp Leu Ser Cys Gln Asp Ala Thr His Thr Gln
        1060                1065                1070

Ile Glu Glu Asp Val Ala Thr Gln Leu Thr Gln Leu Ala Ser Ile Ile
    1075                1080                1085

Lys Ile Asn Tyr Ile Lys Pro Glu Asp Lys Lys Val Glu Ser Thr Pro
1090                1095                1100

Thr Ser Leu Val Thr Cys Asn Val Gln Gln Lys Tyr Asn Gln Glu Lys
1105                1110                1115                1120

Gly Thr Met Gln Gln Lys Pro Pro Ser Ser Val His Asn Asn His Gly
            1125                1130                1135

Ser Ser Leu Thr Lys Gln Lys Asn Pro Thr Gln Lys Lys Thr Lys Ser
        1140                1145                1150

Thr Pro Ser Arg Asp Arg Arg Lys Lys Lys Pro Thr Val Val Ser Tyr
    1155                1160                1165

Gln Glu Asn Asp Arg Gln Lys Trp Glu Lys Leu Ser Tyr Met Tyr Gly
    1170                1175                1180

Thr Ile Cys Asp Ile Trp Ile Ala Ser Lys Phe Gln Asn Phe Gly Gln
1185                1190                1195                1200

Phe Cys Pro His Asp Phe Pro Thr Val Phe Gly Lys Ile Ser Ser Ser
            1205                1210                1215

Thr Lys Ile Trp Lys Pro Leu Ala Gln Thr Arg Ser Ile Met Gln Pro
        1220                1225                1230

Lys Thr Val Phe Pro Pro Leu Thr Gln Ile Lys Leu Gln Arg Tyr Pro
    1235                1240                1245

Glu Ser Ala Glu Glu Lys Val Lys Val Glu Pro Leu Asp Ser Leu Ser
    1250                1255                1260

Leu Phe His Leu Lys Thr Glu Ser Asn Gly Lys Ala Phe Thr Asp Lys
1265                1270                1275                1280

Ala Tyr Asn Ser Gln Val Gln Leu Thr Val Asn Ala Asn Gln Lys Ala
            1285                1290                1295

His Pro Leu Thr Gln Pro Ser Ser Pro Pro Asn Gln Cys Ala Asn Val
        1300                1305                1310

Met Ala Gly Asp Asp Gln Ile Arg Phe Gln Gln Val Lys Glu Gln
        1315                1320                1325

Leu Met His Gln Arg Leu Pro Thr Leu Pro Gly Ile Ser His Glu Thr
    1330                1335                1340

Pro Leu Pro Glu Ser Ala Leu Thr Leu Arg Asn Val Asn Val Val Cys
1345                1350                1355                1360

Ser Gly Gly Ile Thr Val Val Ser Thr Lys Ser Glu Glu Val Cys
            1365                1370                1375

Ser Ser Ser Phe Gly Thr Ser Glu Phe Ser Thr Val Asp Ser Ala Gln
            1380                1385                1390

Lys Asn Phe Asn Asp Tyr Ala Met Asn Phe Phe Thr Asn Pro Thr Lys
        1395                1400                1405

-continued

```
Asn Leu Val Ser Ile Thr Lys Asp Ser Glu Leu Pro Thr Cys Ser Cys
    1410                1415                1420

Leu Asp Arg Val Ile Gln Lys Asp Lys Gly Pro Tyr Tyr Thr His Leu
1425                1430                1435                1440

Gly Ala Gly Pro Ser Val Ala Ala Val Arg Glu Ile Met Glu Asn Arg
                1445                1450                1455

Tyr Gly Gln Lys Gly Asn Ala Ile Arg Ile Glu Ile Val Val Tyr Thr
            1460                1465                1470

Gly Lys Glu Gly Lys Ser Ser His Gly Cys Pro Ile Ala Lys Trp Val
        1475                1480                1485

Leu Arg Arg Ser Ser Asp Glu Glu Lys Val Leu Cys Leu Val Arg Gln
    1490                1495                1500

Arg Thr Gly His His Cys Pro Thr Ala Val Met Val Val Leu Ile Met
1505                1510                1515                1520

Val Trp Asp Gly Ile Pro Leu Pro Met Ala Asp Arg Leu Tyr Thr Glu
                1525                1530                1535

Leu Thr Glu Asn Leu Lys Ser Tyr Asn Gly His Pro Thr Asp Arg Arg
            1540                1545                1550

Cys Thr Leu Asn Glu Asn Arg Thr Cys Thr Cys Gln Gly Ile Asp Pro
        1555                1560                1565

Glu Thr Cys Gly Ala Ser Phe Ser Phe Gly Cys Ser Trp Ser Met Tyr
    1570                1575                1580

Phe Asn Gly Cys Lys Phe Gly Arg Ser Pro Ser Pro Arg Arg Phe Arg
1585                1590                1595                1600

Ile Asp Pro Ser Ser Pro Leu His Glu Lys Asn Leu Glu Asp Asn Leu
                1605                1610                1615

Gln Ser Leu Ala Thr Arg Leu Ala Pro Ile Tyr Lys Gln Tyr Ala Pro
            1620                1625                1630

Val Ala Tyr Gln Asn Gln Val Glu Tyr Glu Asn Val Ala Arg Glu Cys
        1635                1640                1645

Arg Leu Gly Ser Lys Glu Gly Arg Pro Phe Ser Gly Val Thr Ala Cys
    1650                1655                1660

Leu Asp Phe Cys Ala His Pro His Arg Asp Ile His Asn Met Asn Asn
1665                1670                1675                1680

Gly Ser Thr Val Val Cys Thr Leu Thr Arg Glu Asp Asn Arg Ser Leu
                1685                1690                1695

Gly Val Ile Pro Gln Asp Glu Gln Leu His Val Leu Pro Leu Tyr Lys
            1700                1705                1710

Leu Ser Asp Thr Asp Glu Phe Gly Ser Lys Glu Gly Met Glu Ala Lys
        1715                1720                1725

Ile Lys Ser Gly Ala Ile Glu Val Leu Ala Pro Arg Arg Lys Lys Arg
    1730                1735                1740

Thr Cys Phe Thr Gln Pro Val Pro Arg Ser Gly Lys Lys Arg Ala Ala
1745                1750                1755                1760

Met Met Thr Glu Val Leu Ala His Lys Ile Arg Ala Val Glu Lys Lys
                1765                1770                1775

Pro Ile Pro Arg Ile Lys Arg Lys Asn Asn Ser Thr Thr Thr Asn Asn
            1780                1785                1790

Ser Lys Pro Ser Ser Leu Pro Thr Leu Gly Ser Asn Thr Glu Thr Val
        1795                1800                1805

Gln Pro Glu Val Lys Ser Glu Thr Glu Pro His Phe Ile Leu Lys Ser
    1810                1815                1820
```

```
Ser Asp Asn Thr Lys Thr Tyr Ser Leu Met Pro Ser Ala Pro His Pro
1825                1830                1835                1840

Val Lys Glu Ala Ser Pro Gly Phe Ser Trp Ser Pro Lys Thr Ala Ser
            1845                1850                1855

Ala Thr Pro Ala Pro Leu Lys Asn Asp Ala Thr Ala Ser Cys Gly Phe
                1860                1865                1870

Ser Glu Arg Ser Ser Thr Pro His Cys Thr Met Pro Ser Gly Arg Leu
        1875                1880                1885

Ser Gly Ala Asn Ala Ala Ala Asp Gly Pro Gly Ile Ser Gln Leu
        1890                1895                1900

Gly Glu Val Ala Pro Leu Pro Thr Leu Ser Ala Pro Val Met Glu Pro
1905                1910                1915                1920

Leu Ile Asn Ser Glu Pro Ser Thr Gly Val Thr Glu Pro Leu Thr Pro
                1925                1930                1935

His Gln Pro Asn His Gln Pro Ser Phe Leu Thr Ser Pro Gln Asp Leu
                1940                1945                1950

Ala Ser Ser Pro Met Glu Glu Asp Glu Gln His Ser Glu Ala Asp Glu
            1955                1960                1965

Pro Pro Ser Asp Glu Pro Leu Ser Asp Pro Leu Ser Pro Ala Glu
    1970                1975                1980

Glu Lys Leu Pro His Ile Asp Glu Tyr Trp Ser Asp Ser Glu His Ile
1985                1990                1995                2000

Phe Leu Asp Ala Asn Ile Gly Gly Val Ala Ile Ala Pro Ala His Gly
                2005                2010                2015

Ser Val Leu Ile Glu Cys Ala Arg Arg Glu Leu His Ala Thr Thr Pro
            2020                2025                2030

Val Glu His Pro Asn Arg Asn His Pro Thr Arg Leu Ser Leu Val Phe
                2035                2040                2045

Tyr Gln His Lys Asn Leu Asn Lys Pro Gln His Gly Phe Glu Leu Asn
                2050                2055                2060

Lys Ile Lys Phe Glu Ala Lys Glu Ala Lys Asn Lys Lys Met Lys Ala
2065                2070                2075                2080

Ser Glu Gln Lys Asp Gln Ala Ala Asn Glu Gly Pro Glu Gln Ser Ser
            2085                2090                2095

Glu Val Asn Glu Leu Asn Gln Ile Pro Ser His Lys Ala Leu Thr Leu
            2100                2105                2110

Thr His Asp Asn Val Val Thr Val Ser Pro Tyr Ala Leu Thr His Val
        2115                2120                2125

Ala Gly Pro Tyr Asn His Trp Val
    2130                2135

<210> SEQ ID NO 3
<211> LENGTH: 1512
<212> TYPE: PRT
<213> ORGANISM: Artificial Sequence
<220> FEATURE:
<223> OTHER INFORMATION: mutant human TET1

<400> SEQUENCE: 3

Glu Glu Leu Lys Lys Lys Pro Ser Val Val Pro Leu Glu Val Ile
1               5                   10                  15

Lys Glu Asn Lys Arg Pro Gln Arg Glu Lys Lys Pro Lys Val Leu Lys
                20                  25                  30

Ala Asp Phe Asp Asn Lys Pro Val Asn Gly Pro Lys Ser Glu Ser Met
                35                  40                  45
```

```
Asp Tyr Ser Arg Cys Gly His Gly Glu Glu Gln Lys Leu Glu Leu Asn
    50                  55                  60
Pro His Thr Val Glu Asn Val Thr Lys Asn Glu Asp Ser Met Thr Gly
65                  70                  75                  80
Ile Glu Val Glu Lys Trp Thr Gln Asn Lys Lys Ser Gln Leu Thr Asp
                85                  90                  95
His Val Lys Gly Asp Phe Ser Ala Asn Val Pro Glu Ala Glu Lys Ser
            100                 105                 110
Lys Asn Ser Glu Val Asp Lys Lys Arg Thr Lys Ser Pro Lys Leu Phe
        115                 120                 125
Val Gln Thr Val Arg Asn Gly Ile Lys His Val His Cys Leu Pro Ala
130                 135                 140
Glu Thr Asn Val Ser Phe Lys Lys Phe Asn Ile Glu Glu Phe Gly Lys
145                 150                 155                 160
Thr Leu Glu Asn Asn Ser Tyr Lys Phe Leu Lys Asp Thr Ala Asn His
                165                 170                 175
Lys Asn Ala Met Ser Ser Val Ala Thr Asp Met Ser Cys Asp His Leu
            180                 185                 190
Lys Gly Arg Ser Asn Val Leu Val Phe Gln Gln Pro Gly Phe Asn Cys
        195                 200                 205
Ser Ser Ile Pro His Ser Ser His Ser Ile Ile Asn His His Ala Ser
210                 215                 220
Ile His Asn Glu Gly Asp Gln Pro Lys Thr Pro Glu Asn Ile Pro Ser
225                 230                 235                 240
Lys Glu Pro Lys Asp Gly Ser Pro Val Gln Pro Ser Leu Leu Ser Leu
                245                 250                 255
Met Lys Asp Arg Arg Leu Thr Leu Glu Gln Val Val Ala Ile Glu Ala
            260                 265                 270
Leu Thr Gln Leu Ser Glu Ala Pro Ser Glu Asn Ser Ser Pro Ser Lys
        275                 280                 285
Ser Glu Lys Asp Glu Glu Ser Glu Gln Arg Thr Ala Ser Leu Leu Asn
290                 295                 300
Ser Cys Lys Ala Ile Leu Tyr Thr Val Arg Lys Asp Leu Gln Asp Pro
305                 310                 315                 320
Asn Leu Gln Gly Glu Pro Pro Lys Leu Asn His Cys Pro Ser Leu Glu
                325                 330                 335
Lys Gln Ser Ser Cys Asn Thr Val Val Phe Asn Gly Gln Thr Thr Thr
            340                 345                 350
Leu Ser Asn Ser His Ile Asn Ser Ala Thr Asn Gln Ala Ser Thr Lys
        355                 360                 365
Ser His Glu Tyr Ser Lys Val Thr Asn Ser Leu Ser Leu Phe Ile Pro
370                 375                 380
Lys Ser Asn Ser Ser Lys Ile Asp Thr Asn Lys Ser Ile Ala Gln Gly
385                 390                 395                 400
Ile Ile Thr Leu Asp Asn Cys Ser Asn Asp Leu His Gln Leu Pro Pro
                405                 410                 415
Arg Asn Asn Glu Val Glu Tyr Cys Asn Gln Leu Leu Ser Ser Lys
            420                 425                 430
Lys Leu Asp Ser Asp Asp Leu Ser Cys Gln Asp Ala Thr His Thr Gln
        435                 440                 445
Ile Glu Glu Asp Val Ala Thr Gln Leu Thr Gln Leu Ala Ser Ile Ile
450                 455                 460
```

-continued

```
Lys Ile Asn Tyr Ile Lys Pro Glu Asp Lys Lys Val Glu Ser Thr Pro
465                 470                 475                 480

Thr Ser Leu Val Thr Cys Asn Val Gln Gln Lys Tyr Asn Gln Glu Lys
                485                 490                 495

Gly Thr Met Gln Gln Lys Pro Pro Ser Ser Val His Asn Asn His Gly
            500                 505                 510

Ser Ser Leu Thr Lys Gln Lys Asn Pro Thr Gln Lys Lys Thr Lys Ser
        515                 520                 525

Thr Pro Ser Arg Asp Arg Arg Lys Lys Lys Pro Thr Val Val Ser Tyr
    530                 535                 540

Gln Glu Asn Asp Arg Gln Lys Trp Glu Lys Leu Ser Tyr Met Tyr Gly
545                 550                 555                 560

Thr Ile Cys Asp Ile Trp Ile Ala Ser Lys Phe Gln Asn Phe Gly Gln
                565                 570                 575

Phe Cys Pro His Asp Phe Pro Thr Val Phe Gly Lys Ile Ser Ser Ser
            580                 585                 590

Thr Lys Ile Trp Lys Pro Leu Ala Gln Thr Arg Ser Ile Met Gln Pro
        595                 600                 605

Lys Thr Val Phe Pro Pro Leu Thr Gln Ile Lys Leu Gln Arg Tyr Pro
    610                 615                 620

Glu Ser Ala Glu Glu Lys Val Lys Val Glu Pro Leu Asp Ser Leu Ser
625                 630                 635                 640

Leu Phe His Leu Lys Thr Glu Ser Asn Gly Lys Ala Phe Thr Asp Lys
                645                 650                 655

Ala Tyr Asn Ser Gln Val Gln Leu Thr Val Asn Ala Asn Gln Lys Ala
            660                 665                 670

His Pro Leu Thr Gln Pro Ser Ser Pro Asn Gln Cys Ala Asn Val
        675                 680                 685

Met Ala Gly Asp Asp Gln Ile Arg Phe Gln Gln Val Val Lys Glu Gln
    690                 695                 700

Leu Met His Gln Arg Leu Pro Thr Leu Pro Gly Ile Ser His Glu Thr
705                 710                 715                 720

Pro Leu Pro Glu Ser Ala Leu Thr Leu Arg Asn Val Asn Val Val Cys
                725                 730                 735

Ser Gly Gly Ile Thr Val Val Ser Thr Lys Ser Glu Glu Val Cys
            740                 745                 750

Ser Ser Ser Phe Gly Thr Ser Glu Phe Ser Thr Val Asp Ser Ala Gln
        755                 760                 765

Lys Asn Phe Asn Asp Tyr Ala Met Asn Phe Phe Thr Asn Pro Thr Lys
    770                 775                 780

Asn Leu Val Ser Ile Thr Lys Asp Ser Glu Leu Pro Thr Cys Ser Cys
785                 790                 795                 800

Leu Asp Arg Val Ile Gln Lys Asp Lys Gly Pro Tyr Tyr Thr His Leu
                805                 810                 815

Gly Ala Gly Pro Ser Val Ala Ala Val Arg Glu Ile Met Glu Asn Arg
            820                 825                 830

Tyr Gly Gln Lys Gly Asn Ala Ile Arg Ile Glu Ile Val Val Tyr Thr
        835                 840                 845

Gly Lys Glu Gly Lys Ser Ser His Gly Cys Pro Ile Ala Lys Trp Val
    850                 855                 860

Leu Arg Arg Ser Ser Asp Glu Glu Lys Val Leu Cys Leu Val Arg Gln
865                 870                 875                 880
```

-continued

```
Arg Thr Gly His His Cys Pro Thr Ala Val Met Val Leu Ile Met
            885                 890                 895

Val Trp Asp Gly Ile Pro Leu Pro Met Ala Asp Arg Leu Tyr Thr Glu
            900                 905                 910

Leu Thr Glu Asn Leu Lys Ser Tyr Asn Gly His Pro Thr Asp Arg Arg
            915                 920                 925

Cys Thr Leu Asn Glu Asn Arg Thr Cys Thr Cys Gln Gly Ile Asp Pro
            930                 935                 940

Glu Thr Cys Gly Ala Ser Phe Ser Phe Gly Cys Ser Trp Ser Met Tyr
945                 950                 955                 960

Phe Asn Gly Cys Lys Phe Gly Arg Ser Pro Ser Pro Arg Arg Phe Arg
                965                 970                 975

Ile Asp Pro Ser Ser Pro Leu His Glu Lys Asn Leu Glu Asp Asn Leu
            980                 985                 990

Gln Ser Leu Ala Thr Arg Leu Ala Pro Ile Tyr Lys Gln Tyr Ala Pro
            995                 1000                1005

Val Ala Tyr Gln Asn Gln Val Glu Tyr Glu Asn Val Ala Arg Glu Cys
            1010                1015                1020

Arg Leu Gly Ser Lys Glu Gly Arg Pro Phe Ser Gly Val Thr Ala Cys
1025                1030                1035                1040

Leu Asp Phe Cys Ala His Pro His Arg Asp Ile His Asn Met Asn Asn
                1045                1050                1055

Gly Ser Thr Val Val Cys Thr Leu Thr Arg Glu Asp Asn Arg Ser Leu
            1060                1065                1070

Gly Val Ile Pro Gln Asp Glu Gln Leu His Val Leu Pro Leu Tyr Lys
            1075                1080                1085

Leu Ser Asp Thr Asp Glu Phe Gly Ser Lys Glu Gly Met Glu Ala Lys
            1090                1095                1100

Ile Lys Ser Gly Ala Ile Glu Val Leu Ala Pro Arg Arg Lys Lys Arg
1105                1110                1115                1120

Thr Cys Phe Thr Gln Pro Val Pro Arg Ser Gly Lys Lys Arg Ala Ala
                1125                1130                1135

Met Met Thr Glu Val Leu Ala His Lys Ile Arg Ala Val Glu Lys Lys
            1140                1145                1150

Pro Ile Pro Arg Ile Lys Arg Lys Asn Asn Ser Thr Thr Thr Asn Asn
            1155                1160                1165

Ser Lys Pro Ser Ser Leu Pro Thr Leu Gly Ser Asn Thr Glu Thr Val
            1170                1175                1180

Gln Pro Glu Val Lys Ser Glu Thr Glu Pro His Phe Ile Leu Lys Ser
1185                1190                1195                1200

Ser Asp Asn Thr Lys Thr Tyr Ser Leu Met Pro Ser Ala Pro His Pro
                1205                1210                1215

Val Lys Glu Ala Ser Pro Gly Phe Ser Trp Ser Pro Lys Thr Ala Ser
            1220                1225                1230

Ala Thr Pro Ala Pro Leu Lys Asn Asp Ala Thr Ala Ser Cys Gly Phe
            1235                1240                1245

Ser Glu Arg Ser Ser Thr Pro His Cys Thr Met Pro Ser Gly Arg Leu
            1250                1255                1260

Ser Gly Ala Asn Ala Ala Ala Asp Gly Pro Gly Ile Ser Gln Leu
1265                1270                1275                1280

Gly Glu Val Ala Pro Leu Pro Thr Leu Ser Ala Pro Val Met Glu Pro
                1285                1290                1295
```

-continued

```
Leu Ile Asn Ser Glu Pro Ser Thr Gly Val Thr Glu Pro Leu Thr Pro
            1300                1305                1310

His Gln Pro Asn His Gln Pro Ser Phe Leu Thr Ser Pro Gln Asp Leu
        1315                1320                1325

Ala Ser Ser Pro Met Glu Glu Asp Glu Gln His Ser Glu Ala Asp Glu
    1330                1335                1340

Pro Pro Ser Asp Glu Pro Leu Ser Asp Pro Leu Ser Pro Ala Glu
1345                1350                1355                1360

Glu Lys Leu Pro His Ile Asp Glu Tyr Trp Ser Asp Ser Glu His Ile
                1365                1370                1375

Phe Leu Asp Ala Asn Ile Gly Gly Val Ala Ile Ala Pro Ala His Gly
            1380                1385                1390

Ser Val Leu Ile Glu Cys Ala Arg Arg Glu Leu His Ala Thr Thr Pro
        1395                1400                1405

Val Glu His Pro Asn Arg Asn His Pro Thr Arg Leu Ser Leu Val Phe
    1410                1415                1420

Tyr Gln His Lys Asn Leu Asn Lys Pro Gln His Gly Phe Glu Leu Asn
1425                1430                1435                1440

Lys Ile Lys Phe Glu Ala Lys Glu Ala Lys Asn Lys Lys Met Lys Ala
                1445                1450                1455

Ser Glu Gln Lys Asp Gln Ala Ala Asn Glu Gly Pro Glu Gln Ser Ser
            1460                1465                1470

Glu Val Asn Glu Leu Asn Gln Ile Pro Ser His Lys Ala Leu Thr Leu
        1475                1480                1485

Thr His Asp Asn Val Val Thr Val Ser Pro Tyr Ala Leu Thr His Val
    1490                1495                1500

Ala Gly Pro Tyr Asn His Trp Val
1505                1510

<210> SEQ ID NO 4
<211> LENGTH: 718
<212> TYPE: PRT
<213> ORGANISM: Artificial Sequence
<220> FEATURE:
<223> OTHER INFORMATION: fragment of human TET1

<400> SEQUENCE: 4

Leu Pro Thr Cys Ser Cys Leu Asp Arg Val Ile Gln Lys Asp Lys Gly
1               5                   10                  15

Pro Tyr Tyr Thr His Leu Gly Ala Gly Pro Ser Val Ala Ala Val Arg
            20                  25                  30

Glu Ile Met Glu Asn Arg Tyr Gly Gln Lys Gly Asn Ala Ile Arg Ile
        35                  40                  45

Glu Ile Val Val Tyr Thr Gly Lys Glu Gly Lys Ser Ser His Gly Cys
    50                  55                  60

Pro Ile Ala Lys Trp Val Leu Arg Arg Ser Ser Asp Glu Glu Lys Val
65                  70                  75                  80

Leu Cys Leu Val Arg Gln Arg Thr Gly His His Cys Pro Thr Ala Val
                85                  90                  95

Met Val Val Leu Ile Met Val Trp Asp Gly Ile Pro Leu Pro Met Ala
            100                 105                 110

Asp Arg Leu Tyr Thr Glu Leu Thr Glu Asn Leu Lys Ser Tyr Asn Gly
        115                 120                 125

His Pro Thr Asp Arg Arg Cys Thr Leu Asn Glu Asn Arg Thr Cys Thr
    130                 135                 140
```

```
Cys Gln Gly Ile Asp Pro Glu Thr Cys Gly Ala Ser Phe Ser Phe Gly
145                 150                 155                 160

Cys Ser Trp Ser Met Tyr Phe Asn Gly Cys Lys Phe Gly Arg Ser Pro
            165                 170                 175

Ser Pro Arg Arg Phe Arg Ile Asp Pro Ser Ser Pro Leu His Glu Lys
        180                 185                 190

Asn Leu Glu Asp Asn Leu Gln Ser Leu Ala Thr Arg Leu Ala Pro Ile
    195                 200                 205

Tyr Lys Gln Tyr Ala Pro Val Ala Tyr Gln Asn Val Glu Tyr Glu
    210                 215                 220

Asn Val Ala Arg Glu Cys Arg Leu Gly Ser Lys Glu Gly Arg Pro Phe
225                 230                 235                 240

Ser Gly Val Thr Ala Cys Leu Asp Phe Cys Ala His Pro His Arg Asp
            245                 250                 255

Ile His Asn Met Asn Asn Gly Ser Thr Val Val Cys Thr Leu Thr Arg
        260                 265                 270

Glu Asp Asn Arg Ser Leu Gly Val Ile Pro Gln Asp Glu Gln Leu His
    275                 280                 285

Val Leu Pro Leu Tyr Lys Leu Ser Asp Thr Asp Glu Phe Gly Ser Lys
290                 295                 300

Glu Gly Met Glu Ala Lys Ile Lys Ser Gly Ala Ile Glu Val Leu Ala
305                 310                 315                 320

Pro Arg Arg Lys Lys Arg Thr Cys Phe Thr Gln Pro Val Pro Arg Ser
            325                 330                 335

Gly Lys Lys Arg Ala Ala Met Met Thr Glu Val Leu Ala His Lys Ile
        340                 345                 350

Arg Ala Val Glu Lys Lys Pro Ile Pro Arg Ile Lys Arg Lys Asn Asn
    355                 360                 365

Ser Thr Thr Thr Asn Asn Ser Lys Pro Ser Ser Leu Pro Thr Leu Gly
370                 375                 380

Ser Asn Thr Glu Thr Val Gln Pro Glu Val Lys Ser Glu Thr Glu Pro
385                 390                 395                 400

His Phe Ile Leu Lys Ser Ser Asp Asn Thr Lys Thr Tyr Ser Leu Met
            405                 410                 415

Pro Ser Ala Pro His Pro Val Lys Glu Ala Ser Pro Gly Phe Ser Trp
        420                 425                 430

Ser Pro Lys Thr Ala Ser Ala Thr Pro Ala Pro Leu Lys Asn Asp Ala
    435                 440                 445

Thr Ala Ser Cys Gly Phe Ser Glu Arg Ser Ser Thr Pro His Cys Thr
450                 455                 460

Met Pro Ser Gly Arg Leu Ser Gly Ala Asn Ala Ala Ala Ala Asp Gly
465                 470                 475                 480

Pro Gly Ile Ser Gln Leu Gly Glu Val Ala Pro Leu Pro Thr Leu Ser
            485                 490                 495

Ala Pro Val Met Glu Pro Leu Ile Asn Ser Glu Pro Ser Thr Gly Val
        500                 505                 510

Thr Glu Pro Leu Thr Pro His Gln Pro Asn His Gln Pro Ser Phe Leu
    515                 520                 525

Thr Ser Pro Gln Asp Leu Ala Ser Ser Pro Met Glu Glu Asp Glu Gln
530                 535                 540

His Ser Glu Ala Asp Glu Pro Pro Ser Asp Glu Pro Leu Ser Asp Asp
545                 550                 555                 560
```

```
Pro Leu Ser Pro Ala Glu Glu Lys Leu Pro His Ile Asp Glu Tyr Trp
            565                 570                 575

Ser Asp Ser Glu His Ile Phe Leu Asp Ala Asn Ile Gly Gly Val Ala
        580                 585                 590

Ile Ala Pro Ala His Gly Ser Val Leu Ile Glu Cys Ala Arg Arg Glu
        595                 600                 605

Leu His Ala Thr Thr Pro Val Glu His Pro Asn Arg Asn His Pro Thr
        610                 615                 620

Arg Leu Ser Leu Val Phe Tyr Gln His Lys Asn Leu Asn Lys Pro Gln
625                 630                 635                 640

His Gly Phe Glu Leu Asn Lys Ile Lys Phe Glu Ala Lys Glu Ala Lys
                645                 650                 655

Asn Lys Lys Met Lys Ala Ser Glu Gln Lys Asp Gln Ala Ala Asn Glu
                660                 665                 670

Gly Pro Glu Gln Ser Ser Glu Val Asn Glu Leu Asn Gln Ile Pro Ser
            675                 680                 685

His Lys Ala Leu Thr Leu Thr His Asp Asn Val Val Thr Val Ser Pro
        690                 695                 700

Tyr Ala Leu Thr His Val Ala Gly Pro Tyr Asn His Trp Val
705                 710                 715

<210> SEQ ID NO 5
<211> LENGTH: 4
<212> TYPE: PRT
<213> ORGANISM: Artificial Sequence
<220> FEATURE:
<223> OTHER INFORMATION: linker sequence

<400> SEQUENCE: 5

Gly Gly Gly Ser
1

<210> SEQ ID NO 6
<211> LENGTH: 11
<212> TYPE: PRT
<213> ORGANISM: Artificial Sequence
<220> FEATURE:
<223> OTHER INFORMATION: linker sequence

<400> SEQUENCE: 6

Gly Gly Gly Ser Gly Gly Gly Ser Arg Ser
1               5                   10

<210> SEQ ID NO 7
<211> LENGTH: 16
<212> TYPE: PRT
<213> ORGANISM: Artificial Sequence
<220> FEATURE:
<223> OTHER INFORMATION: linker sequence

<400> SEQUENCE: 7

Gly Gly Gly Ser Gly Gly Gly Ser Gly Gly Gly Ser Arg Ser
1               5                   10                  15

<210> SEQ ID NO 8
<211> LENGTH: 21
<212> TYPE: PRT
<213> ORGANISM: Artificial Sequence
<220> FEATURE:
<223> OTHER INFORMATION: linker sequence
```

```
<400> SEQUENCE: 8

Gly Gly Gly Ser Gly Gly Gly Ser Gly Gly Gly Ser Gly Gly
1               5                   10                  15

Gly Gly Ser Arg Ser
            20

<210> SEQ ID NO 9
<211> LENGTH: 26
<212> TYPE: PRT
<213> ORGANISM: Artificial Sequence
<220> FEATURE:
<223> OTHER INFORMATION: linker sequence

<400> SEQUENCE: 9

Gly Gly Gly Ser Gly Gly Gly Ser Gly Gly Gly Ser Gly Gly
1               5                   10                  15

Gly Gly Ser Gly Gly Gly Gly Ser Arg Ser
            20                  25

<210> SEQ ID NO 10
<211> LENGTH: 31
<212> TYPE: PRT
<213> ORGANISM: Artificial Sequence
<220> FEATURE:
<223> OTHER INFORMATION: linker sequence

<400> SEQUENCE: 10

Gly Gly Gly Ser Gly Gly Gly Ser Gly Gly Gly Ser Gly Gly
1               5                   10                  15

Gly Gly Ser Gly Gly Gly Gly Ser Gly Gly Gly Gly Ser Arg Ser
            20                  25                  30
```